(12) United States Patent
Cristau et al.

(10) Patent No.: US 8,569,509 B2
(45) Date of Patent: Oct. 29, 2013

(54) THIAZOLE-4-CARBOXYLIC ACID ESTERS AND THIOESTERS AS PLANT PROTECTION AGENTS

(75) Inventors: Pierre Cristau, Cologne (DE); Stefan Herrmann, Langenfeld (DE); Nicola Rahn, Dusseldorf (DE); Arnd Voerste, Cologne (DE); Ulrike Wachendorff-Neumann, Neuwied (DE); Tomoki Tsuchiya, Dusseldorf (DE)

(73) Assignee: Bayer Intellectual Property GmbH, Monheim (DE)

( * ) Notice: Subject to any disclaimer, the term of this patent is extended or adjusted under 35 U.S.C. 154(b) by 344 days.

(21) Appl. No.: 12/990,358

(22) PCT Filed: Apr. 18, 2009

(86) PCT No.: PCT/EP2009/002850
§ 371 (c)(1),
(2), (4) Date: Oct. 29, 2010

(87) PCT Pub. No.: WO2009/132785
PCT Pub. Date: Nov. 5, 2009

(65) Prior Publication Data
US 2011/0105429 A1    May 5, 2011

(30) Foreign Application Priority Data

Apr. 30, 2008   (EP) .................................... 08155472

(51) Int. Cl.
*C07D 401/00* (2006.01)
*A61K 31/47* (2006.01)

(52) U.S. Cl.
USPC .......................................... 546/209; 514/314

(58) Field of Classification Search
USPC .......................................... 546/209; 514/314
See application file for complete search history.

(56) References Cited

U.S. PATENT DOCUMENTS

| | | | |
|---|---|---|---|
| 4,245,432 | A | 1/1981 | Dannelly |
| 4,272,417 | A | 6/1981 | Barke et al. |
| 4,808,430 | A | 2/1989 | Kouno |
| 5,876,739 | A | 3/1999 | Turnblad et al. |
| 2003/0176428 | A1 | 9/2003 | Schneidersmann et al. |

FOREIGN PATENT DOCUMENTS

| | | | |
|---|---|---|---|
| WO | WO 89/10396 A1 | 11/1989 | |
| WO | WO 96/33270 A1 | 10/1996 | |
| WO | WO 02/28186 A2 | 4/2002 | |
| WO | WO 02/080675 A1 | 10/2002 | |
| WO | WO 2004/058751 A1 | 7/2004 | |
| WO | WO 2005/003128 A1 | 1/2005 | |
| WO | WO 2007/014290 | * | 2/2007 |
| WO | WO 2007/014290 A2 | 2/2007 | |
| WO | WO 2007/024782 A2 | 3/2007 | |
| WO | WO 2007/027777 A2 | 3/2007 | |
| WO | WO 2008/091594 A2 | 7/2008 | |

OTHER PUBLICATIONS

Curphey, T.J., "Thionation of esters and lactones with the reagent combination of phosphorus pentasulfide and hexamethyldisiloxane," *Tet. Lett.* 43:371-373, Elsevier Science Ltd., United Kingdom (2002).
Draber, W. & Wegler, R., "Phytohormone: 2.Gibberelline", *Natürliche Pflanzenwuchsstoffe* 2:401-412, Springer Verlag, Berlin-Heidelberg-New York (1970).
Jensen, O.E. & Senning, A., "Studies on Amino Acids and Peptides X11 Synthesis of Thiated Analogues of Boc-S-Ala-Aib-S-Ala-OMe and Ac-S-Ala-Aib-S-Ala-OMe," *Tetrahedron* 42:6555-6564, Elsevier B.V., United Kingdom (1986).
Montalbetti, C.A.G.N. & Falque, V., "Amide bond formation and peptide coupling," *Tetrahedron* 61:10827-10852, Elsevier Ltd., United Kingdom (2005).
Rodik, R., et al., "Calix[4]arenesulfonylamidines. Synthesis, structure and influence on $Mg^{2+}$, ATP-dependent calcium pumps," *Tet. Lett.* 46:7459-7462, Elsevier Ltd., United Kingdom (2005).
Wardell, J.L., "The chemistry of the thiol group, Part 1," Chapter 4:163-269, John Wiley & Sons, Ltd., United States (1974).
International Search Report of International Application No. PCT/EP2009/002850, European Patent Office, Netherlands, mailed Oct. 8, 2009.

* cited by examiner

*Primary Examiner* — John Mabry
(74) *Attorney, Agent, or Firm* — Sterne, Kessler, Goldstein & Fox P.L.L.C.

(57) ABSTRACT

The use of thiazole-4-carboxylic esters and thioesters of the formula (I)

(I)

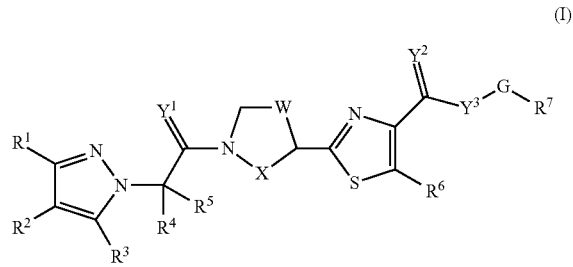

in which
$R^1, R^2, R^3, R^4, R^5, R^6, R^7, Y^1, Y^2, Y^3, W, X$ and G have the meanings given in the description, and also of agrochemically active salts thereof, as fungicides.

7 Claims, No Drawings

THIAZOLE-4-CARBOXYLIC ACID ESTERS AND THIOESTERS AS PLANT PROTECTION AGENTS

The invention relates to thiazole-4-carboxylic esters and thioesters or agrochemically active salts thereof, to their use and to methods and compositions for controlling phytopathogenic harmful fungi in and/or on plants or in and/or on seed of plants, to processes for preparing such compositions and to treated seed, and to their use for controlling phytopathogenic harmful fungi in agriculture, horticulture and forestry, in animal health, in the protection of materials and in the domestic and hygiene field. The present invention furthermore relates to a process for preparing thiazole-4-carboxylic esters and thioesters.

It is already known that certain piperidinyl-substituted thiazole-4-carboxamides can be used as fungicidal crop protection agents (see WO 07/014,290, WO08/091,594). However, in particular at relatively low application rates, the fungicidal activity of these compounds is not always sufficient. Furthermore, in many cases the activity spectrum of these amides is insufficient. Moreover, some carboxylic esters are described as intermediates; however, a biological activity is not described.

WO 04/058751 describes piperidinyl-substituted thiazole-4-carboxylic esters and thioesters which can be used as pharmaceutics for modulating blood pressure.

WO 05/003128 describes further piperidinyl-substituted thiazole-4-carboxylic esters and thioesters which are likewise suitable for medicinal applications, here as inhibitors on the microsomal triglyceride transfer protein (MTP inhibitors). However, an effect on fungal pathogens is not described.

Since the ecological and economical demands made on modern crop protection agents are increasing constantly, for example with respect to activity spectrum, toxicity, selectivity, application rate, formation of residues and favorable manufacture, and there can furthermore be problems, for example, with resistances, there is a constant need to develop novel crop protection agents which, at least in some areas, have advantages over the known ones.

Surprisingly, it has now been found that the present thiazole-4-carboxylic esters and thioesters achieve at least some aspects of the objects mentioned and are suitable for use as crop protection agents, in particular as fungicides.

The invention relates to compounds of the formulas (I)

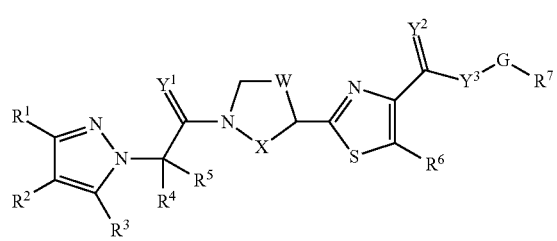

(I)

in which the symbols have the following meanings:

$R^1$ and $R^3$ independently of one another are H, $C_1$-$C_4$-alkyl, $C_2$-$C_4$-alkenyl, $C_2$-$C_4$-alkynyl, $C_3$-$C_6$-cycloalkyl, $C_3$-$C_6$-halocycloalkyl, optionally substituted phenyl, $C_1$-$C_4$-alkoxy, $C_1$-$C_4$-haloalkyl, $C_1$-$C_4$-haloalkoxy, ($C_1$-$C_4$-alkyl)carbonyl, formyl, $CR^8$=$NOR^9$, $CONR^{10}R^{11}$, ($C_1$-$C_4$-alkoxy)carbonyl, COOH, halogen, hydroxyl or cyano $R^2$ is H, substituted or unsubstituted phenyl, $C_1$-$C_4$-alkyl, $C_2$-$C_4$-alkenyl, $C_2$-$C_4$-alkynyl, $C_3$-$C_6$-cycloalkyl, $C_3$-$C_6$-halocycloalkyl, $C_1$-$C_4$-alkoxy, $C_1$-$C_4$-haloalkyl, $C_1$-$C_4$-haloalkoxy, ($C_1$-$C_4$-alkyl)carbonyl, formyl, $CR^8$=$NOR^9$, $CONR^{10}R^{11}$, ($C_1$-$C_4$-alkoxy)carbonyl, COOH, halogen, hydroxyl, cyano, nitro or $NR^{10}R^{11}$ or $R^1$ and $R^2$ or $R^2$ and $R^3$ together with the carbon atoms to which they are attached form a 5- to 7-membered unsubstituted or substituted, partially saturated or unsaturated cycle which may contain up to three further heteroatoms selected from the group consisting of N, O and S, where two oxygen atoms are not adjacent, possible substituents independently of one another being selected from the group consisting of $C_1$-$C_4$-alkyl, $C_1$-$C_4$-alkoxy, oxo, hydroxyl and halogen $R^4$ and $R^5$ independently of one another are H, $C_1$-$C_4$-alkyl, $C_3$-$C_6$-cycloalkyl or $C_1$-$C_4$-haloalkyl, or $R^4$ and $R^5$ together with the carbon atom to which they are attached form a 3- to 7-membered unsubstituted or substituted saturated cycle which may contain up to three heteroatoms selected from the group consisting of N, O and S, where two oxygen atoms are not adjacent, possible substituents independently of one another being selected from the group consisting of $C_1$-$C_4$-alkyl, $C_1$-$C_4$-alkoxy, oxo, hydroxyl, halogen $Y^1, Y^2, Y^3$ independently of one another are sulfur or oxygen X is a direct bond or an unsubstituted or substituted $C_1$- to $C_3$-carbon chain, where the carbon atoms carry, independently of one another, H, $C_1$-$C_4$-alkyl or oxo as substituents W is an unsubstituted or substituted $C_1$- to $C_3$-carbon chain, where the carbon atoms carry, independently of one another, H, $C_1$-$C_4$-alkyl or oxo as substituents $R^6$ is H, $C_1$-$C_4$-alkyl, $C_1$-$C_4$-haloalkyl, ($C_1$-$C_4$-alkyl)carbonyl, formyl, $CR^8$=$NOR^9$, $CONR^{10}R^{11}$, ($C_1$-$C_4$-alkoxy)carbonyl, COOH, $NR^{10}R^{11}$, nitro, halogen or cyano G is $(C(R^{12})_2)_m$ where m=0 to 6

$R^7$ is unsubstituted or substituted $C_5$-$C_{10}$-alkyl, $C_2$-$C_{16}$-alkenyl, $C_2$-$C_{16}$-alkynyl, $C_3$-$C_{15}$-cycloalkyl, $C_5$-$C_{15}$-cycloalkenyl, $C_3$-$C_{15}$-heterocyclyl, aryl, hetaryl or $Si(C_1$-$C_4$-alkyl)$_3$, possible substituents independently of one another being selected from the list below:

halogen, cyano, nitro, nitroso, $C_1$-$C_4$-haloalkyl, arylalkyl, arylhaloalkyl, hydroxyl, oxo, $C_1$-$C_4$-alkoxy, O($C_1$-$C_6$-alkyl)$_m$O$C_1$-$C_6$-alkyl, O—$C_3$-$C_6$-cycloalkyl, O-phenyl, $C_1$-$C_4$-haloalkoxy, SH, $C_1$-$C_6$-thioalkyl, $C_1$-$C_6$-thiohaloalkyl, S-phenyl, SO$_2$—$C_1$-$C_6$-alkyl, SO$_2$—$C_1$-$C_6$-haloalkyl, SO—$C_1$-$C_6$-alkyl, SO—$C_1$-$C_6$-haloalkyl, CO$_2$H, ($C_1$-$C_4$-alkyl)carbonyl, ($C_1$-$C_4$-haloalkyl)carbonyl, formyl, $CR^8$=$NOR^9$, $CONR^{10}R^{11}$, ($C_1$-$C_4$-alkoxy)carbonyl, COOH, $NR^{10}R^{11}$, cyclopropylamino, $CH_2COCH_3$, $(CH_2)_mO$—$C_1$-$C_6$-alkyl, $CH_2OH$, $CH_2SMe$, $(CH_2)_2SMe$, $C_3$-$C_6$-cycloalkyl, 1-methoxycyclopropyl, 1-chlorocyclopropyl, cyclohexylmethyl, $C_2$-$C_6$-alkenyl, $C_2$-$C_6$-alkynyl, $Si(C_1$-$C_4$-alkyl)$_3$, phenyl or benzyl or two adjacent substituents form an optionally methyl- or halogen-substituted dioxolane or dioxane ring, $R^8, R^9, R^{10}, R^{11}$ independently of one another are H, $C_1$-$C_4$-alkyl or $C_3$-$C_6$-cycloalkyl, or $R^{10}$ and $R^{11}$ together with the nitrogen atom to which they are attached form a 3- to 7-membered unsubstituted or substituted saturated cycle which may contain up to two further heteroatoms selected from the group consisting of N, O and S, where two oxygen atoms are not adjacent, possible substituents independently of one another being selected from the group consisting of $C_1$-$C_4$-alkyl, $C_1$-$C_4$-alkoxy, halogen and oxo $R^{12}$ is identical or different independently of one another H, halogen, $C_1$-$C_4$-alkyl, $C_1$-$C_4$-alkoxy, $C_3$-$C_6$-cycloalkyl or $C_1$-$C_4$-haloalkyl, or two or four $R^{12}$, in each case on two adjacent carbon atoms, are direct bonds, and also agrochemically active salts thereof.

The thiazole-4-carboxylic esters and thioesters of the formula (I) according to the invention and their agrochemically active salts are highly suitable for controlling phytopathogenic harmful fungi. The compounds according to the invention mentioned above have potent fungicidal activity and can be used both in crop protection, in the domestic and hygiene field and in the protection of materials.

The compounds of the formula (I) can be present both in pure form and as mixtures of various possible isomeric forms, in particular of stereoisomers, such as E and Z, threo and erythro, endo or exo, and also optical isomers, such as R and S isomers or atropisomers, and, if appropriate, also of tautomers. What is claimed are both the E and the Z isomers, and also the threo and erythro, and also the optical isomers, any mixtures of these isomers, and also the possible tautomeric forms.

Preference is given to compounds of the formula (I) in which one or more of the symbols have one of the meanings below:

$R^1$ and $R^3$ independently of one another are H, $C_1$-$C_4$ alkyl $C_3$-$C_6$-cycloalkyl, $C_1$-$C_3$-alkoxy, $C_1$-$C_3$-haloalkyl, $C_1$-$C_3$-haloalkoxy, halogen, hydroxyl, cyano or phenyl, $R^2$ is H, phenyl, $C_1$-$C_4$-alkyl, $C_2$-$C_4$-alkenyl, $C_2$-$C_4$-alkynyl, $C_3$-$C_6$-cycloalkyl, $C_1$-$C_3$-alkoxy, $C_1$-$C_3$-haloalkyl, $C_1$-$C_3$-haloalkoxy, halogen, hydroxyl, cyano or $NR^{10}R^{11}$, or $R^1$ and $R^2$ together with the carbon atoms to which they are attached form a phenyl ring, $R^4$ and $R^5$ independently of one another are H, $C_1$-$C_3$-alkyl, cyclopropyl, cyclopentyl, cyclohexyl, or $C_1$-$C_3$-haloalkyl, or $R^4$ and $R^5$ together with the carbon atom to which they are attached form a cyclopropyl ring, $Y^1$ and $Y^2$ are oxygen, $Y^3$ is sulfur or oxygen, X is a direct bond, $CH_2$ or $CH_2CH_2$, W is $CH_2$, $CH_2CH_2$ or $CH_2CH_2CH_2$, $R^6$ is H, $C_1$-$C_3$-alkyl, $C_1$-$C_3$-haloalkyl, $NH_2$, NHMe, $NMe_2$, chlorine, fluorine or cyano, G is $(C(R_{12})_2)_m$ where m=0 to 4

$R^7$ is unsubstituted or substituted $C_5$-$C_{10}$-alkyl, $C_2$-$C_{16}$-alkenyl, $C_2$-$C_{16}$-alkynyl, $C_3$-$C_{15}$-cycloalkyl, $C_5$-$C_{15}$-cycloalkenyl, $C_3$-$C_{15}$-heterocyclyl, aryl, hetaryl or $Si(C_1$-$C_4$-alkyl$)_3$, possible substituents independently of one another being selected from the list below:

fluorine, chlorine, bromine, iodine, cyano, nitro, $CF_3$, $CFH_2$, $CF_2H$, $C_2F_5$, $CCl_3$, hydroxyl, OMe, OEt, OPr, OisoPr, OBu, OsecBu, OisoBu, OtertBu, $O(CH_2)_2OCH_3$, $O(CH_2)_3OCH_3$, O-cyclohexyl, O-cyclopentyl, O-cyclopropyl, O-phenyl, $OCF_3$, $OCF_2H$, $OCH_2CF_3$, $OCF_2CF_3$, SH, SMe, SEt, $SCF_3$, $SCF_2H$, S-phenyl, $SO_2Me$, $SO_2CF_3$, SOMe, SOEt, $CO_2H$, $CO_2CH_3$, $CO_2Et$, $CO_2Pr$, $CO_2isoPr$, $CO_2tertBu$, COMe, $COCF_3$, $NH_2$, NHMe, $NMe_2$, NHEt, $NEt_2$, NHPr, NHisoPr, NHnBu, NHtertBu, NHisoBu, NHsecBu, cyclopropylamino, morpholinyl, piperidinyl, piperazinyl, pyrrolidinyl, aziridinyl, azetidinyl, formyl, $CH_2COCH_3$, $CH_2OMe$, $(CH_2)_2OMe$, $(CH_2)_3OMe$, $CH_2OH$, $CH_2SMe$, $(CH_2)_2SMe$, methyl, ethyl, propyl, 1-methylethyl, butyl, 1-methylpropyl, 2-methylpropyl, 1,1-dimethylethyl, 1-methoxycyclopropyl, 1-chlorocyclopropyl, cyclopropyl, cyclobutyl, cyclopentyl, cyclohexyl, cyclohexylmethyl, prop-2-en-1-yl, 1-methylprop-2-en-1-yl, but-3-en-1-yl, trimethylsilyl)methyl, phenyl, benzyl, —CH═CH$_2$, —CH$_2$CH═CH$_2$, —CH(CH$_3$)CH═CH$_2$, —CH$_2$C≡CH, —C≡CH, or two adjacent substituents form an optionally methyl- or halogen-substituted dioxolane or dioxane ring, $R^{10}$, $R^{11}$ independently of one another are H, methyl, ethyl, isopropyl or cyclopropyl, or $R^{10}$ and $R^{11}$ together with the nitrogen atom to which they are attached form an aziridinyl, azetidinyl, pyrrolidinyl, piperidinyl or morpholinyl ring, $R^{12}$ is identical or different independently of one another H, methyl, ethyl, chlorine, fluorine, trifluoromethyl, methoxy or cyclopropyl, or two or four $R^{12}$, in each case on two adjacent carbon atoms, are direct bonds, and the agrochemically active salts thereof.

Particular preference is given to compounds of the formula (I) in which one or more of the symbols have one of the meanings below:

$R^1$ is $C_1$-$C_2$-alkyl or $C_1$-$C_2$-haloalkyl, $R^2$ is H, $C_1$-$C_2$-haloalkyl or halogen, or $R^1$ and $R^2$ together with the carbon atoms to which they are attached form a phenyl ring, $R^3$ is H, $C_1$-$C_2$-alkyl, $C_1$-$C_2$-haloalkyl or phenyl, $R^4$ is H, $C_1$-$C_2$-alkyl or $C_1$-$C_2$-haloalkyl, $R^5$ is H, $C_1$-$C_2$-alkyl, $C_1$-$C_2$-haloalkyl or cyclopropyl, or $R^4$ and $R^5$ together with the carbon atom to which they are attached form a cyclopropyl ring, $Y^1$ is oxygen, $Y^2$ is oxygen, $Y^3$ is sulfur or oxygen, X is $CH_2$ or $CH_2CH_2$, W is $CH_2$, $CH_2CH_2$ or $CH_2CH_2CH_2$, $R^6$ is H or methyl, G is $(C(R^{12})_2)$, where m=0 to 4

$R^7$ is unsubstituted or substituted $C_5$-$C_{10}$-alkyl, $C_2$-$C_{16}$-alkenyl, $C_2$-$C_{16}$-alkynyl, $C_3$-$C_{15}$-cycloalkyl, $C_5$-$C_{15}$-cycloalkenyl, $C_3$-$C_{15}$-heterocyclyl, aryl, hetaryl or $Si(C_1$-$C_4$-alkyl$)_3$, possible substituents independently of one another being selected from the list below:

fluorine, chlorine, bromine, iodine, cyano, nitro, $CF_3$, hydroxyl, OMe, O-phenyl, $OCF_3$, $OCF_2H$, $OCH_2CF_3$, $OCF_2CF_3$, SMe, S-phenyl, methyl, ethyl, propyl, 1-methylethyl, butyl, 1-methylpropyl, 2-methylpropyl, 1,1-dimethylethyl, phenyl, benzyl, —CH═CH$_2$, —CH$_2$CH═CH$_2$ or —C≡CH, $R^{12}$ is identical or different independently of one another H, methyl or ethyl, and the agrochemically active salts thereof.

Very particular preference is given to compounds of the formula (I) in which one or more of the symbols have one of the meanings below:
$R^1$ is methyl, ethyl, 1-methylethyl, 1,1-dimethylethyl, difluoromethyl, trifluoromethyl or pentafluoroethyl,
$R^2$ is H or chlorine,
or
$R^1$ and $R^2$ together with the carbon atoms to which they are attached form a phenyl ring,
$R^3$ is H, methyl, 1,1-dimethylethyl, difluoromethyl, trifluoromethyl, pentafluoroethyl or phenyl,
$R^4$ is H or methyl,
$R^5$ is H, methyl or cyclopropyl,
or
$R^4$ and $R^5$ together with the carbon atom to which they are attached form a cyclopropyl ring,
$Y^1$ is oxygen,
$Y^2$ is oxygen,
$Y^3$ is sulfur or oxygen,
X is $CH_2$ or $CH_2CH_2$,
W is $CH_2$, $CH_2CH_2$ or $CH_2CH_2CH_2$,
$R^6$ is H or methyl,
G is a direct bond, $CH_2$, $CH_2CH_2$, $CH(CH_3)$, $CH(CH_2CH_3)$ or $CH(CF_3)$,
$R^7$ is methyl, tert-butyl, heptan-3-yl, octyl, (1Z)-prop-1-en-1-yl, (E)-2-phenylethenyl, hex-1-en-3-yl, diphenylmethyl, 1,2,3,4-tetrahydronaphthalen-1-yl, (1R)-1,2,3,4-tetrahydronaphthalen-1-yl, (1S)-1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decahydronaphthalen-1-yl, 1,4-dioxaspiro[4.5]dec-8-yl, 2,3-dihydro-1H-inden-1-yl, 2,3-dihydro-1H-inden-2-yl, cyclopropyl, 2,2-dichlorocyclopropyl, cyclopentyl, 1-ethynylcyclopentyl, cyclohexyl, 2-methylcyclohexyl, 2,6-dimethylcyclohexyl, 4-tert-butylcyclohexyl, 5-methyl-2-(propan-2-yl)cyclohexyl, 3-methyl-5-(propan-2-yl)cyclohexyl, 1-cyanocyclohexyl, 1-ethynylcyclohexyl, cycloheptyl, cyclopropyl(phenyl)methyl, (1S,2R)-1,7,7-trimethylbicyclo[2.2.1]hept-2-yl, phenyl, 4-fluorophenyl, 2-bromophenyl, 2-chlorophenyl, 3-chlorophenyl, 4-chlorophenyl, 2,4-dichlorophenyl, 2,6-dichlorophenyl, 3,4-dichlorophenyl, 3,5-dichlorophenyl, 2,4,6-trichlorophenyl, 2,4,6-trifluorophenyl, 2-methoxyphenyl, 4-methoxyphenyl, 2,4-dimethoxyphenyl, 2,6-dimethoxyphenyl, 2-methylphenyl, 3-methylphenyl, 4-methylphenyl, 4-nitrophenyl, 2-(trifluoromethyl)phenyl, 3-(trifluoromethyl)phenyl, 4-(trifluoromethyl)phenyl, 2-(trifluoromethoxy)phenyl, 4-(trifluoromethoxy)phenyl, 4-tert-butylphenyl, biphenyl-2-yl, biphenyl-3-yl, biphenyl-4-yl, 3-phenoxyphenyl, 4-phenoxyphenyl, 2-[1-methoxy-2-(methylamino)-2-oxoethyl]phenyl, 2-[(methylamino)(oxo)acetyl]phenyl 1-naphthyl, 2-naphthyl, phenylethynyl, 2-thienyl, pyridin-2-yl, pyridin-3-yl, pyridin-4-yl, quinolin-5-yl, quinolin-6-yl, quinolin-7-yl, quinolin-8-yl, isoquinolin-5-yl, 1,3-benzoxazol-4-yl, trifluoromethyl, morpholin-4-yl, piperidin-1-yl, pyrrolidin-1-yl, 4-methylpiperazin-1-yl, dimethylamino or trimethylsilyl, and the agrochemically active salts thereof.

Most preference is given to compounds of the formula (I) in which one or more of the symbols have one of the meanings below:
$R^1$ is methyl, ethyl, 1-methylethyl, 1,1-dimethylethyl, difluoromethyl, trifluoromethyl or pentafluoroethyl,
$R^2$ is H or chlorine,
$R^3$ is H, methyl, 1,1-dimethylethyl, difluoromethyl, trifluoromethyl, pentafluoroethyl or phenyl,
$R^4$ is H or methyl,
$R^5$ is H or methyl,
$Y^1$ is oxygen,
$Y^2$ is oxygen,
$Y^3$ is sulfur or oxygen,
X is $CH_2$ or $CH_2CH_2$,
W is $CH_2$ or $CH_2CH_2$,
$R^6$ is H,
G is a direct bond, $CH_2$, $CH_2CH_2$, $CH(CH_3)$ or $CH(CH_2CH_3)$,
$R^7$ is heptan-3-yl, octyl, (1Z)-prop-1-en-1-yl, (E)-2-phenylethenyl, hex-1-en-3-yl, diphenylmethyl, 1,2,3,4-tetrahydronaphthalen-1-yl, (1R)-1,2,3,4-tetrahydronaphthalen-1-yl, (1S)-1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decahydronaphthalen-1-yl, 1,4-dioxaspiro[4.5]dec-8-yl, 2,3-dihydro-1H-inden-1-yl, 2,3-dihydro-1H-inden-2-yl, cyclopropyl, cyclopentyl, 1-ethynylcyclopentyl, cyclohexyl, 2-methylcyclohexyl, 2,6-dimethylcyclohexyl, 4-tert-butylcyclohexyl, 5-methyl-2-(propan-2-yl)cyclohexyl, 3-methyl-5-(propan-2-yl)cyclohexyl, 1-cyanocyclohexyl, 1-ethynylcyclohexyl, cycloheptyl, cyclopropyl(phenyl)methyl, (1S,2R)-1,7,7-trimethylbicyclo[2.2.1]hept-2-yl, phenyl, 2-chlorophenyl, 3-chlorophenyl, 4-chlorophenyl, 2,4-dichlorophenyl, 2,6-dichlorophenyl, 3,4-dichlorophenyl, 3,5-dichlorophenyl, 2,4,6-trichlorophenyl, 2,4,6-trifluorophenyl, 2-methoxyphenyl, 4-methoxyphenyl, 2,4-dimethoxyphenyl, 2,6-dimethoxyphenyl, 2-methylphenyl, 3-methylphenyl, 4-methylphenyl, 4-nitrophenyl, 2-(trifluoromethyl)phenyl, 3-(trifluoromethyl)phenyl, 4-(trifluoromethyl)phenyl, 2-(trifluoromethoxy)phenyl, 4-(trifluoromethoxy)phenyl, 4-tert-butylphenyl, biphenyl-2-yl, biphenyl-3-yl, biphenyl-4-yl, 3-phenoxyphenyl, 4-phenoxyphenyl, 1-naphthyl, 2-naphthyl, phenylethynyl, 2-thienyl, pyridin-2-yl, pyridin-3-yl, pyridin-4-yl, quinolin-5-yl, quinolin-6-yl, quinolin-7-yl, quinolin-8-yl, isoquinolin-5-yl, 1,3-benzoxazol-4-yl, trifluoromethyl, dimethylamino or trimethylsilyl,
and the agrochemically active salts thereof.

Special preference is furthermore given to compounds of the formula (I) in which one or more of the symbols have one of the meanings below:
$R^1$ is $C_1$-$C_4$-alkyl or $C_1$-$C_2$-haloalkyl,
$R^2$ is H and
$R^3$ is $C_1$-$C_4$-alkyl or $C_1$-$C_2$-haloalkyl,
where the other substituents have one or more of the meanings mentioned above,
and the agrochemically active salts thereof.

Special preference is furthermore given to compounds of the formula (I) in which one or more of the symbols have one of the meanings below:
$R^1$ is methyl, ethyl, 1-methylethyl, 1,1-dimethylethyl, difluoromethyl, trifluoromethyl or pentafluoroethyl,
$R^2$ is H and
$R^3$ is methyl, 1,1-dimethylethyl, difluoromethyl, trifluoromethyl, pentafluoroethyl or phenyl,
where the other substituents have one or more of the meanings mentioned above, and the agrochemically active salts thereof.

Special preference is furthermore given to compounds of the formula (I) in which one or more of the symbols have one of the meanings below:
X is $CH_2CH_2$ and
W is $CH_2$,
where the other substituents have one or more of the meanings mentioned above, and the agrochemically active salts thereof.

Special preference is furthermore given to compounds of the formula (I) in which
Y³ is oxygen,
where the other substituents have one or more of the meanings mentioned above, and the agrochemically active salts thereof.

Special preference is furthermore given to compounds of the formula (I) in which
R⁶ is H,
where the other substituents have one or more of the meanings mentioned above, and the agrochemically active salts thereof.

Special preference is furthermore given to compounds of the formula (I) in which
G is $CH_2$, $CH_2CH_2$, $CH(CH_3)$ or $CH(CH_2CH_3)$,
where the other substituents have one or more of the meanings mentioned above, and the agrochemically active salts thereof.

Special preference is furthermore given to compounds of the formula (I) in which
R⁷ is $C_5$-$C_{10}$-alkyl,
where the other substituents have one or more of the meanings mentioned above, and the agrochemically active salts thereof.

Special preference is furthermore given to compounds of the formula (I) in which
R⁷ is $C_5$-$C_8$-alkyl,
where the other substituents have one or more of the meanings mentioned above, and the agrochemically active salts thereof.

Very particular preference is furthermore given to compounds of the formula (I) in which
R⁷ is heptan-3-yl or octyl,
where the other substituents have one or more of the meanings mentioned above, and the agrochemically active salts thereof.

Special preference is furthermore given to compounds of the formula (I) in which
R⁷ is $C_2$-$C_{16}$-alkenyl,
where the other substituents have one or more of the meanings mentioned above, and the agrochemically active salts thereof.

Special preference is furthermore given to compounds of the formula (I) in which
R⁷ is $C_2$-$C_6$-alkenyl,
where the other substituents have one or more of the meanings mentioned above, and the agrochemically active salts thereof.

Special preference is furthermore given to compounds of the formula (I) in which
R⁷ is (1Z)-prop-1-en-1-yl or hex-1-en-3-yl,
where the other substituents have one or more of the meanings mentioned above, and the agrochemically active salts thereof.

Special preference is furthermore given to compounds of the formula (I) in which
R⁷ is $C_2$-$C_{16}$-alkynyl,
where the other substituents have one or more of the meanings mentioned above, and the agrochemically active salts thereof.

Special preference is furthermore given to compounds of the formula (I) in which
R⁷ is $C_2$-$C_6$-alkynyl,
where the other substituents have one or more of the meanings mentioned above, and the agrochemically active salts thereof.

Special preference is furthermore given to compounds of the formula (I) in which
R⁷ is $C_3$-$C_{15}$-cycloalkyl,
where the other substituents have one or more of the meanings mentioned above, and the agrochemically active salts thereof.

Special preference is furthermore given to compounds of the formula (I) in which
R⁷ is $C_3$-$C_8$-cycloalkyl,
where the other substituents have one or more of the meanings mentioned above, and the agrochemically active salts thereof.

Special preference is furthermore given to compounds of the formula (I) in which
R⁷ is cyclopropyl, cyclopentyl, cyclohexyl or cycloheptyl,
where the other substituents have one or more of the meanings mentioned above, and the agrochemically active salts thereof.

Special preference is furthermore given to compounds of the formula (I) in which
R⁷ is $C_5$-$C_{15}$-cycloalkenyl,
where the other substituents have one or more of the meanings mentioned above, and the agrochemically active salts thereof.

Special preference is furthermore given to compounds of the formula (I) in which
R⁷ is $C_5$-$C_8$-cycloalkenyl,
where the other substituents have one or more of the meanings mentioned above, and the agrochemically active salts thereof.

Special preference is furthermore given to compounds of the formula (I) in which
R⁷ is $C_3$-$C_{15}$-heterocyclyl,
where the other substituents have one or more of the meanings mentioned above, and the agrochemically active salts thereof.

Special preference is furthermore given to compounds of the formula (I) in which
R⁷ is $C_5$-$C_6$-heterocyclyl,
where the other substituents have one or more of the meanings mentioned above, and the agrochemically active salts thereof.

Special preference is furthermore given to compounds of the formula (I) in which
R⁷ is aryl,
where the other substituents have one or more of the meanings mentioned above, and the agrochemically active salts thereof.

Special preference is furthermore given to compounds of the formula (I) in which
R⁷ is phenyl, or saturated or partially or fully unsaturated unsubstituted or substituted naphthyl or indenyl,
where the other substituents have one or more of the meanings mentioned above, and the agrochemically active salts thereof.

Special preference is furthermore given to compounds of the formula (I) in which
R⁷ is phenyl, 1-naphthyl, 2-naphthyl, 1,2,3,4-tetrahydronaphthalen-1-yl, (1R)-1,2,3,4-tetrahydronaphthalen-1-yl, (1S)-1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decahydronaphthalen-1-yl, 2,3-dihydro-1H-inden-1-yl or 2,3-dihydro-1H-inden-2-yl,
where the other substituents have one or more of the meanings mentioned above, and the agrochemically active salts thereof.

Special preference is furthermore given to compounds of the formula (I) in which $R^7$ is hetaryl, where the other substituents have one or more of the meanings mentioned above, and the agrochemically active salts thereof.

Special preference is furthermore given to compounds of the formula (I) in which $R^7$ is furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl, where the other substituents have one or more of the meanings mentioned above, and the agrochemically active salts thereof.

Special preference is furthermore given to compounds of the formula (I) in which $R^7$ is pyridin-2-yl, pyridin-3-yl, pyridin-4-yl, quinolin-5-yl, quinolin-6-yl, quinolin-7-yl, quinolin-8-yl, isoquinolin-5-yl or 1,3-benzoxazol-4-yl, where the other substituents have one or more of the meanings mentioned above, and the agrochemically active salts thereof.

Special preference is furthermore given to compounds of the formula (I) in which $R^7$ is $Si(C_1-C_4-alkyl)_3$, where the other substituents have one or more of the meanings mentioned above, and the agrochemically active salts thereof.

Special preference is furthermore given to compounds of the formula (I) in which $R^7$ is $Si(C_1-C_2-alkyl)_3$, where the other substituents have one or more of the meanings mentioned above, and the agrochemically active salts thereof.

Special preference is furthermore given to compounds of the formula (I) in which $R^7$ is trimethylsilyl, where the other substituents have one or more of the meanings mentioned above, and the agrochemically active salts thereof.

Depending on the nature of the substituents defined above, the compounds of the formula (I) have acidic or basic properties and can form salts, if appropriate also inner salts, or adducts with inorganic or organic acids or with bases or with metal ions. If the compounds of the formula (I) carry amino, alkylamino or other groups which induce basic properties, these compounds can be reacted with acids to give salts, or they are directly obtained as salts in the synthesis. If the compounds of the formula (I) carry hydroxyl, carboxyl or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having $(C_1-C_4)$-alkyl groups, mono-, di- and trialkanolamines of $(C_1-C_4)$-alkanols, choline and also chlorocholine.

The salts obtainable in this manner also have fungicidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as $NaHSO_4$ and $KHSO_4$. Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulphonic acids (sulphonic acids having straight-chain or branched alkyl radicals of 1 to 20 carbon atoms), arylsulphonic acids or aryldisulphonic acids (aromatic radicals, such as phenyl and naphthyl, which carry one or two sulphonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), where the alkyl and aryl radicals may carry further substituents, for example p-toluenesulphonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminum, tin and lead, and also of the first to eighth transition group, in particular chromium, manganese, iron, cobalt, nickel, copper, zinc and others. Particular preference is given to the metal ions of the elements of the fourth period. Here, the metals can be present in various valencies that they can assume.

Optionally substituted groups can be mono- or polysubstituted, where in the case of polysubstitutions the substituents can be identical or different.

In the definitions of the symbols given in the formulae above, collective terms were used which are generally representative of the following substituents:

halogen: fluorine, chlorine, bromine and iodine;

aryl: unsubstituted or optionally substituted 5- to 15-membered partially or fully unsaturated mono-, bi- or tricyclic ring system having up to 3 ring members selected from the groups $C(=O)$, $(C=S)$, where at least one of the rings of the ring system is fully unsaturated, such as, for example (but not limited to), benzene, naphthalene, tetrahydronaphthalene, anthracene, indane, phenanthrene, azulene;

alkyl: saturated, straight-chain or branched hydrocarbon radicals having 1 to 10 carbon atoms, for example (but not limited thereto) methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, heptyl, 1-methylhexyl, octyl, 1,1-dimethylhexyl, 2-ethylhexyl, 1-ethylhexyl, nonyl, 1,2,2-trimethylhexyl, decyl;

haloalkyl: straight-chain or branched alkyl groups having 1 to 4 carbon atoms (as mentioned above), where in these groups some or all of the hydrogen atoms may be replaced by halogen atoms as mentioned above, for example (but not limited thereto) $C_1$-$C_2$-haloalkyl, such as chloro-methyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl;

alkenyl: unsaturated, straight-chain or branched hydrocarbon radicals having 2 to 16 carbon atoms and at least one double bond in any position, for example (but not limited thereto) $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 16 carbon atoms and at least one triple bond in any position, for example (but not limited thereto) $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

alkoxy: saturated, straight-chain or branched alkoxy radicals having 1 to 4 carbon atoms, for example (but not limited thereto) $C_1$-$C_4$-alkoxy, such as methoxy, ethoxy, propoxy, 1-methylethoxy, butoxy, 1-methylpropoxy, 2-methylpropoxy, 1,1-dimethylethoxy;

haloalkoxy: straight-chain or branched alkoxy groups having 1 to 4 carbon atoms (as mentioned above), where in these groups some or all of the hydrogen atoms may be replaced by halogen atoms as mentioned above, for example (but not limited thereto) $C_1$-$C_2$-haloalkoxy, such as chloro-methoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy;

thioalkyl: saturated, straight-chain or branched alkylthio radicals having 1 to 6 carbon atoms, for example (but not limited thereto) $C_1$-$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

thiohaloalkyl: straight-chain or branched alkylthio groups having 1 to 6 carbon atoms (as mentioned above), where in these groups some or all of the hydrogen atoms may be replaced by halogen atoms as mentioned above, for example (but not limited thereto) $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio;

cycloalkyl: mono-, bi- or tricyclic saturated hydrocarbon groups having 3 to 12 carbon ring members, for example (but not limited thereto) cyclopropyl, cyclobutyl, cyclopentyl and cyclohexyl, bicyclo[1.0.1]butane, decalinyl, norbornyl;

cycloalkenyl: mono-, bi- or tricyclic non-aromatic hydrocarbon groups having 5 to 15 carbon ring members and at least one double bond, for example (but not limited thereto) cyclopenten-1-yl, cyclohexen-1-yl, cyclohepta-1,3-dien-1-yl, norbornen-1-yl;

(alkoxy)carbonyl: an alkoxy group having 1 to 4 carbon atoms (as mentioned above) which is attached to the skeleton via a carbonyl group (—CO—);

heterocyclyl: a three- to fifteen-membered saturated or partially unsaturated heterocycle which contains one to four heteroatoms from the group consisting of oxygen, nitrogen and sulfur: mono-, bi- or tricyclic heterocycles which contain, in addition to carbon ring members, one to three nitrogen atoms and/or one oxygen or sulphur atom or one or two oxygen and/or sulphur atoms; if the ring contains a plurality of oxygen atoms, these are not directly adjacent; such as, for example (but not limited thereto), oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetra-hydropyranyl, 4-tetrahydropyranyl, 2-tetrahydrothienyl, 3-hexahydropyridazinyl, 4-hexahy-dropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

hetaryl: an unsubstituted or optionally substituted 5- to 15-membered partially or fully unsaturated mono-, bi- or tricyclic ring system where at least one of the rings of the ring system is fully unsaturated and which contains one to four heteroatoms from the group consisting of oxygen, nitrogen and sulfur; if the ring contains a plurality of oxygen atoms, these are not directly adjacent;

such as, for example (but not limited thereto)

5-membered heteroaryl which contains one to four nitrogen atoms or one to three nitrogen atoms and one sulfur or oxygen atom: 5-membered heteroaryl groups which, in addition to carbon atoms, may contain one to four nitrogen atoms or one to three nitrogen thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thia-dia-zol-5-yl, 1,2,4-triazol-3-yl, 1,3,4-oxadiazol-2-yl, 1,3,4-thiadiazol-2-yl and 1,3,4-triazol-2-yl;

benzo-fused 5-membered heteroaryl which contains one to three nitrogen atoms or one nitrogen atom and one oxygen or sulfur atom: 5-membered heteroaryl groups which, in addition to carbon atoms, may contain one to four nitrogen atoms or one to three nitrogen atoms and one sulfur or oxygen atom as ring members and in which two adjacent carbon ring members or one nitrogen and one adjacent carbon ring member may be bridged by a buta-1,3-diene-1,4-diyl group in which one or two carbon atoms may be replaced by nitrogen atoms; for example benzindolyl, benzimidazolyl, benzothiazolyl, benzopyrazolyl, benzofuryl;

5-membered heteroaryl which contains one to four nitrogen atoms and is attached via nitrogen or benzo-fused 5-membered heteroaryl which contains one to three nitrogen atoms and is attached via nitrogen: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are attached to the skeleton via one of the nitrogen ring members, for example 1-pyrrolyl, 1-pyrazolyl, 1,2,4-triazol-1-yl, 1-imidazolyl, 1,2,3-triazol-1-yl, 1,3,4-triazol-1-yl;

6-membered heteroaryl which contains one to three or one to four nitrogen atoms: 6-membered heteroaryl groups which, in addition to carbon atoms, may contain, respectively, one to three and one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

Not included are combinations which are against natural laws and which the person skilled in the art would therefore exclude based on his/her expert knowledge. Ring structures having three or more adjacent oxygen atoms, for example, are excluded.

The present invention furthermore provides a process for preparing the thiazole-4-carboxylic esters and thioesters of the formula (I) according to the invention, which comprises at least one of steps (a) to (e) below:

(a) the conversion of a compound of the formula (VII) or (IX) into a compound of the formula (VI) or (X), optionally in each case in the presence of a solvent and, if appropriate, in the presence of an acid or, if appropriate, in the presence of a base or, if appropriate, in the presence of a hydrogen source, according to the reaction scheme below (Scheme 1):

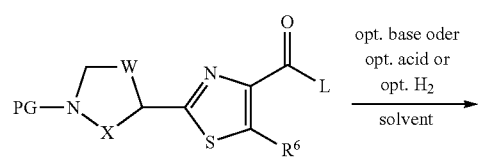

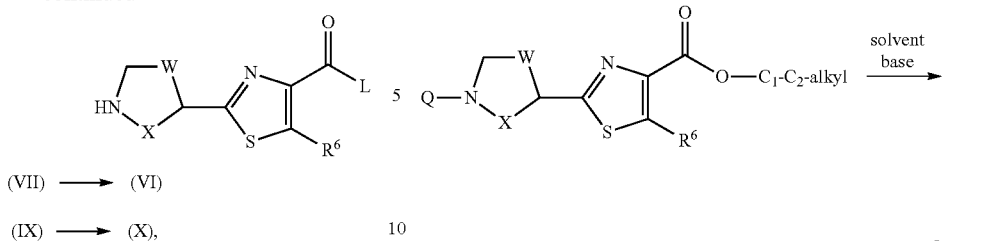

(VII) → (VI)

(IX) → (X), where

L=—O—$C_1$-$C_2$-alkyl for compounds of the formulae (VII) and (VI),

L=—$Y^3$-G-$R^7$ for compounds of the formulae (IX) and (X),

PG=acetyl, $C_1$-$C_4$-alkoxycarbonyl, benzyl or benzyloxycarbonyl,

W, X and $R^6$ are as defined above for formula (I).

(b) the reaction of a compound of the formula (VI) or (X) with a compound of the formula (V) to give a compound of the formula (IV) or (I), in each case, if appropriate, in the presence of a coupling agent, a base and a solvent, according to the reaction scheme below (Scheme 2):

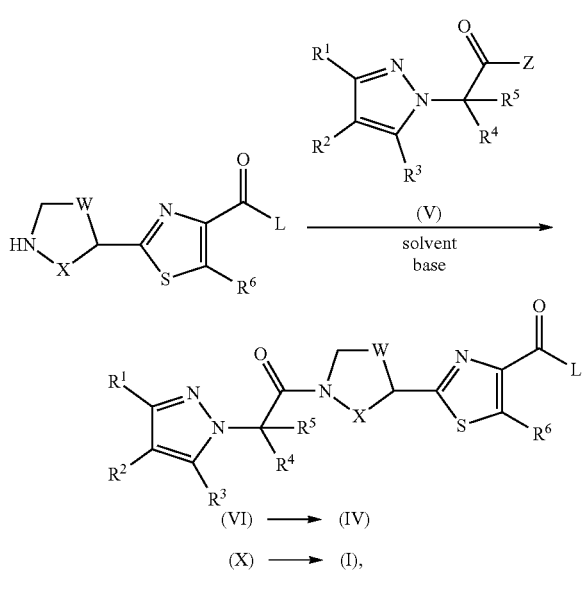

(VI) → (IV)

(X) → (I), where

Z=Cl or OH,

L=—O—$C_1$-$C_2$-alkyl for compounds of the formulae (VI) and (IV),

L=—$Y^3$-G-$R^7$ for compounds of the formulae (X) and (I),

W, X, $Y^3$, G, $R^1$, $R^2$, $R^3$, $R^4$, $R^5$, $R^6$ and $R^7$ are as defined above for formula (I).

(c) the conversion of a compound of the formula (IV) or (VII) into a compound of the formula (III) or (VIII), in each case by hydrolysis in the presence of a base and, if appropriate, in the presence of a solvent, according to the reaction scheme below (Scheme 3):

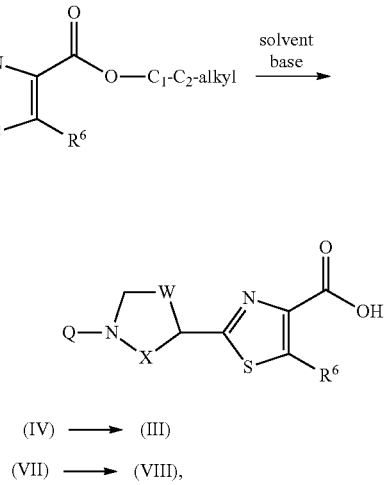

(IV) → (III)

(VII) → (VIII), where

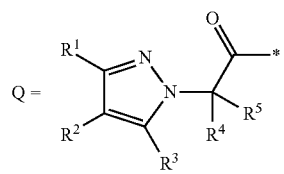

for compounds of the formulae (IV) and (III),

Q=acetyl, $C_1$-$C_4$-alkoxycarbonyl, benzyl or benzyloxycarbonyl (corresponds to PG), for compounds of the formulae (VII) and (VIII), W, X, $R^1$, $R^2$, $R^3$, $R^4$, $R^5$ and $R^6$ are as defined above for formula (I).

(d) the reaction of a compound of the formula (III) or (VIII) with a compound of the formula (II) to give a compound of the formula (I) or (IX), in each case, if appropriate, in the presence of a coupling agent, a base and a solvent, according to the reaction scheme below (Scheme 4):

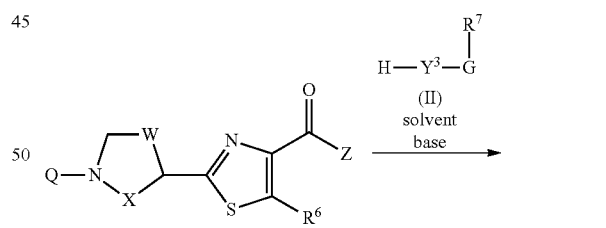

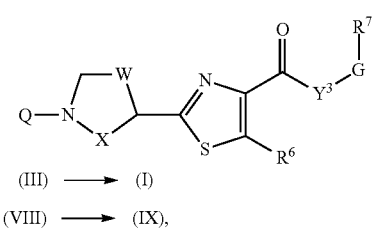

(III) → (I)

(VIII) → (IX), where

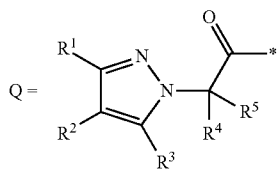

for compounds of the formulae (III) and (I),

Q=acetyl, $C_1$-$C_4$-alkoxycarbonyl, benzyl or benzyloxycarbonyl (corresponds to PG), for compounds of the formulae (VIII) and (IX), Z=OH or chlorine, W, X, $Y^3$, G, $R^1$, $R^2$, $R^3$, $R^4$, $R^5$, $R^6$ and $R^7$ are as defined above for formula (I).

(e) the conversion of a compound of the formula (I) into a compound of the formula (I) in the presence of a sulfurizing agent and, if appropriate, in the presence of a solvent, according to the reaction scheme below (Scheme 5):

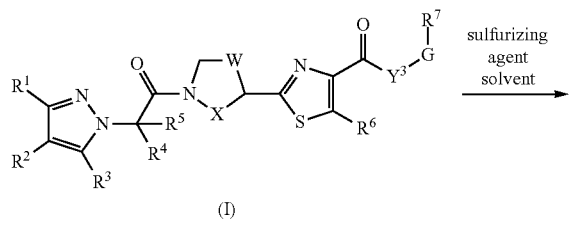

-continued

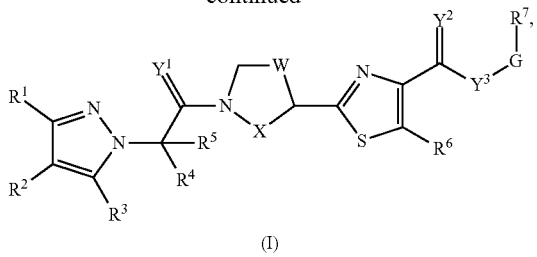

(I)

where
$Y^1$=sulfur or oxygen,
$Y^2$=sulfur or oxygen,
W, X, $Y^3$, G, $R^2$, $R^3$, $R^4$, $R^5$, $R^6$ and $R^7$ are as defined above for formula (I).

A general overview of the synthesis paths is given in Scheme 6.

The protective group is removed from compounds of the formula (VII), giving compounds of the formula (VI) or the corresponding salt (Scheme 1). A compound of the formula (VI) or a corresponding salt is coupled with a substrate of the formula (V), which gives compounds of the formula (IV) (Scheme 2). The hydrolysis of compounds of the formula (IV) leads to carboxylic acids of the formula (III) (Scheme 3), followed by a coupling reaction in the presence of an alcohol or thiol of the general formula (II), which gives compounds of the formula (I) (Scheme 4). Alternatively, the hydrolysis of the compound of the formula (VII) leads to a carboxylic acid of the general formula (VIII) (Scheme 3), followed by a coupling reaction in the presence of an alcohol or thiol of the general formula (II), which gives a compound of the formula (IX) (Scheme 4). The protective group marked PG of a compound of the formula (IX) is removed, so that a compound of the formula (X) or the corresponding salt is formed (Scheme 1). A compound of the formula (X) or a corresponding salt is coupled with a substrate of the formula (V), which gives a compound of the formula (I) (Scheme 2). A sulfurizing agent is added to a compound of the formula (I) to form a compound of the formula (I) ($Y^1$=sulfur or oxygen, $Y^2$=sulfur or oxygen) (Scheme 5).

Scheme 6
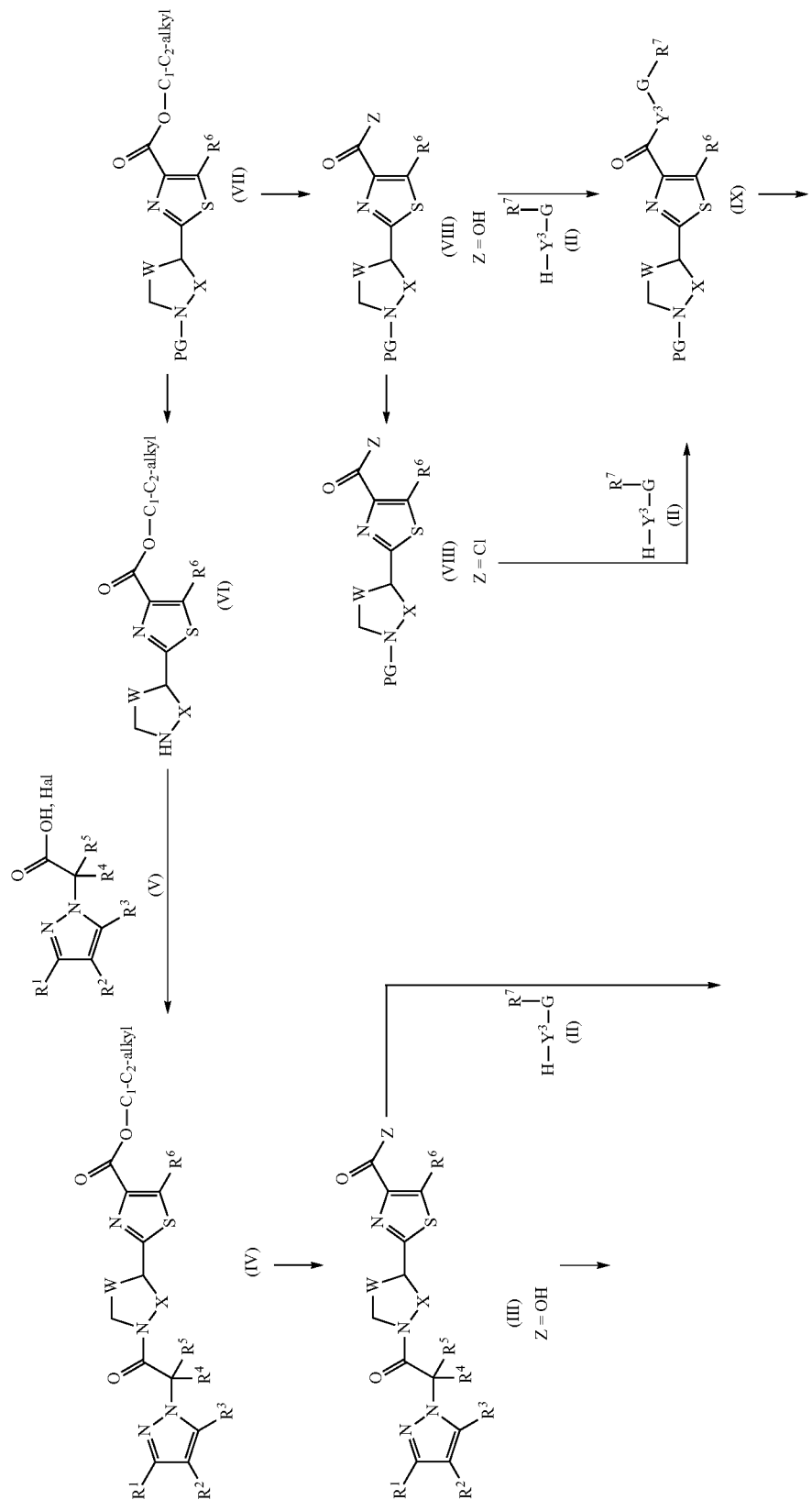

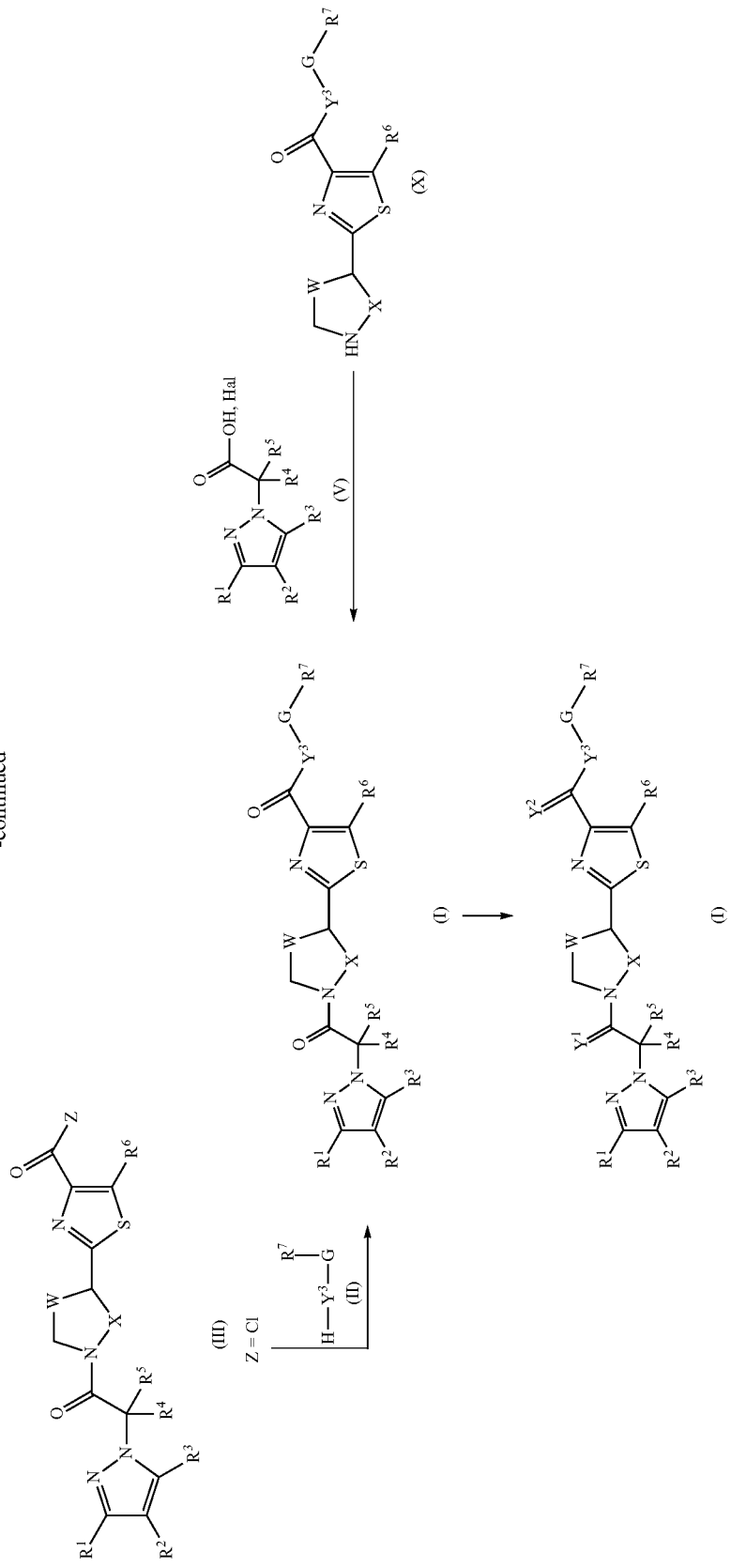

One way of preparing the intermediate (VI) from corresponding compounds (VII) is shown in Scheme 1.

A compound of the formula (VII) is converted into a compound of the formula (VI) using suitable methods for removing protective groups, which methods are described in the literature ("*Protective Groups in Organic Synthesis*"; Third Edition; Theodora W. Greene, Peter G. M. Wuts; 494-653, and the literature cited therein).

tert-Butoxycarbonyl and benzyloxycarbonyl protective groups can be removed in an acidic medium (for example using hydrochloric acid or trifluoroacetic acid). Acetyl protective groups can be removed under basic conditions (using, for example, potassium carbonate or cesium carbonate). Benzylic protective groups can be removed hydrogenolytically using hydrogen in the presence of a catalyst (for example palladium on activated carbon).

Suitable for use as solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene), nitriles (for example acetonitrile), carboxylic esters (for example ethyl acetate), amides (for example N,N-dimethylformamide, N,N-dimethylacetamide), dimethyl sulfoxide, 1,3-dimethyl-2-imidazolinone, water and acetic acid, or the reaction can be carried out in mixtures of two or more of these solvents.

Acids which can be used for this reaction of deprotecting t-butoxycarbonyl and benzyloxycarbonyl groups are, for example, trifluoroacetic acid, hydrochloric acid or other acids, as described in the literature (for example "*Protective Groups in Organic Synthesis*"; Third Edition; Theodora W. Greene, Peter G. M. Wuts; pp. 494-653).

The reaction is usually carried out at temperatures of 0° C.-150° C. and preferably at room temperature, but it can also be carried out at the reflux temperature of the reaction mixture. The reaction time varies depending on the scale of the reaction and the reaction temperature, but is generally between half an hour and 72 hours.

After the reaction has ended, the compounds (VI) are removed from the reaction mixture using one of the customary separation techniques. If required, the compounds are purified by recrystallisation, distillation or chromatography, or they can, if appropriate, also be used for the next step without prior purification. Moreover, it is possible to isolate the compound of the general formula (VI) as a salt, for example as a salt of hydrochloric acid or trifluoroacetic acid.

The same process is used to convert a compound of the formula (IX) into a compound of the formula (X).

$C_1$-$C_2$-Alkyl esters (VII) are known and can be prepared from commercially available precursors according to procedures described in the literature, for example from nitriles of the formula (XI), carboxylic acids of the formula (XII), carbonyl chlorides of the formula (XIII), amides of the formula (XIV) or thioamides of the formula (XV) (figure 1). A preferred method is the Hantzsch thiazole synthesis. Starting with (XIV) and commercially available ethyl or methyl halpyruvate in ethanol or in N,N-dimethylformamide in the presence of, for example, triethylamine at room temperature (for examples see WO 07/014,290 and the references cited therein).

Figure 1

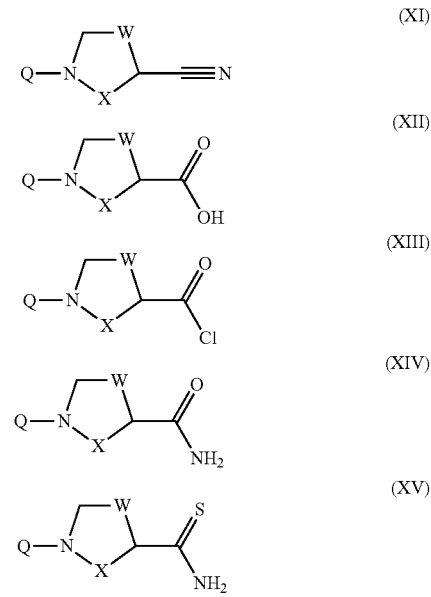

where

Q=H or acid-labile amine protective groups, such as, for example, t-butoxycarbonyl (tBoc) or benzyloxycarbonyl (Cbz), or a benzyl protective group, such as, for example, benzyl (Bn).

W and X are as defined above for formula (I).

One way of preparing compounds of the formula (IV) from corresponding compounds (VI) is shown in Scheme 2.

A compound of the formula (IV) is synthesized by a coupling reaction of a compound of the formula (VI) with a substrate of the formula (V) where Z=Cl, if appropriate in the presence of an acid scavenger/a base.

Acid halides (V) (Z=Cl) or the corresponding carboxylic acids (V) (Z=OH) are commercially available or can be prepared by processes described in the literature (for examples see WO 07/014,290 and the references cited therein). A preferred method is shown in Scheme 7. Pyrazoles (XVIII) can be prepared from diketones (XXI) and commercially available hydrazine (XX) or the corresponding HCl salt in ethanol or in N,N-dimethylformamide, if appropriate in the presence of bases, for example triethylamine at reflux. Compounds (XVI) can be prepared by alkylation of compounds (XVIII) with commercially available α-halo esters (XVII) in acetonitrile or in N,N-dimethylformamide in the presence of bases, for example potassium carbonate at room temperature. Alternatively, compounds (XVI) can be prepared directly from diketones (XXI) and commercially available hydrazine (XIX) or the corresponding HCl salts in ethanol or in N,N-dimethylformamide, if appropriate in the presence of bases, for example triethylamine at reflux. Carboxylic acids (V) (Z=OH) can be prepared by hydrolysis of the esters (XVI) in THF/water mixtures using lithium hydroxide at room temperature. Moreover, a substrate of the general formula (V) where Z=Cl can be prepared from the corresponding acid (Z=OH) by chlorination using processes known from the literature (for example *Tetrahedron* 2005, 61, 10827-10852, and the literature cited therein).

Scheme 7

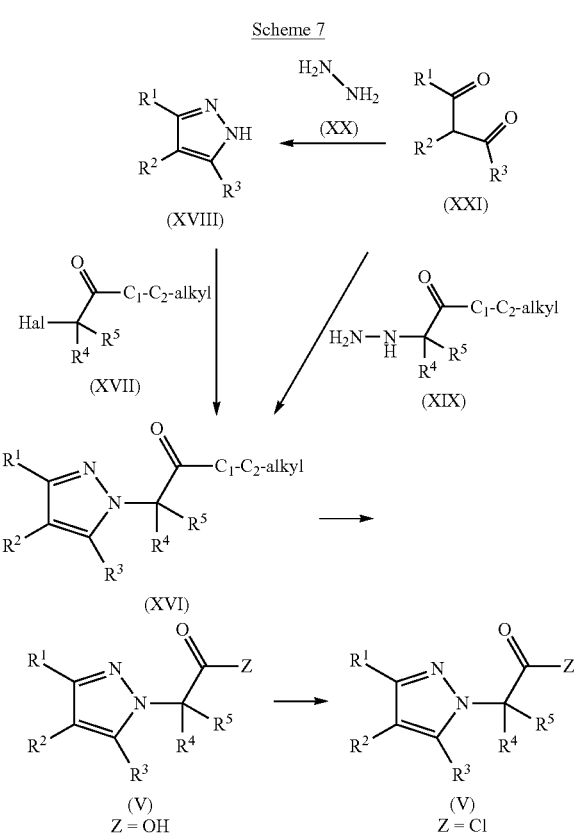

Suitable for use as solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene) and nitriles (for example acetonitrile), or the reaction can be carried out in mixtures of two or more of these solvents. The preferred solvents are tetrahydrofuran and dichloromethane.

At least one equivalent of an acid scavenger/a base (for example Hünig base, triethylamine or commercially available polymeric acid scavengers), based on the starting material of the general formula (V), is employed. If the starting material is a salt, at least two equivalents of the acid scavenger are required.

The reaction is usually carried out at temperatures of 0° C.-100° C. and preferably at 20° C.-30° C., but it can also be carried out at the reflux temperature of the reaction mixture. The reaction time varies depending on the scale of the reaction and the reaction temperature, but is generally between a few minutes and 48 hours.

After the reaction has ended, the compounds (IV) are removed from the reaction mixture using one of the customary separation techniques. If required, the compounds are purified by recrystallisation, distillation or chromatography, or they can, if appropriate, also be used for the next step without prior purification.

Alternatively, a compound of the formula (IV) can also be synthesized from the corresponding compound of the formula (VI) using a substrate of the formula (V) where Z=OH in the presence of a coupling agent analogously to procedures described in the literature (for example *Tetrahedron* 2005, 61, 10827-10852, and the references cited therein).

Suitable coupling agents are, for example, peptide coupling agents (for example N-(3-dimethylaminopropyl)-N'-ethylcarbodiimide mixed with 4-dimethylaminopyridine, N-(3-dimethylaminopropyl)-N'-ethylcarbodiimide mixed with 1-hydroxybenzotriazole, bromotripyrrolidinophosphonium hexafluorophosphate, O-(7-azabenzotriazol-1-yl)-N,N,N',N'-tetramethyluronium hexafluorophosphate, etc.).

If appropriate, a base, such as, for example, triethylamine or Hünig base can be employed in the reaction.

Suitable for use as solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene), nitriles (for example acetonitrile) and amides (for example N,N-dimethylformamide, N,N-dimethylacetamide), or the reaction can be carried out in mixtures of two or more of these solvents. The preferred solvent is dichloromethane.

The reaction is usually carried out at temperatures of 0° C.-100° C. and preferably at 0° C.-30° C., but it can also be carried out at the reflux temperature of the reaction mixture. The reaction time varies depending on the scale of the reaction and the reaction temperature, but is generally between a few minutes and 48 hours.

After the reaction has ended, the compounds (IV) are removed from the reaction mixture using one of the customary separation techniques. If required, the compounds are purified by recrystallisation, distillation or chromatography, or they can, if appropriate, also be used for the next step without prior purification.

Analogously, it is possible to convert compounds of the formula (X) into compounds of the formula (I).

One way of preparing the intermediate (III) from corresponding compounds (IV) is shown in Scheme 3.

The carboxylic acid of the formula (III) can be prepared by hydrolysis of the corresponding $C_1$-$C_2$-alkyl ester of the formula (IV). It is possible to use, for example, the method described in WO2007/014290.

Suitable for use as solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride) and halogenated aromatic hydrocarbons (for example chlorobenzene, dichlorobenzene), or the reaction can be carried out in mixtures of two or more of these solvents.

Suitable alkali metal hydroxides are, for example, LiOH, NaOH or KOH, usually in the presence of water together with a cosolvent, preferably THF and/or methanol, to facilitate dissolution of the ester. The starting material and the alkali metal hydroxide are employed in equimolar amounts; however, the alkali metal hydroxide may, if required, also be used in excess. The carboxylate salt formed is converted into the free acid by treatment with a slight excess of mineral acids, such as, for example, hydrochloric acid or sulfuric acid.

The reaction is usually carried out at temperatures of 0° C.-60° C., but it can also be carried out at the reflux temperature of the reaction mixture. The reaction time varies depending on the scale of the reaction and the reaction temperature, but is generally between a few minutes and 48 hours.

After the reaction has ended, the compounds (III) are removed from the reaction mixture using one of the customary separation techniques. If required, the compounds are purified by recrystallisation, distillation or chromatography.

Analogously, it is possible to convert compounds of the formula (VII) into compounds of the formula (VIII).

One way of preparing compounds of the formula (I) from corresponding compounds (III) is shown in Scheme 4.

A compound of the formula (I) is synthesized by a coupling reaction of a compound of the formula (III) with a substrate of the formula (II), by chlorination using processes known from the literature (for example *Tetrahedron* 2005, 61, 10827-10852, and the literature cited therein), if appropriate in the presence of an acid scavenger/a base.

Substrates of the general formula (II) are commercially available or can be prepared by processes described in the literature (see, for example, "The Chemistry of Functional groups"; "The Chemistry of the Thiol Group"; John Wiley & Sons, 1974, 163-269, and the references cited therein).

Suitable for use as solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene) and nitriles (for example acetonitrile), or the reaction can be carried out in mixtures of two or more of these solvents. The preferred solvents are tetrahydrofuran and dichloromethane.

At least one equivalent of an acid scavenger/a base (for example Hünig base, triethylamine or commercially available polymeric acid scavengers), based on the starting material of the general formula (II), is employed. If the starting material is a salt, at least two equivalents of the acid scavenger are required.

The reaction is usually carried out at temperatures of 0° C.-100° C. and preferably at 20° C.-30° C., but it can also be carried out at the reflux temperature of the reaction mixture. The reaction time varies depending on the scale of the reaction and the reaction temperature, but is generally between a few minutes and 48 hours.

After the reaction has ended, the compounds (I) are removed from the reaction mixture using one of the customary separation techniques. If required, the compounds are purified by recrystallisation, distillation or chromatography, or they can, if appropriate, also be used for the next step without prior purification.

Alternatively, a compound of the formula (I) can also be synthesized from the corresponding compound of the formula (III) (Z=OH) using a substrate of the formula (II) in the presence of a coupling agent analogously to procedures described in the literature (for example *Tetrahedron* 2005, 61, 10827-10852, and the references cited therein).

Suitable coupling agents are, for example, peptide coupling agents (for example N-(3-dimethylaminopropyl)-N'-ethylcarbodiimide mixed with 4-dimethylaminopyridine, N-(3-dimethylaminopropyl)-N'-ethylcarbodiimide mixed with 1-hydroxybenzotriazole, bromotripyrrolidinophosphonium hexafluorophosphate, O-(7-azabenzotriazol-1-yl)-N,N,N',N'-tetramethyluronium hexafluorophosphate, etc.).

If appropriate, a base, such as, for example, triethylamine or Hünig base can be employed in the reaction.

Suitable for use as solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene), nitriles (for example acetonitrile) and amides (for example N,N-dimethylformamide, N,N-dimethylacetamide), or the reaction can be carried out in mixtures of two or more of these solvents. The preferred solvents are N,N-dimethylformiamide and dichloromethane.

The reaction is usually carried out at temperatures of 0° C.-100° C. and preferably at 0° C.-30° C., but it can also be carried out at the reflux temperature of the reaction mixture. The reaction time varies depending on the scale of the reaction and the reaction temperature, but is generally between a few minutes and 48 hours.

After the reaction has ended, the compounds (I) are removed from the reaction mixture using one of the customary separation techniques. If required, the compounds are purified by recrystallisation, distillation or chromatography, or they can, if appropriate, also be used for the next step without prior purification.

The same process can be used to convert a compound of the general formula (VIII) into a compound of the general formula (IX).

One way to prepare compounds of the formula (I) in which $Y^1$ and $Y^2$=S from corresponding compounds (I) in which $Y^1$ and $Y^2$=O is shown in Scheme 5.

A sulfurizing agent, such as, for example, Lawesson's reagent or, for example, phosphorus pentasulfide, is added to a compound of the formula (I) to form a compound of the formula (I) ($Y^1$ and $Y^2$=sulfur). Here, it is possible, for example, to use the method described in *Tetrahedron Lett* 2002, 43 (3), 371-373.

Suitable for use as solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene), nitriles (for example acetonitrile), carboxylic esters (for example ethyl acetate) and amides (for example N,N-dimethylformamide, N,N-dimethylacetamide), and the reaction can be carried out in mixtures of two or more of these solvents. The preferred solvents are chloroform, toluene and 1,2-dimethoxyethane.

Suitable sulfurizing agents are, for example, Lawesson's reagent (see *Tetrahedron* 1986, 42, 6555-6564, *Tetrahedron Lett.* 1993, 46, 7459-7462) and phosphorus pentasulfide. The starting material and the sulfurizing agent are employed in equimolar amounts; however, the sulfurizing agent may, if required, also be used in excess.

The reaction is usually carried out at temperatures of 0° C.-150° C. and preferably at 0° C.-100° C., but it can also be carried out at the reflux temperature of the reaction mixture. The reaction time varies depending on the scale of the reaction and the reaction temperature, but is generally between a few minutes and 48 hours.

After the reaction has ended, the compounds (I) are removed from the reaction mixture using one of the customary separation techniques. If required, the compounds are purified by recrystallisation, distillation or chromatography.

The compound of the formula (XVIII-1)

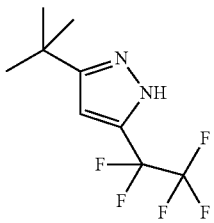

(XVIII-1)

and salts thereof are novel.

The compounds of the formulae (XVI-1), (XVI-2), (XVI-3), (XVI-4) and (XVI-5),

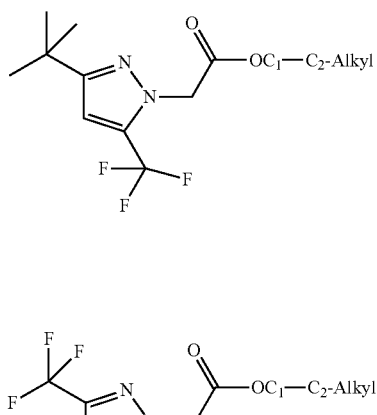

(XVI-1)

(XVI-2)

(XVI-3)

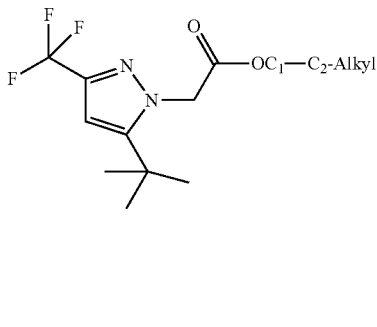

(XVI-4)

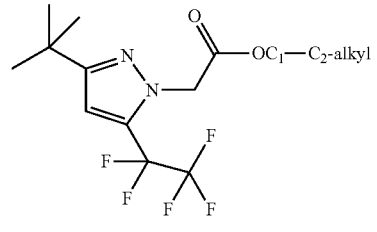

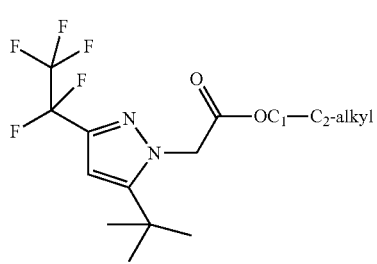

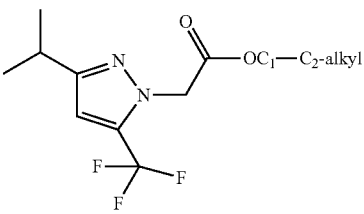

(XVI-5)

and salts thereof are novel.

The compounds of the formulae (V-1), (V-2), (V-3), (V-4) and (V-5),

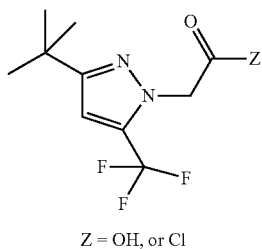

(V-1)

Z = OH, or Cl

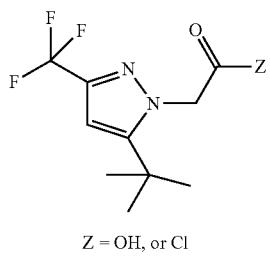

(V-2)

Z = OH, or Cl

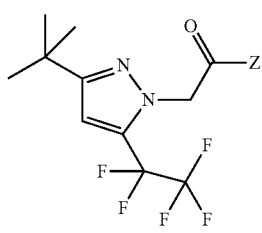

(V-3)

Z = OH, or Cl

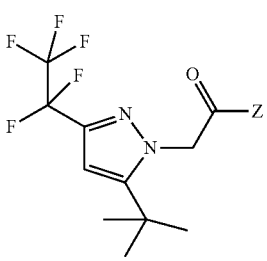

(V-4)

Z = OH, or Cl

-continued (V-5)

Z = OH, or Cl and salts thereof are novel.

The compounds of the formulae (IV-1), (IV-2) and (IV-3), (IV-1)

(IV-2)

(IV-3)

and salts thereof are novel.

The compounds of the formulae (III-1), (III-2) and (III-3) in which (III-1)

-continued (III-2)

(III-3)

Z=OH or chlorine
and salts thereof are novel.
The compounds of the formula (IX) in which (IX)

the symbols have the meanings below
PG is acetyl, $C_1$-$C_2$-alkoxycarbonyl, benzyl or benzyloxycarbonyl,
W, X, $Y^3$, G, $R^6$ and $R^7$ have the general, preferred, particularly preferred or very particularly preferred meanings given above
and salts thereof are novel.

(IX-1)

(IX-2)

The compounds of the formula (X) in which

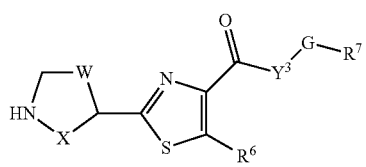
(X)

the symbols have the meanings below
W, X, $Y^3$, G, $R^6$ and $R^7$ have the general, preferred, particularly preferred or very particularly preferred meanings given above
and salts thereof are novel.

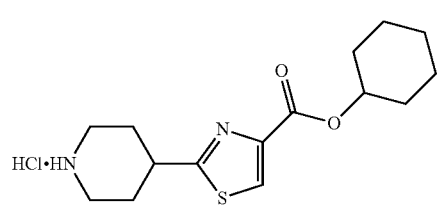
(X-1)

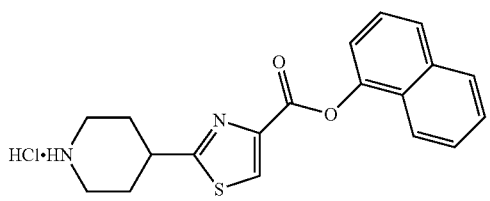
(X-2)

The invention furthermore provides the non-medicinal use of the thiazole-4-carboxylic esters and thioesters according to the invention or mixtures thereof for controlling unwanted microorganisms.

The invention furthermore relates to a composition for controlling unwanted microorganisms which comprises at least one thiazole-4-carboxylic ester or thioester according to the present invention.

Moreover, the invention relates to a method for controlling unwanted microorganisms, characterized in that the thiazole-4-carboxylic esters and thioesters according to the invention are applied to the microorganisms and/or in their habitat.

The invention furthermore relates to seed treated with at least one thiazole-4-carboxylic ester or thioester according to the invention.

A last subject matter of the invention relates to a method for protecting seed against unwanted microorganisms by using seed treated with at least one thiazole-4-carboxylic ester or thioester according to the present invention.

The substances according to the invention have potent microbicidal activity and can be employed for controlling unwanted microorganisms, such as fungi and bacteria, in crop protection and in the protection of materials.

The thiazole-4-carboxylic esters and thioesters of the formula (I) according to the invention have very good fungicidal properties and can be used in crop protection, for example, for controlling Plasmodiophoromycetes, Oomycetes, Chytridiomycetes, Zygomycetes, Ascomycetes, Basidiomycetes and Deuteromycetes.

Bactericides can be employed in crop protection, for example, for controlling Pseudomonadaceae, Rhizobiaceae, Enterobacteriaceae, Corynebacteriaceae and Streptomycetaceae.

The fungicidal compositions according to the invention can be used for the curative or protective control of phytopathogenic fungi. Accordingly, the invention also relates to curative and protective methods for controlling phytopathogenic fungi using the active compounds or compositions according to the invention, which are applied to the seed, the plant or plant parts, the fruit or the soil in which the plants grow.

The compositions according to the invention for controlling phytopathogenic fungi in crop protection comprise an effective, but non-phytotoxic amount of the active compounds according to the invention. "Effective, but non-phytotoxic amount" means an amount of the composition according to the invention which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on a plurality of factors, for example on the fungus to be controlled, the plant, the climatic conditions and the ingredients of the compositions according to the invention.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. Parts of plants also include harvested plants and vegetative and generative propagation material, for example seedlings, tubers, rhizomes, cuttings and seeds.

The following plants may be mentioned as plants which can be treated according to the invention: cotton, flax, grapevines, fruit, vegetables, such as *Rosaceae* sp. (for example pomaceous fruit, such as apples and pears, but also stone fruit, such as apricots, cherries, almonds and peaches and soft fruit such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit), *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumbers), *Alliaceae* sp. (for example leek, onions), *Papilionaceae* sp. (for example peas); major crop plants, such as *Gramineae* sp. (for example maize, lawn, cereals such as wheat, rye, rice, barley, oats, millet and triticale), *Asteraceae* sp. (for example sunflowers), *Brassicaceae* sp. (for example white cabbage, red cabbage, broccoli, cauliflowers, brussels sprouts, pak Choi, kohlrabi, garden radish, and also oilseed rape, mustard, horseradish and cress), *Fabacae* sp. (for example beans, peanuts), *Papilionaceae* sp. (for example soya beans), *Solanaceae* sp. (for example potatoes), *Chenopodiaceae* sp. (for example sugarbeet, fodderbeet, swiss chard, beetroot); crop plants and ornamental plants in garden and forest; and also in each case genetically modified varieties of these plants. Preference is given to treating cereal plants according to the invention.

Some pathogens of fungal diseases which can be treated according to the invention may be mentioned by way of example, but not by way of limitation:

diseases caused by powdery mildew pathogens, such as, for example, *Blumeria* species, such as, for example, *Blumeria graminis; Podosphaera* species, such as, for example, *Podosphaera leuco-tricha; Sphaerotheca* species, such as, for example, *Sphaerotheca fuliginea; Uncinula* species, such as, for example, *Uncinula necator;* diseases caused by rust disease pathogens, such as, for example, *Gymnosporangium* species, such as, for example, *Gymnosporangium sabinae; Hemileia* species, such as, for example, *Hemileia vastatrix; Phakopsora* species, such as, for example, *Phakopsora pachyrhizi* and *Phakopsora meibomiae; Puccinia* species, such as, for example, *Puccinia recondita* or *Puccinia triticina; Uromyces* species, such as, for example, *Uromyces appendiculatus;* diseases caused by pathogens from the group of the Oomycetes, such as, for example, *Bremia* species, such as, for example, *Bremia lactucae; Peronospora* species, such as, for example, *Peronospora pisi* or *P. brassicae; Phytophthora* species, such as, for example, *Phytophthora infestans; Plasmopara* species, such as, for example, *Plasmopara viticola; Pseudoperonospora* species, such as, for example, *Pseudoperonospora humuli* or *Pseudoperonospora cubensis; Pythium* species, such as, for example, *Pythium ultimum;* leaf blotch diseases and leaf wilt diseases caused, for example, by *Alternaria* species, such as, for example, *Alternaria solani; Cercospora* species, such as, for example, *Cercospora beticola; Cladiosporium* species, such as, for example, *Cladiosporium cucumerinum; Cochliobolus* species, such as, for example, *Cochliobolus sativus* (conidia form: *Drechslera*, syn: *Helminthosporium); Colletotrichum* species, such as, for example, *Colletotrichum lindemuthanium; Cycloconium* species, such as, for example, *Cycloconium oleaginum; Diaporthe* species, such as, for example, *Diaporthe citri; Elsinoe* species, such as, for example, *Elsinoe fawcettii; Gloeosporium* species, such as, for example, *Gloeosporium laeticolor; Glomerella* species, such as, for example, *Glomerella cingulata; Guignardia* species, such as, for example, *Guignardia bidwelli; Leptosphaeria* species, such as, for example, *Leptosphaeria maculans; Magnaporthe* species, such as, for example, *Magnaporthe grisea; Microdochium* species, such as, for example, *Microdochium nivale; Mycosphaerella* species, such as, for example, *Mycosphaerella graminicola* and *M. fijiensis; Phaeosphaeria* species, such as, for example, *Phaeosphaeria nodorum; Pyrenophora* species, such as, for example, *Pyrenophora teres; Ramularia* species, such as, for example, *Ramularia collocygni; Rhynchosporium* species, such as, for example, *Rhynchosporium secalis; Septoria* species, such as, for example, *Septoria apii; Typhula* species, such as, for example, *Typhula incamata; Venturia* species, such as, for example, *Venturia inaequalis;* root and stem diseases caused, for example, by *Corticium* species, such as, for example, *Corticium graminearum; Fusarium* species, such as, for example, *Fusarium oxysporum; Gaeumannomyces* species, such as, for example, *Gaeumannomyces graminis; Rhizoctonia* species, such as, for example *Rhizoctonia solani; Tapesia* species, such as, for example, *Tapesia acuformis; Thielaviopsis* species, such as, for example, *Thielaviopsis basicola;* ear and panicle diseases (including corn cobs) caused, for example, by *Alternaria* species, such as, for example, *Alternaria* spp.; *Aspergillus* species, such as, for example, *Aspergillus flavus; Cladosporium* species, such as, for example, *Cladosporium cladosporioides; Claviceps* species, such as, for example, *Claviceps purpurea; Fusarium* species, such as, for example, *Fusarium culmorum; Gibberella* species, such as, for example, *Gibberella zeae; Monographella* species, such as, for example, *Monographella nivalis; Septoria* species, such as, for example, *Septoria nodorum;* diseases caused by smut fungi, such as, for example, *Sphacelotheca* species, such as, for example, *Sphacelotheca reiliana; Tilletia* species, such as, for example, *Tilletia caries, T. controversa; Urocystis* species, such as, for example, *Urocystis occulta; Ustilago* species, such as, for example, *Ustilago nuda, U. nuda tritici;*

Fruit rot caused, for example, by *Aspergillus* species, such as, for example, *Aspergillus flavus; Botrytis* species, such as, for example, *Botrytis cinerea; Penicillium* species, such as, for example, *Penicillium expansum* and *P. purpurogenum; Sclerotinia* species, such as, for example, *Sclerotinia sclerotiorum;*

*Verticilium* species, such as, for example, *Verticilium alboatrum;* seed- and soil-borne rot and wilt diseases, and also diseases of seedlings, caused, for example, by *Fusarium* species, such as, for example, *Fusarium culmorum; Phytophthora* species, such as, for example, *Phytophthora cactorum; Pythium* species, such as, for example, *Pythium ultimum; Rhizoctonia* species, such as, for example, *Rhizoctonia solani; Sclerotium* species, such as, for example, *Sclerotium rolfsii;* cancerous diseases, galls and witches' broom caused, for example, by *Nectria* species, such as, for example, *Nectria galligena;* wilt diseases caused, for example, by *Monilinia* species, such as, for example, *Monilinia laxa;* deformations of leaves, flowers and fruits caused, for example, by *Taphrina* species, such as, for example, *Taphrina deformans;* degenerative diseases of woody plants caused, for example, by Esca species, such as, for example, *Phaeomoniella chlamydospora* and *Phaeoacremonium aleophilum* and *Fomitiporia mediterranea;* diseases of flowers and seeds caused, for example, by *Botrytis* species, such as, for example, *Botrytis cinerea;* diseases of plant tubers caused, for example, by *Rhizoctonia* species, such as, for example, *Rhizoctonia solani; Helminthosporium* species, such as, for example, *Helminthosporium solani;* diseases caused by bacterial pathogens, such as, for example, *Xanthomonas* species, such as, for example, *Xanthomonas campestris* pv. *oryzae; Pseudomonas* species, such as, for example, *Pseudomonas syringae* pv. *lachrymans; Erwinia* species, such as, for example, *Erwinia amylovora;*

Preference is given to controlling the following diseases of soybeans:

Fungal diseases on leaves, stems, pods and seeds caused, for example, by alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanideunatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compounds according to the invention also have very good fortifying action in plants. Accordingly, they can be used for mobilizing the defenses of the plant against attack by undesirable microorganisms.

Plant-strengthening (resistance-inducing) substances are to be understood as meaning, in the present context, those substances which are capable of stimulating the defense system of plants in such a way that the treated plants, when subsequently inoculated with undesired microorganisms, develop a high degree of resistance to these microorganisms.

In the present case, undesirable microorganisms are to be understood as meaning phytopathogenic fungi and bacteria. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention can be employed particularly successfully for controlling diseases in viticulture and fruit and vegetable growing such as, for example, against *Botrytis, Venturia, Sphaerotheca, Podosphaera, Phytophthora* and *Plasmopara* species.

The active compounds according to the invention are also suitable for increasing the yield of crops. In addition, they show reduced toxicity and are well tolerated by plants.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be used as intermediates or precursors for the synthesis of other active compounds.

If appropriate, the active compounds according to the invention can also be employed in specific concentrations and application rates as herbicides, for influencing plant growth, and for controlling animal pests. If appropriate, they can also be used as intermediates and precursors for the synthesis of further active compounds.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

The active compounds according to the invention can also be used as defoliants, desiccants, haulm killers and, especially, as weedkillers. Weeds in the broadest sense are understood to mean all plants which grow in locations where they are undesired. Whether the substances according to the invention act as total or selective herbicides depends essentially on the amount used.

Moreover, in the protection of materials, the active compounds or compositions according to the invention can be employed for protecting industrial materials against attack and destruction by unwanted microorganisms, such as, for example, fungi.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids particularly preferably wood. The active compounds or compositions according to the invention may prevent disadvantageous effects, such as rotting, decay, discoloration, decoloration or formation of mold.

The method according to the invention for controlling unwanted fungi can also be employed for protecting storage goods. Here, storage goods are to be understood as meaning natural substances of vegetable or animal origin or processed products thereof of natural origin, for which long-term protection is desired. Storage goods of vegetable origin, such as, for example, plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The active compounds according to the invention may prevent disadvantageous effects, such as rotting, decay, discoloration, decoloration or formation of mold.

Microorganisms capable of degrading or changing the industrial materials which may be mentioned are, for example, bacteria, fungi, yeasts, algae and slime organisms. The active compounds according to the invention preferably act against fungi, in particular molds, wood-discoloring and wood-destroying fungi (Basidiomycetes), and against slime organisms and algae. Microorganisms of the following genera may be mentioned as examples: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Escherichia*, such as *Escherichia coli*; *Pseudomonas*, such as *Pseudomonas aeruginosa*; *Staphylococcus*, such as *Staphylococcus aureus*.

The present invention furthermore relates to a composition for controlling unwanted microorganisms, which composition comprises at least one of the thiazole-4-carboxylic ester or thioesters according to the invention. These are preferably fungicidal composition which comprise agriculturally suitable auxiliaries, solvents, carriers, surfactants or extenders.

According to the invention, a carrier is a natural or synthetic organic or inorganic substance with which the active compounds are mixed or bonded for better applicability, in particular for application to plants or plant parts or seed. The carrier, which may be solid or liquid, is generally inert and should be suitable for use in agriculture.

As solid carriers these are suitable: for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulfonates, alkyl sulphates, arylsulfonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

The active compounds can be converted into the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances.

The active compounds can be applied as such, in the form of their formulations or the use forms prepared therefrom, such as ready-to-use solutions, emulsions, water- or oil-based suspensions, powders, wettable powders, pastes, soluble powders, dusts, soluble granules, granules for broadcasting, suspoemulsion concentrates, natural products impregnated with active compound, synthetic materials impregnated with active compound, fertilizers and also microencapsulations in polymeric substances. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

The formulations mentioned can be prepared in a manner known per se, for example by mixing the active compounds with at least one customary extender, solvent or diluent, emulsifier, dispersant, and/or binder or fixative, wetting agent, water-repellent, if appropriate desiccants and UV stabilizers and, if appropriate, dyes and pigments, defoamers, preservatives, secondary thickeners, adhesives, gibberellins and also further processing auxiliaries.

The compositions according to the invention include not only formulations which are already ready for use and can be applied with a suitable apparatus to the plant or the seed, but also commercial concentrates which have to be diluted with water prior to use.

The active compounds according to the invention can be present as such or in their (commercial) formulations and in the use forms prepared from these formulations as a mixture with other (known) active compounds, such as insecticides, attractants, sterilants, bactericides, acaricides, nematicides, fungicides, growth regulators, herbicides, fertilizers, safeners and/or semiochemicals.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water.

The compositions according to the invention may comprise additional further components, such as, for example, surfactants. Suitable surfactants are emulsifiers and/or foam formers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

The formulations generally comprise between 0.05 and 99% by weight, 0.01 and 98% by weight, preferably between 0.1 and 95% by weight, particularly preferably between 0.5 and 90% of active compound, very particularly preferably between 10 and 70% by weight.

The formulations described above can be used in a method according to the invention for controlling unwanted microorganisms, where the thiazole-4-carboxylic esters and thioesters according to the invention are applied to the microorganisms and/or to their habitat.

The active compounds according to the invention can be used as such or in their formulations, also in a mixture with known fungicides, bactericides, acaricides, nematicides or insecticides, to broaden, for example, the activity spectrum or to prevent development of resistance.

Suitable mixing partners are, for example, known fungicides, insecticides, acaricides, nematicides or else bactericides (see also Pesticide Manual, 13th ed.).

A mixture with other known active compounds, such as herbicides, or with fertilizers and growth regulators, safeners and/or semiochemicals is also possible.

The compounds are employed in a customary manner appropriate for the use forms.

The invention furthermore includes a method for treating seed.

A further aspect of the present invention relates in particular to seed treated with at least one of the thiazole-4-carboxylic esters or thioesters according to the invention. The seed according to the invention is used in methods for protecting seed against animal pests and/or phytopathogenic harmful fungi. In these methods, seed treated with at least one active compound according to the invention is employed.

The active compounds or compositions according to the invention are also suitable for treating seed. A large part of the damage to crop plants caused by harmful organisms is triggered by the infection of the seed during storage or after sowing both during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of animal pests and/or phytopathogenic harmful fungi by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with, or at least reduce considerably, the additional application of crop protection agents after planting or after emergence of the plants. It is furthermore desirable to optimize the amount of active compound employed in such a way as to provide optimum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

Accordingly, the present invention also relates to a method for protecting seed and germinating plants against attack by animal pests and/or phytopathogenic harmful fungi by treating the seed with a composition according to the invention. The invention also relates to the use of the compositions according to the invention for treating seed for protecting the seed and the germinating plant against phytopathogenic fungi. Furthermore, the invention relates to seed treated with a composition according to the invention for protection against phytopathogenic fungi.

The control of animal pests and/or phytopathogenic harmful fungi which damage plants post-emergence is carried out primarily by treating the soil and the above-ground parts of plants with plant protection agents. Owing to the concerns regarding a possible impact of the plant protection agent on the environment and the health of humans and animals, there are efforts to reduce the amount of active compounds applied.

One of the advantages of the present invention is that, because of the particular systemic properties of the compositions according to the invention, treatment of the seed with these compositions not only protects the seed itself, but also the resulting plants after emergence, from animal pests and/or phytopathogenic harmful fungi. In this manner, the immediate treatment of the crop at the time of sowing or shortly thereafter can be dispensed with.

It is also considered to be advantageous that the active compounds or compositions according to the invention can be used in particular also for transgenic seed where the plant growing from this seed is capable of expressing a protein which acts against pests. By treating such seed with the active compounds or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety which is employed in agriculture, in the greenhouse, in forests or in horticulture. In particular, this takes the faun of seed of cereals (such as wheat, barley, rye, millet and oats), maize, cotton, soybeans, rice, potatoes, sunflowers, beans, coffee, beets (for example sugarbeets and fodder beets), peanuts, vegetables (such as such as tomatoes, cucumbers, onions and lettuce), lawn and ornamental plants. The treatment of the seed of cereals (such as wheat, barley, rye and oats), maize and rice is of particular importance.

As also described further below, the treatment of transgenic seed with the active compounds or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis*.

Within the context of the present invention, the composition according to the invention is applied to the seed either alone or in suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

The compositions according to the invention can be applied directly, i.e. without any other components and undiluted. In general, it is preferred to apply the compositions to the seed in the form of a suitable formulation. Suitable formulations and methods for treating seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compounds which can be used in accordance with the invention can be converted into the customary seed-dressing formulations, such as solutions, emulsions, suspensions, powders, foams, slurries or other coating compositions for seed, and also ULV formulations These formulations are prepared in a known manner, by mixing the active compounds or active compound combinations with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. In this context, not only pigments, which are sparingly soluble in water, but also dyes, which are soluble in water, may be used. Examples which may be mentioned are the colorants known by the names Rhodamin B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemical active compounds. Preference is given to using alkylnaphthalenesulphonates, such as diisopropyl- or diisobutylnaphthalenesulphonates.

Suitable dispersants and/or emulsifiers which may be present in the seed-dressing formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants. Suitable nonionic dispersants which may be mentioned are, in particular, ethylene oxide/propylene oxide block polymers, alkylphenol polyglycol ethers and tristryrylphenol polyglycol ether, and their phosphated or sulphated derivatives. Suitable anionic dispersants are, in particular, lignosulphonates, polyacrylic acid salts and arylsulphonate/formaldehyde condensates.

Antifoams which may be present in the seed-dressing formulations which can be used in accordance with the invention are all foam-inhibiting substances conventionally used for the formulation of agrochemical active compounds. Silicone antifoams and magnesium stearate can preferably be used.

Preservatives which may be present in the seed-dressing formulations which can be used in accordance with the invention are all substances which can be employed for such purposes in agrochemical compositions. Dichlorophene and benzyl alcohol hemiformal may be mentioned by way of example.

Secondary thickeners which may be present in the seed-dressing formulations which can be used in accordance with the invention are all substances which can be employed for such purposes in agrochemical compositions. Cellulose derivatives, acrylic acid derivatives, xanthan, modified clays and finely divided silica are preferred.

Adhesives which may be present in the seed-dressing formulations which can be used in accordance with the invention are all customary binders which can be employed in seed-dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel" [Chemistry of plant protection agents and pesticides], vol. 2, Springer Verlag, 1970, p. 401-412).

The seed-dressing formulations which can be used in accordance with the invention can be employed for the treatment of a wide range of seed, either directly or after previously having been diluted with water. Thus, the concentrates or the preparations obtainable therefrom by dilution with water may be used to dress the seed of cereals, such as wheat, barley, rye, oats, and triticale, and also the seed of maize, rice, oilseed rape, peas, beans, cotton, sunflowers, and beets, or else vegetable seed of any of a very wide variety of kinds. The seed-dressing formulations which can be used according to the invention or their dilute preparations may also be used to dress seed of transgenic plants. In this context, additional synergistic effects may also occur in cooperation with the substances formed by expression.

All mixers which can conventionally be employed for the seed-dressing operation are suitable for treating seed with the seed-dressing formulations which can be used in accordance with the invention or with the preparations prepared therefrom by addition of water. Specifically, a procedure is followed during the seed-dressing operation in which the seed is placed into a mixer, the specific desired amount of seed-dressing formulations, either as such or after previously having been diluted with water, is added, and everything is mixed until the formulation is distributed uniformly on the seed. If appropriate, this is followed by a drying process.

The application rate of the seed dressing formulations which can be used according to the invention may be varied within a relatively wide range. It depends on the respective content of the active compounds in the formulations and on the seed. The active compound combination application rates are generally between 0.001 and 50 g per kilogram of seed, preferably between 0.01 and 15 g per kilogram of seed.

In addition, the compounds of the formula (I) according to the invention also have very good antimycotic activity. They have a very broad antimycotic activity spectrum in particular against dermatophytes and yeasts, molds and diphasic fungi, (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means limits the mycotic spectrum covered, but is only for illustration.

Accordingly, the active compounds of the formula (I) according to the invention can be used both in medical and in non-medical applications.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seed of the plants.

When using the active compounds according to the invention as fungicides, the application rates can be varied within a relatively wide range, depending on the kind of application. The application rate of the active compounds according to the invention is

- when treating plant parts, for example leaves: from 0.1 to 10 000 g/ha, preferably from 10 to 1 000 g/ha, particularly preferably from 50 to 300 g/ha (when the application is carried out by watering or dripping, it is even possible to reduce the application rate, especially when inert substrates such as rock wool or perlite are used);
- when treating seed: from 2 to 200 g per 100 kg of seed, preferably from 3 to 150 g per 100 kg of seed, particularly preferably from 2.5 to 25 g per 100 kg of seed, very particularly preferably from 2.5 to 12.5 g per 100 kg of seed;
- when treating the soil: from 0.1 to 10 000 g/ha, preferably from 1 to 5000 g/ha.

These application rates are mentioned only by way of example and are not limiting in the sense of the invention.

With respect to possible additional partners for mixing, reference is made to the insecticides and fungicides mentioned above.

The compounds according to the invention can at the same time be employed for protecting objects which come into contact with saltwater or brackish water, such as hulls, screens, nets, buildings, moorings and signaling systems, against fouling.

Furthermore, the compounds according to the invention can be used alone or in combinations with other active compounds as antifouling compositions.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or hypochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. Possible are thus, for example, the following effects which exceed the effects which were to be expected: reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products.

At certain application rates, the active compound combinations according to the invention may also have a strengthening effect in plants. Accordingly, they are suitable for mobilizing the defense system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, also those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are understood as meaning phytopathogenic fungi, bacteria and viruses. Thus, the substances according to the invention can be employed for protecting plants against attack by the abovementioned pathogens within a certain period of time after the treatment. The period within which protection is brought about generally extends from 1 to 10 days, preferably 1 to 7 days, after the treatment of the plants with the active compounds.

Plants and plant varieties which are preferably treated according to the invention include all plants which have genetic material which imparts particularly advantageous, useful traits to these plants (whether obtained by breeding and/or biotechnological means).

Plants and plant varieties which are also preferably treated according to the invention are resistant against one or more biotic stresses, i.e. said plants have a better defense against animal and microbial pests, such as against nematodes, insects, mites, phytopathogenic fungi, bacteria, viruses and/or viroids.

Plants and plant varieties which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid vigour, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in the hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male sterile plants can also be obtained by plant biotechnology methods such as genetic engineering. A particularly useful means of obtaining male sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyloxy(thio) benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding. Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins listed online at: http://www.lifesci.sussex-.ac.uk/Home/Neil_Crickmore/Bt/, or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR604;

5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, for example proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins.

7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose) polymerase (PARP) gene in the plant cells or plants.

b. plants which contain a stress tolerance-enhancing transgene capable of reducing the expression and/or the activity of the PARG encoding genes of the plants or plants cells;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyl transferase, nicotinamide adenine dinucleotide synthetase or nicotinamide phosphoribosyltransferase.

Plants or plant varieties (obtained by plant biotechnology methods such as genetic engineering) which may also be treated according to the invention show altered quantity, quality and/or storage-stability of the harvested product and/or altered properties of specific ingredients of the harvested product such as, for example:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behavior, the gel resistance, the grain size and/or grain morphology of the starch in comparison to the synthesized starch in wild-type plant cells or plants, such that this modified starch is better suited for certain applications.

2) Transgenic plants which synthesize non-starch carbohydrate polymers or which synthesize non-starch carbohydrate polymers with altered properties in comparison to wild type plants without genetic modification. Examples are plants which produce polyfructose, especially of the inulin and levan type, plants which produce alpha-1,4-glucans, plants which produce alpha-1,6 branched alpha-1,4-glucans, and plants producing alternan 3) Transgenic plants which produce hyaluronan.

Plants or plant varieties (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, which contain an altered form of cellulose synthase genes,
b) plants, such as cotton plants, which contain an altered form of rsw2 or rsw3 homologous nucleic acids;
c) plants, such as cotton plants, with an increased expression of sucrose phosphate synthase;
d) plants, such as cotton plants, with an increased expression of sucrose synthase;
e) plants, such as cotton plants, wherein the timing of the plasmodesmatal gating at the basis of the fiber cell is altered, for example through downregulation of fiber-selective β-1,3-glucanase;
f) plants, such as cotton plants, which have fibers with altered reactivity, for example through the expression of the N-acetylglucosaminetransferase gene including nodC and chitin synthase genes.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content;
b) plants, such as oilseed rape plants, which produce oil having a low linolenic acid content.
c) plants, such as oilseed rape plants, which produce oil having a low level of saturated fatty acids.

Particularly useful transgenic plants which may be treated according to the invention are plants which comprise one or more genes which encode one or more toxins are the transgenic plants available under the following trade names' YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, that are listed for example in the databases for various national or regional regulatory agencies (see for example http://gmoinfo.jrc.it/gmp_browse.aspx and http://www.agbios.com/dbase.php).

The plants listed can be treated according to the invention in a particularly advantageous manner with the compounds of the general formula (I) and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds or compositions according to the invention can thus be employed for protecting plants for a certain period of time after treatment against attack by the pathogens mentioned. The period for which protection is provided extends generally for 1 to 28 days, preferably 1 to 14 days, particularly preferably for 1 to 10 days, very particularly preferably for 1 to 7 days after the treatment of the plants with the active compounds, or up to 200 days after a seed treatment.

The preparation and the use of the active compounds of the formula (I) according to the invention is illustrated by the examples below. However, the invention is not limited to these examples.

General note: Unless indicated otherwise, all chromatographic purification and separation steps are carried out on silica gel and using a solvent gradient of from 0:100 ethyl acetate/cyclohexane to 100:0 ethyl acetate/cyclohexane.

General note: Unless indicated otherwise, all chromatographic purification and separation steps are carried out on silica gel and using a solvent gradient of from 0:100 ethyl acetate/hexane to 100:0 ethyl acetate/hexane.

PREPARATION OF STARTING MATERIALS OF THE FORMULA (XVIII)

3-tert-Butyl-5-(pentafluoroethyl)-1H-pyrazole (XVIII-1)

At room temperature, hydrazine hydrate (2.06 g) is added to a solution of 1,1,1,2,2-pentafluoro-6,6-dimethylheptane-3,5-dione (10.1 g) in ethanol (100 ml). The reaction mixture is stirred at room temperature overnight. After removal of the solvents under reduced pressure, 3-tert-butyl-5-(pentafluoroethyl)-1H-pyrazole (7.9 g, 79%) is obtained.

log P (pH 2.7): 3.23

$^1$H NMR (DMSO-$d_6$, 400 MHz): $\delta_{ppm}$: 1.30 (s, 9H), 6.40 (s, 1H) 13.3 (s, 1H)

MS (ESI): 243 ([M+H]$^+$)

5-tert-Butyl-3-(trifluoromethyl)-1H-pyrazole (XVIII-2)

1,1,1-Trifluoro-5,5-dimethylhexane-2,4-dione (14.1 g) is reacted analogously to Example XVIII-1 with hydrazine hydrate (3.61 g). This gives 5-tert-butyl-3-(trifluoromethyl)-1H-pyrazole (10.7 g, 77%)

¹H NMR (DMSO-d₆, 400 MHz): δ_ppm: 1.30 (s, 9H), 6.39 (s, 1H), 13.1 (s, 1H)

MS (ESI): 192 ([M]⁻⁺)

3-Isopropyl-5-(trifluoromethyl)-1H-pyrazole (XVIII-3)

1,1,1-Trifluoro-5-methylhexane-2,4-dione (24.9 g) is reacted analogously to Example XVIII-1 with hydrazine hydrate (6.84 g). This gives 3-isopropyl-5-(trifluoromethyl)-1H-pyrazole (19 g, 78%)

¹H NMR (DMSO-d₆, 400 MHz): δ_ppm: 1.23 (d, 6H), 3.02 (septet, 1H), 6.39 (s, 1H), 13.1 (s, 1H)

MS (ESI): 178 ([M]⁻⁺)

PREPARATION OF STARTING MATERIALS OF THE FORMULA (XVI)

Ethyl [3-tert-butyl-5-(trifluoromethyl)-1H-pyrazol-1-yl]acetate (XVI-1) and ethyl [5-tert-butyl-3-(trifluoromethyl)-1H-pyrazol-1-yl]acetate (XVI-2)

Potassium carbonate (15.4 g) is added to a solution of 5-tert-butyl-3-(trifluoromethyl)-1H-pyrazole (XVIII-2, 10.7 g) in acetonitrile (150 ml). Ethyl bromoacetate (13.9 g) is then added dropwise at room temperature. The reaction mixture is stirred at room temperature overnight and then filtered and concentrated under reduced pressure. The residue is purified chromatographically. This gives ethyl [3-tert-butyl-5-(trifluoromethyl)-1H-pyrazol-1-yl]acetate (7.84 g, 50%) and ethyl [5-tert-butyl-3-(trifluoromethyl)-1H-pyrazol-1-yl]acetate (4.53 g, 29%).

Ethyl [3-tert-butyl-5-(trifluoromethyl)-1H-pyrazol-1-yl]acetate (XVI-1)

log P (pH 2.7): 3.89

¹H NMR (DMSO-d₆, 400 MHz): δ_ppm: 1.18 (t, 3H), 1.26 (s, 9H), 4.15 (q, 2H), 5.06 (s, 2H), 6.79 (s, 1H)

MS (ESI): 279 ([M+H]⁺)

Ethyl [5-tert-butyl-3-(trifluoromethyl)-1H-pyrazol-1-yl]acetate (XVI-2)

log P (pH 2.7): 3.48

¹H NMR (DMSO-d₆, 400 MHz): δ_ppm: 1.20 (t, 3H), 1.31 (s, 9H), 4.17 (q, 2H), 5.18 (s, 2H), 6.47 (s, 1H)

MS (ESI): 279 ([M+H]⁺)

Ethyl [3-tert-butyl-5-(pentafluoroethyl)-1H-pyrazol-1-yl]acetate (XVI-3) and ethyl [5-tert-butyl-3-(pentafluoroethyl)-1H-pyrazol-1-yl]acetate (XVI-4)

3-tert-Butyl-5-(pentafluoroethyl)-1H-pyrazole (XVIII-1, 7.90 g) is reacted analogously to Examples XVI-1 and XVI-2 with ethyl bromoacetate (8.17 g). This gives, after chromatographic purification, ethyl [3-tert-butyl-5-(pentafluoroethyl)-1H-pyrazol-1-yl]acetate (2.50 g, 23%) and ethyl [5-tert-butyl-3-(pentafluoroethyl)-1H-pyrazol-1-yl]acetate (4.80 g, 45%).

Ethyl [3-tert-butyl-5-(pentafluoroethyl)-1H-pyrazol-1-yl]acetate (XVI-3)

log P (pH 2.7): 4.45

¹H NMR (DMSO-d₆, 400 MHz): δ_ppm: 1.18 (t, 3H), 1.26 (s, 9H), 4.15 (q, 2H), 5.07 (s, 2H), 6.75 (s, 1H)

MS (ESI): 329 ([M+H]⁺)

Ethyl [5-tert-butyl-3-(pentafluoroethyl)-1H-pyrazol-1-yl]acetate (XVI-4)

log P (pH 2.7): 4.05

¹H NMR (DMSO-d₆, 400 MHz): δ_ppm: 1.18 (t, 3H), 1.32 (s, 9H), 4.16 (q, 2H), 5.20 (s, 2H), 6.47 (s, 1H)

MS (ESI): 329 ([M+H]⁺)

Ethyl [3-isopropyl-5-(trifluoromethyl)-1H-pyrazol-1-yl]acetate (XVI-5)

3-Isopropyl-5-(trifluoromethyl)-1H-pyrazole (XVIII-3, 19.3 g) is reacted analogously to Examples XVI-1 and XVI-2 with ethyl bromoacetate (27.1 g). This gives ethyl [3-isopropyl-5-(trifluoromethyl)-1H-pyrazol-1-yl]acetate (26.2 g, 92%)

log P (pH 2.7): 3.22

¹H NMR (DMSO-d₆, 400 MHz): δ_ppm: 1.18-1.22 (m, 3H), 1.20 (d, 6H), 3.0 (septet, 1H), 4.17 (q, 2H), 5.11 (s, 2H), 6.54 (s, 1H)

MS (ESI): 265 ([M+H]⁺)

Ethyl [4-chloro-5-methyl-3-(trifluoromethyl)-1H-pyrazol-1-yl]acetate (XVI-6)

4-Chloro-5-methyl-3-(trifluoromethyl)-1H-pyrazole (14.9 g) is reacted analogously to Examples XVI-1 and XVI-2 with ethyl bromoacetate (20.3 g). This gives ethyl [4-chloro-5-methyl-3-(trifluoromethyl)-1H-pyrazol-1-yl]acetate (19.5 g, 89%)

log P (pH 2.7): 3.11

¹H NMR (DMSO-d₆, 400 MHz): δ_ppm: 1.22 (t, 3H), 2.25 (s, 3H), 4.18 (q, 2H), 5.24 (s, 2H)

MS (ESI): 271 ([M+H]⁺)

PREPARATION OF STARTING MATERIALS OF THE FORMULA (V)

[3-tert-Butyl-5-(trifluoromethyl)-1H-pyrazol-1-yl]acetic acid (V-1)

At room temperature, a solution of lithium hydroxide monohydrate (2.35 g) in water (20 ml) is added dropwise to a solution of ethyl [3-tert-butyl-5-(trifluoromethyl)-1H-pyrazol-1-yl]acetate (XVI-1, 7.80 g) in tetrahydrofuran (80 ml). The reaction mixture is stirred for 2 hours. After removal of the solvent under reduced pressure, the residue is, at 0° C., slowly adjusted to pH 2-3 using dilute hydrochloric acid (1M). This gives, after filtration and drying, [3-tert-butyl-5-(trifluoromethyl)-1H-pyrazol-1-yl]acetic acid as a white solid (7.1 g, 100%).

log P (pH 2.7): 2.45

¹H NMR (DMSO-d₆, 400 MHz): δ_ppm: 1.26 (s, 9H), 4.95 (s, 2H), 6.76 (s, 1H)

MS (ESI): 251 ([M+H]⁺)

[5-tert-Butyl-3-(trifluoromethyl)-1H-pyrazol-1-yl]acetic acid (V-2)

Ethyl [5-tert-butyl-3-(trifluoromethyl)-1H-pyrazol-1-yl]acetate (XVI-2, 4.50 g) is reacted analogously to Example V-1. This gives, after filtration and drying, [5-tert-butyl-3-(trifluoromethyl)-1H-pyrazol-1-yl]acetic acid (3.9 g, 95%).
log P (pH 2.7): 2.45
$^1$H NMR (DMSO-d$_6$, 400 MHz): δ$_{ppm}$: 1.26 (s, 9H), 4.95 (s, 2H), 6.76 (s, 1H)
MS (ESI): 251 ([M+H]$^+$)

[3-tert-Butyl-5-(pentafluoroethyl)-1H-pyrazol-1-yl]acetic acid (V-3)

Ethyl [3-tert-butyl-5-(pentafluoroethyl)-1H-pyrazol-1-yl]acetate (XVI-3, 2.50 g) is reacted analogously to Example V-1. This gives, after filtration and drying, [3-tert-butyl-5-(pentafluoroethyl)-1H-pyrazol-1-yl]acetic acid (1.8 g, 79%).
log P (pH 2.7): 2.92
$^1$H NMR (DMSO-d$_6$, 400 MHz): δ$_{ppm}$: 1.27 (s, 9H), 4.96 (s, 2H), 6.72 (s, 1H)
MS (ESI): 301 ([M+H]$^+$)

[5-tert-Butyl-3-(pentafluoroethyl)-1H-pyrazol-1-yl]acetic acid (V-4)

Ethyl [5-tert-butyl-3-(pentafluoroethyl)-1H-pyrazol-1-yl]acetate (XVI-4, 4.80 g) is reacted analogously to Example V-1. This gives, after filtration and drying, [5-tert-butyl-3-(pentafluoroethyl)-1H-pyrazol-1-yl]acetic acid (3.5 g, 80%).
log P (pH 2.7): 2.75
$^1$H NMR (DMSO-d$_6$, 400 MHz): δ$_{ppm}$: 1.33 (s, 9H), 5.09 (s, 2H), 6.45 (s, 1H)
MS (ESI): 301 ([M+H]$^+$)

[3-Isopropyl-5-(trifluoromethyl)-1H-pyrazol-1-yl]acetic acid (V-5)

Ethyl [3-isopropyl-5-(trifluoromethyl)-1H-pyrazol-1-yl]acetate (XVI-5, 26.2 g) is reacted analogously to Example V-1. This gives, after filtration and drying, [3-isopropyl-5-(trifluoromethyl)-1H-pyrazol-1-yl]acetic acid (22 g, 94%).
log P (pH 2.7): 2.05
$^1$H NMR (DMSO-d$_6$, 400 MHz): δ$_{ppm}$: 1.21 (d, 6H), 2.99 (septet, 1H), 4.99 (s, 2H), 6.51 (s, 1H)
MS (ESI): 237 ([M+H]$^+$)

[4-Chloro-5-methyl-3-(trifluoromethyl)-1H-pyrazol-1-yl]acetic acid (V-6)

Ethyl [4-chloro-5-methyl-3-(trifluoromethyl)-1H-pyrazol-1-yl]acetate (XVI-6, 18.0 g) is reacted analogously to Example V-1. This gives, after filtration and drying, [4-chloro-5-methyl-3-(trifluoromethyl)-1H-pyrazol-1-yl]acetic acid (15.5 g, 96%).
log P (pH 7.8): 0.68
$^1$H NMR (DMSO-d$_6$, 400 MHz): δ$_{ppm}$: 2.24 (s, 3H), 3.13 (bs, 1H), 5.04 (s, 2H)

PREPARATION OF STARTING MATERIALS OF THE FORMULA (VI)

4-[4-(Ethoxycarbonyl)-1,3-thiazol-2-yl]piperidinium chloride (VI-1)

Under argon and at 0° C., a 2-molar solution of hydrogen chloride in diethyl ether (370 ml) is added dropwise to a solution of tert-butyl 4-[4-(ethoxycarbonyl)-1,3-thiazol-2-yl]piperidine-1-carboxylate (25.0 g) in diethyl ether (200 ml). The reaction mixture is stirred at 0° C. and then slowly warmed to room temperature. After stirring overnight, the solvent and excess hydrogen chloride are removed. This gives 4-[4-(ethoxycarbonyl)-1,3-thiazol-2-yl]piperidinium chloride (20.0 g, 98%)
log P (pH 2.7): 0.42
$^1$H NMR (DMSO-d$_6$, 400 MHz): δ$_{ppm}$: 1.31 (t, 3H), 1.97-2.04 (m, 2H), 2.18-2.23 (m, 2H), 2.98-3.08 (m, 2H), 3.31-3.39 (m, 2H), 3.42 (m, 1H), 4.30 (q, 2H), 8.39 (s, 1H), 8.90 (bs, 1H), 9.13 (bs, 1H)
MS (ESI): 241 ([M-Cl]$^+$)

3-[4-(Ethoxycarbonyl)-1,3-thiazol-2-yl]piperidinium chloride (VI-2)

tert-Butyl 3-[4-(ethoxycarbonyl)-1,3-thiazol-2-yl]piperidine-1-carboxylate (13.8 g) is reacted analogously to Example VI-1. This gives 3-[4-(ethoxycarbonyl)-1,3-thiazol-2-yl]piperidinium chloride (10.4 g, 93%)
log P (pH 2.7): 0.54
$^1$H NMR (DMSO-d$_6$, 400 MHz): δ$_{ppm}$: 1.31 (t, 3H), 1.75-1.82 (m, 1H), 1.87-1.92 (m, 2H), 2.17-2.20 (m, 1H), 2.90-2.94 (m, 1H), 3.10-3.25 (m, 1H), 3.25-3.28 (m, 1H), 3.57 (m, 1H), 3.62 (m, 1H), 4.30 (q, 2H), 8.43 (s, 1H), 9.29-9.34 (m, 2H)
MS (ESI): 241 ([M-Cl]$^+$)

PREPARATION OF STARTING MATERIALS OF THE FORMULA (IV)

Ethyl 2-(1-{[3,5-bis(difluoromethyl)-1H-pyrazol-1-yl]acetyl}piperidin-4-yl)-1,3-thiazole-4-carboxylate (IV-1)

Oxalyl chloride (6.91 g) and a drop of N,N-dimethylformamide are added to a solution of [3,5-bis(difluoromethyl)-1H-pyrazol-1-yl]acetic acid (8.00 g) in dichloromethane (200 ml). The reaction mixture is stirred at room temperature overnight, and excess oxalyl chloride is then removed under reduced pressure. The residue is redissolved in dichloromethane (20 ml) and added to a solution of 4-[4-(ethoxycarbonyl)-1,3-thiazol-2-yl]piperidinium chloride (VI-1, 7.53 g) and Hünig base (10.6 g) in dichloromethane (80 ml). The reaction mixture is stirred at room temperature for 24 hours, added to a mixture of ice and water, neutralized with saturated bicarbonate solution and extracted with ethyl acetate. The combined organic phases are dried over sodium sulphate and concentrated under reduced pressure. The residue is purified chromatographically. This gives ethyl 2-(1-{[3,5-bis(difluoromethyl)-1H-pyrazol-1-yl]acetyl}piperidin-4-yl)-1,3-thiazole-4-carboxylate (10 g, 63%).
log P (pH 2.7): 2.52
$^1$H NMR (DMSO-d$_6$, 400 MHz): δ$_{ppm}$: 1.31 (t, 3H), 1.55-1.85 (m, 2H), 2.10 (m, 2H), 3.20-3.60 (m, 4H), 3.99 (bs, 1H), 4.30 (q, 2H), 5.35 (s, 2H), 6.83-7.30 (m, 3H), 8.37 (s, 1H)
MS (ESI): 449 ([M+H]$^+$)

Ethyl 2-(1-{[3-(trifluoromethyl)-1H-pyrazol-1-yl]acetyl}piperidin-4-yl)-1,3-thiazole-4-carboxylate (IV-2)

4-[4-(Ethoxycarbonyl)-1,3-thiazol-2-yl]piperidinium chloride (VI-1, 5.50 g) is reacted analogously to Example IV-1 with [3-(trifluoromethyl)-1H-pyrazol-1-yl]acetic acid (3.86 g). This gives, after chromatographic purification, ethyl 2-(1-{[3-(trifluoromethyl)-1H-pyrazol-1-yl]acetyl}piperidin-4-yl)-1,3-thiazole-4-carboxylate (5.1 g, 62%).
log P (pH 2.7): 2.41

¹H NMR (DMSO-d₆, 400 MHz): δ$_{ppm}$: 1.31 (t, 3H), 1.63 (bs, 1H), 1.75 (bs, 1H), 2.05-2.15 (m, 2H), 2.88 (bs, 1H), 3.26 (bs, 1H), 3.36 (m, 1H), 3.98 (bs, 1H), 4.30 (q, 2H), 4.35 (bs, 1H), 5.28 (s, 2H), 6.67 (d, 1H), 7.85 (dd, 1H), 8.36 (s, 1H)
MS (ESI): 417 ([M+H]⁺)

Ethyl 2-(1-{[5-methyl-3-(trifluoromethyl)-1H-pyrazol-1-yl]acetyl}piperidin-3-yl)-1,3-thiazole-4-carboxylate (IV-3)

3-[4-(Ethoxycarbonyl)-1,3-thiazol-2-yl]piperidinium chloride (VI-2, 5.32 g) is reacted analogously to Example IV-1 with [5-methyl-3-(trifluoromethyl)-1H-pyrazol-1-yl] acetic acid (4.00 g). This gives, after chromatographic purification, ethyl 2-(1-{[5-methyl-3-(trifluoromethyl)-1H-pyrazol-1-yl]acetyl}piperidin-3-yl)-1,3-thiazole-4-carboxylate (5.7 g, 69%).
log P (pH 2.7): 2.78
¹H NMR (DMSO-d₆, 400 MHz): δ$_{ppm}$: 1.29 (t, 3H), 1.50-1.74 (m, 2H), 1.79-1.89 (m, 2H), 2.20 (s, 3H), 3.18 (m, 1H), 3.39 (m, 0.5H), 3.69 (m, 0.5H), 3.86-3.89 (m, 1H), 4.00 (m, 0.5H), 4.30 (q, 2H), 4.45 (m, 0.5H), 4.90 (m, 1H), 5.25-5.30 (m, 2H), 6.44 (s, 1H), 8.40 (s, 1H)
MS (ESI): 431 ([M+H]⁺)

Ethyl 2-{1-[2-(3,5-dimethyl-1H-pyrazol-1-yl)-2-methylpropanoyl]piperidin-4-yl}-1,3-thiazole-4-carboxylate (IV-4)

4-[4-(Ethoxycarbonyl)-1,3-thiazol-2-yl]piperidinium chloride (VI-1, 8.23 g) is reacted analogously to Example IV-1 with 2-(3,5-dimethyl-1H-pyrazol-1-yl)-2-methylpropanoic acid (5.42 g). This gives, after chromatographic purification, ethyl 2-{1-[2-(3,5-dimethyl-1H-pyrazol-1-yl)-2-methylpropanoyl]piperidin-4-yl}-1,3-thiazole-4-carboxylate (9.64 g, 80%)
log P (pH 7.8): 2.34
¹H NMR (DMSO-d₆, 400 MHz): δ$_{ppm}$: 1.29 (t, 3H), 1.41 (m, 2H), 1.66 (s, 6H), 1.90 (m, 2H), 2.11 (s, 3H), 2.12 (s, 3H), 2.81 (m, 2H), 3.22 (m, 1H), 3.59 (m, 1H), 4.10 (m, 1H), 4.28 (q, 2H), 5.89 (s, 1H), 8.32 (s, 1H)
MS (ESI): 405 ([M+H]⁺)

Ethyl 2-(1-{[5-methyl-3-(trifluoromethyl)-1H-pyrazol-1-yl]acetyl}piperidin-4-yl)-1,3-thiazole-4-carboxylate (IV-5)

4-[4-(Ethoxycarbonyl)-1,3-thiazol-2-yl]piperidinium chloride (VI-1, 4.65 g) is reacted analogously to Example IV-1 with [5-methyl-3-(trifluoromethyl)-1H-pyrazol-1-yl] acetic acid (3.50 g). This gives, after chromatographic purification, ethyl 2-(1-{[5-methyl-3-(trifluoromethyl)-1H-pyrazol-1-yl]acetyl}piperidin-4-yl)-1,3-thiazole-4-carboxylate (5.00 g, 69%).
log P (pH 2.7): 2.62
¹H NMR (DMSO-d₆, 400 MHz): δ$_{ppm}$: 1.31 (t, 3H), 1.62 (bs, 1H), 1.80 (bs, 1H), 2.06-2.16 (m, 2H), 2.22 (s, 3H), 2.88 (bs, 1H), 3.28 (bs, 1H), 3.37 (m, 1H), 3.99 (bs, 1H), 4.30 (q, 2H), 4.33 (bs, 1H), 5.22 (bs, 2H), 6.45 (s, 1H), 8.37 (s, 1H)
MS (ESI): 431 ([M+H]⁺)

Ethyl 2-(1-{[4-chloro-5-methyl-3-(trifluoromethyl)-1H-pyrazol-1-yl]acetyl}piperidin-4-yl)-1,3-thiazole-4-carboxylate (IV-6)

4-[4-(Ethoxycarbonyl)-1,3-thiazol-2-yl]piperidinium chloride (VI-1, 5.50 g) is reacted analogously to Example IV-1 with [4-chloro-5-methyl-3-(trifluoromethyl)-1H-pyrazol-1-yl]acetic acid (4.82 g). This gives, after chromatographic purification, ethyl 2-(1-{[4-chloro-5-methyl-3-(trifluoromethyl)-1H-pyrazol-1-yl]acetyl}piperidin-4-yl)-1,3-thiazole-4-carboxylate (6.00 g, 65%).
log P (pH 2.7): 3.17
¹H NMR (DMSO-d₆, 400 MHz): δ$_{ppm}$: 1.31 (t, 3H), 1.61 (bs, 1H), 1.81 (bs, 1H), 2.05-2.15 (m, 2H), 2.20 (s, 3H), 2.88 (bs, 1H), 3.27 (bs, 1H), 3.37 (m, 1H), 3.95 (bs, 1H), 4.30 (q, 2H), 4.32 (bs, 1H), 5.27-5.35 (3, 2H), 8.37 (s, 1H)
MS (ESI): 465 ([M+H]⁺)

PREPARATION OF STARTING MATERIALS OF THE FORMULA (III)

2-(1-{[3,5-Bis(difluoromethyl)-1H-pyrazol-1-yl] acetyl}piperidin-4-yl)-1,3-thiazole-4-carboxylic acid (III-1)

Ethyl 2-(1-{[3,5-bis(difluoromethyl)-1H-pyrazol-1-yl] acetyl}piperidin-4-yl)-1,3-thiazole-4-carboxylate (IV-1, 13.3 g) is dissolved in tetrahydrofuran (80 ml). LiOH monohydrate (1.86 g) dissolved in water (20 ml) is then added. After 3 hours, water is added, the pH is adjusted to 2-3 with dilute hydrochloric acid (1M), the mixture is then extracted with ethyl acetate and the combined organic phases are dried with sodium sulfate. The solid is filtered off and the solvent is removed by distillation. This gives 2-(1-{[3,5-bis(difluoromethyl)-1H-pyrazol-1-yl]acetyl}piperidin-4-yl)-1,3-thiazole-4-carboxylic acid (11.7 g, 94%).
log P (pH 2.7): 1.71
¹H NMR (DMSO-d₆, 400 MHz): δ$_{ppm}$: 1.55-1.85 (m, 2H), 2.09-2.13 (m, 2H), 2.80-3.30 (m, 3H), 3.36 (m, 1H), 3.99 (bs, 1H), 4.30 (bs, 1H), 5.34 (s, 2H), 6.85 (s, 1H), 6.98 (t, 1H), 7.14 (t, 1H), 8.29 (s, 1H)
MS (ESI): 421 ([M+H]⁺)

2-(1-{[3-(Trifluoromethyl)-1H-pyrazol-1-yl] acetyl}piperidin-4-yl)-1,3-thiazole-4-carboxylic acid (III-2)

Ethyl 2-(1-{[3-(trifluoromethyl)-1H-pyrazol-1-yl] acetyl}piperidin-4-yl)-1,3-thiazole-4-carboxylate (IV-2, 5.20 g) is reacted analogously to Example III-1. This gives, after drying, 2-(1-{[3-(trifluoromethyl)-1H-pyrazol-1-yl] acetyl}piperidin-4-yl)-1,3-thiazole-4-carboxylic acid (4.6 g, 95%).
log P (pH 2.7): 1.65
¹H NMR (DMSO-d₆, 400 MHz): δ$_{ppm}$: 1.64 (bs, 1H), 1.76 (bs, 1H), 2.05-2.15 (m, 2H), 2.88 (bs, 1H), 3.23 (bs, 1H), 3.36 (m, 1H), 3.98 (bs, 1H), 4.34 (bs, 1H), 5.28 (s, 2H), 6.67 (d, 1H), 7.85 (dd, 1H), 8.29 (s, 1H)
MS (ESI): 389 ([M+H]⁺)

2-(1-{[5-Methyl-3-(trifluoromethyl)-1H-pyrazol-1-yl]acetyl}piperidin-3-yl)-1,3-thiazole-4-carboxylic acid (III-3)

Ethyl 2-(1-{[5-methyl-3-(trifluoromethyl)-1H-pyrazol-1-yl]acetyl}piperidin-3-yl)-1,3-thiazole-4-carboxylate (IV-3, 5.70 g) is reacted analogously to Example III-1. This gives, after drying, 2-(1-{[5-methyl-3-(trifluoromethyl)-1H-pyrazol-1-yl]acetyl}piperidin-3-yl)-1,3-thiazole-4-carboxylic acid (5.4 g, 100%).
log P (pH 2.7): 1.90

¹H NMR (DMSO-d₆, 400 MHz): $\delta_{ppm}$: 1.48-1.88 (m, 4H), 2.20 (s, 3H), 3.38 (m, 0.5H), 3.60 (m, 0.5H), 3.87 (m, 2H), 4.01 (m, 0.5H), 4.45 (m, 0.5H), 5.24-5.28 (m, 3H), 6.44 (s, 1H), 8.32 (s, 1H)

MS (ESI): 403 ([M+H]⁺)

2-(1-{[5-Methyl-3-(trifluoromethyl)-1H-pyrazol-1-yl]acetyl}piperidin-4-yl)-1,3-thiazole-4-carboxylic acid (III-4)

Ethyl 2-(1-{[5-methyl-3-(trifluoromethyl)-1H-pyrazol-1-yl]acetyl}piperidin-5-yl)-1,3-thiazole-4-carboxylate (IV-3, 5.10 g) is reacted analogously to Example III-1. This gives, after drying, 2-(1-{[5-methyl-3-(trifluoromethyl)-1H-pyrazol-1-yl]acetyl}piperidin-4-yl)-1,3-thiazole-4-carboxylic acid (4.63 g, 97%).

log P (pH 2.7): 1.82

¹H NMR (DMSO-d₆, 400 MHz): $\delta_{ppm}$: 1.62 (bs, 1H), 1.79 (bs, 1H), 2.06-2.16 (m, 2H), 2.22 (s, 3H), 2.88 (bs, 1H), 3.28 (bs, 1H), 3.37 (m, 1H), 3.99 (bs, 1H), 4.33 (bs, 1H), 5.21 (bs, 2H), 6.45 (d, 1H), 8.30 (s, 1H)

MS (ESI): 403 ([M+H]⁺)

2-(1-{[4-Chloro-5-methyl-3-(trifluoromethyl)-1H-pyrazol-1-yl]acetyl}piperidin-4-yl)-1,3-thiazole-4-carboxylic acid (III-5)

Ethyl 2-(1-{[4-chloro-5-methyl-3-(trifluoromethyl)-1H-pyrazol-1-yl]acetyl}piperidin-5-yl)-1,3-thiazole-4-carboxylate (IV-6, 6.00 g) is reacted analogously to Example III-1. This gives, after drying, 2-(1-{[4-chloro-5-methyl-3-(trifluoromethyl)-1H-pyrazol-1-yl]acetyl}piperidin-4-yl)-1,3-thiazole-4-carboxylic acid (3.10 g, 55%).

log P (pH 2.7): 2.26

¹H NMR (DMSO-d₆, 400 MHz): $\delta_{ppm}$: 1.61 (bs, 1H), 1.81 (bs, 1H), 2.05-2.17 (m, 2H), 2.20 (s, 3H), 2.89 (bs, 1H), 3.27 (bs, 1H), 3.37 (m, 1H), 3.95 (bs, 1H), 4.32 (bs, 1H), 5.27-5.34 (m, 2H), 8.29 (s, 1H)

MS (ESI): 437 ([M+H]⁺)

PREPARATION OF THE COMPOUNDS OF THE FORMULA (I)

Cyclohexyl 2-(1-{[3,5-bis(difluoromethyl)-1H-pyrazol-1-yl]acetyl}piperidin-4-yl)-1,3-thiazole-4-carboxylate (I-811)

At room temperature, cyclohexanol (2.17 g), dimethylaminopyridine (0.20 g) and 1-ethyl-3-(3'-dimethylaminopropyl)carbodiimide (3.35 g) are added to a solution of 2-(1-{[3,5-bis(difluoromethyl)-1H-pyrazol-1-yl]acetyl}piperidin-4-yl)-1,3-thiazole-4-carboxylic acid (III-1, 7.00 g) in dichloromethane (80 ml). The mixture is stirred overnight, and water is then added. The aqueous phase is separated off and extracted with ethyl acetate. The combined organic phases are dried with sodium sulfate. The solid is filtered off and the solvent is removed by distillation. The residue is purified chromatographically. This gives cyclohexyl 2-(1-{[3,5-bis(difluoromethyl)-1H-pyrazol-1-yl]acetyl}piperidin-4-yl)-1,3-thiazole-4-carboxylate (2.83 g, 34%).

log P (pH 2.7): 3.64

¹H NMR (DMSO-d₆, 400 MHz): $\delta_{ppm}$: 1.29-1.90 (m, 12H), 2.09-2.12 (m, 2H), 2.88 (bs, 1H), 3.25 (bs, 1H), 3.39 (m, 1H), 4.01 (bs, 1H), 4.30 (bs, 1H), 4.88-4.93 (m, 1H), 5.35 (s, 2H), 6.85 (s, 1H), 6.96 (t, 1H), 7.14 (t, 1H), 8.34 (s, 1H)

MS (ESI): 503 ([M+H]⁺)

1-Naphthyl 2-(1-{[3,5-bis(difluoromethyl)-1H-pyrazol-1-yl]acetyl}piperidin-4-yl)-1,3-thiazole-4-carboxylate (I-813)

2-(1-{[3,5-Bis(difluoromethyl)-1H-pyrazol-1-yl]acetyl}piperidin-4-yl)-1,3-thiazole-4-carboxylic acid (III-1, 7.00 g) is reacted analogously to Example I-811 with 1-naphthol (3.12 g). This gives, after chromatographic purification, 1-naphthyl-2-(1-{[3,5-bis(difluoromethyl)-1H-pyrazol-1-yl]acetyl}piperidin-4-yl)-1,3-thiazole-4-carboxylate (4.0 g, 44%).

log P (pH 2.7): 3.64

¹H NMR (DMSO-d₆, 400 MHz): $\delta_{ppm}$: 1.70 (bs, 1H), 1.87 (bs, 1H), 2.18 (m, 2H), 2.91 (bs, 1H), 3.31 (bs, 1H), 3.48 (m, 1H), 4.03 (bs, 1H), 4.36 (bs, 1H), 5.36 (s, 2H), 6.85 (s, 1H), 6.97 (t, 1H), 7.15 (t, 1H), 7.45 (dd, 1H), 7.54-7.61 (m, 3H), 7.89 (m, 2H), 8.01 (m, 1H), 8.84 (s, 1H)

MS (ESI): 547 ([M+H]⁺)

1-Naphthyl 2-(1-{[5-methyl-3-(trifluoromethyl)-1H-pyrazol-1-yl]acetyl}piperidin-4-yl)-1,3-thiazole-4-carboxylate (I-227)

Oxalyl chloride (189 mg) and a drop of N,N-dimethylformamide are added to a solution of 2-(1-{[5-methyl-3-(trifluoromethyl)-1H-pyrazol-1-yl]acetyl}piperidin-4-yl)-1,3-thiazole-4-carboxylic acid (III-4, 200 mg) in dichloromethane (2 ml). The reaction mixture is stirred at room temperature overnight, and excess oxalyl chloride is then removed under reduced pressure. The residue is re-dissolved in dichloromethane (2 ml) and added to a solution of 1-naphthol (79 mg) and pyridine (489 mg) in dichloromethane (4 ml). The mixture is stirred at room temperature for one hour, and dilute hydrochloric acid (1M) is then added. The aqueous phase is separated off and extracted with ethyl acetate, and the combined organic phases are then dried with sodium sulfate. The solid is filtered off and the solvent is removed by distillation. The residue is purified chromatographically. This gives 1-naphthyl 2-(1-{[5-methyl-3-(trifluoromethyl)-1H-pyrazol-1-yl]acetyl}piperidin-4-yl)-1,3-thiazole-4-carboxylate (100 mg, 38%).

log P (pH 2.7): 3.75

¹H NMR (CD₃CN, 400 MHz): $\delta_{ppm}$: 1.72-2.00 (m, 2H), 2.19-2.27 (m, 2H), 2.24 (s, 3H), 2.92 (bs, 1H), 3.34 (bs, 1H), 3.42 (m, 1H), 3.98 (bs, 1H), 4.49 (bs, 1H), 5.06 (bs, 2H), 6.37 (s, 1H), 7.40 (d, 1H), 7.52-7.60 (m, 3H), 7.86 (d, 1H), 7.92-7.99 (m, 2H), 8.55 (s, 1H)

MS (ESI): 529 ([M+H]⁺)

1,2,3,4-Tetrahydronaphthalen-1-yl 2-(1-{[5-methyl-3-(trifluoromethyl)-1H-pyrazol-1-yl]acetyl}piperidin-4-yl)-1,3-thiazole-4-carboxylate (I-224)

At room temperature, 1,2,3,4-tetrahydronaphthalen-1-ol (155 mg) and triphenylphosphine (758 mg) are added to a solution of 2-(1-{[5-methyl-3-(trifluoromethyl)-1H-pyrazol-1-yl]acetyl}piperidin-4-yl)-1,3-thiazole-4-carboxylic acid (III-4, 380 mg) in tetrahydrofuran (2.5 ml). The mixture is stirred at 0 C under argon for 5 minutes, and diethyldiazene 1,2-dicarboxylate (383 mg) is then added dropwise. The reaction mixture is slowly warmed to room temperature. After 2 hours, the solvent is removed under reduced pressure and the residue is purified chromatographically. This gives 1,2,3,4-tetrahydronaphthalen-1-yl 2-(1-{[5-methyl-3-(trifluoromethyl)-1H-pyrazol-1-yl]acetyl}piperidin-4-yl)-1,3-thiazole-4-carboxylate (196 mg, 39%).

log P (pH 2.7): 4.01

$^1$H NMR (DMSO-d$_6$, 400 MHz): $\delta_{ppm}$: 1.52-1.88 (m, 3H), 1.88-2.15 (m, 4H), 2.22 (s, 3H), 2.70-2.99 (m, 4H), 3.25 (bs, 1H), 3.38 (m, 1H), 3.98 (bs, 1H), 4.33 (bs, 1H), 5.21 (bs, 2H), 6.12 (t, 1H), 6.44 (s, 1H), 7.15-7.19 (m, 2H), 7.21-7.30 (m, 2H), 8.35 (s, 1H)

MS (ESI): 403 ([M+H-1,2,3,4-tetrahydronaphthalen-1-ol]$^+$)

Cyclohexyl 2-(1-{[5-methyl-3-(trifluoromethyl)-1H-pyrazol-1-yl]acetyl}piperidin-4-yl)-1,3-thiazole-4-carboxylate (I-220)

A solution of 2-(1-{[5-methyl-3-(trifluoromethyl)-1H-pyrazol-1-yl]acetyl}piperidin-4-yl)-1,3-thiazole-4-carboxylic acid (III-4, 6.00 g) is reacted analogously to Example I-811 with cyclohexanol (1.94 g). This gives, after chromatographic purification, cyclohexyl 2-(1-{[5-methyl-3-(trifluoromethyl)-1H-pyrazol-1-yl]acetyl}piperidin-4-yl)-1,3-thiazole-4-carboxylate (5.00 g, 69%).

log P (pH 2.7): 3.74

$^1$H NMR (DMSO-d$_6$, 400 MHz): $\delta_{ppm}$: 1.25-1.48 (m, 3H), 1.50-2.00 (broad m, 2H), 1.50-1.51 (m, 3H), 1.70-1.80 (m, 2H), 1.85-1.92 (m, 2H), 2.06-2.16 (m, 2H), 2.22 (s, 3H), 2.88 (bs, 1H), 3.28 (bs, 1H), 3.38 (m, 1H), 3.98 (bs, 1H), 4.34 (bs, 1H), 4.91 (septet, 1H), 5.21 (bs, 2H), 6.44 (s, 1H), 8.34 (s, 1H)

MS (ESI): 485 ([M+H]$^+$)

2-Bromobenzyl 2-(1-{[5-methyl-3-(trifluoromethyl)-1H-pyrazol-1-yl]acetyl}piperidin-4-yl)-1,3-thiazole-4-carboxylate (I-820)

A solution of 2-(1-{[5-methyl-3-(trifluoromethyl)-1H-pyrazol-1-yl]acetyl}piperidin-4-yl)-1,3-thiazole-4-carboxylic acid (III-4, 100 mg) is reacted analogously to Example I-811 with (2-bromophenyl)methanol (49.0 mg). This gives, after chromatographic purification, 2-bromobenzyl 2-(1-{[5-methyl-3-(trifluoromethyl)-1H-pyrazol-1-yl]acetyl}piperidin-4-yl)-1,3-thiazole-4-carboxylate (123 mg, 89%).

log P (pH 2.7): 3.80

$^1$H NMR (DMSO-d$_6$, 400 MHz): $\delta_{ppm}$: 1.62 (bs, 1H), 1.80 (bs, 1H), 2.07-2.19 (m, 2H), 2.22 (s, 3H), 2.88 (bs, 1H), 3.27 (bs, 1H), 3.38 (m, 1H), 3.99 (bs, 1H), 4.43 (bs, 1H), 5.22 (bs, 2H), 5.38 (s, 2H), 6.44 (s, 1H), 7.32 (td, 1H), 7.43 (td, 1H), 7.56 (dd, 1H), 7.67 (dd, 1H), 8.46 (s, 1H)

MS (ESI): 571, 573 ([M+H]$^+$)

3,3-Dimethylbutyl 2-(1-{[3-(trifluoromethyl)-1H-pyrazol-1-yl]acetyl}piperidin-4-yl)-1,3-thiazole-4-carboxylate (I-767)

A solution of 2-(1-{[3-(trifluoromethyl)-1H-pyrazol-1-yl]acetyl}piperidin-4-yl)-1,3-thiazole-4-carboxylic acid (III-2, 200 mg) is reacted analogously to Example I-811 with 3,3-dimethylbutan-1-ol (68.0 mg). This gives, after chromatographic purification, 3,3-dimethylbutyl 2-(1-{[3-(trifluoromethyl)-1H-pyrazol-1-yl]acetyl}piperidin-4-yl)-1,3-thiazole-4-carboxylate (98 mg, 40%).

log P (pH 2.7): 3.82

$^1$H NMR (DMSO-d$_6$, 400 MHz): $\delta_{ppm}$: 0.96 (s, 9H), 1.50-1.85 (broad m+t, 4H), 2.06-2.13 (m, 2H), 2.88 (bs, 1H), 3.28 (bs, 1H), 3.38 (m, 1H), 3.98 (bs, 1H), 4.31 (t, 2H), 4.34 (bs, 1H), 5.28 (bs, 2H), 6.66 (d, 1H), 7.85 (s, 1H), 8.34 (s, 1H)

MS (ESI): 473 ([M+H]$^+$)

S-(4-Fluorobenzyl) 2-(1-{[5-methyl-3-(trifluoromethyl)-1H-pyrazol-1-yl]acetyl}piperidin-4-yl)-1,3-thiazole-4-carbothioate (I-27)

A solution of 2-(1-{[5-methyl-3-(trifluoromethyl)-1H-pyrazol-1-yl]acetyl}piperidin-4-yl)-1,3-thiazole-4-carboxylic acid (III-4, 200 mg) is reacted analogously to Example I-227 with (4-fluorophenyl)methanethiol (78.0 mg). This gives, after chromatographic purification, S-(4-fluorobenzyl) 2-(1-{[5-methyl-3-(trifluoromethyl)-1H-pyrazol-1-yl]acetyl}piperidin-4-yl)-1,3-thiazole-4-carbothioate (110 mg, 42%).

log P (pH 2.7): 4.00

$^1$H NMR (CD$_3$CN, 400 MHz): $\delta_{ppm}$: 1.64-1.88 (broad m, 2H), 2.12-2.18 (m, 2H), 2.23 (s, 3H), 2.92 (bs, 1H), 3.30 (bs, 1H), 3.33 (m, 1H), 3.97 (bs, 1H), 4.24 (s, 2H), 4.41 (bs, 1H), 5.04 (bs, 2H), 6.36 (s, 1H), 7.00-7.07 (m, 2H), 7.36-7.42 (m, 2H), 8.11 (s, 1H)

MS (ESI): 527 ([M+H]$^+$)

S-Cyclohexyl 2-(1-{[5-methyl-3-(trifluoromethyl)-1H-pyrazol-1-yl]acetyl}piperidin-4-yl)-1,3-thiazole-4-carbothioate (I-76)

A solution of 2-(1-{[5-methyl-3-(trifluoromethyl)-1H-pyrazol-1-yl]acetyl}piperidin-4-yl)-1,3-thiazole-4-carboxylic acid (III-4, 200 mg) is reacted analogously to Example I-227 with cyclohexanethiol (64.0 mg). This gives, after chromatographic purification, S-cyclohexyl 2-(1-{[5-methyl-3-(trifluoromethyl)-1H-pyrazol-1-yl]acetyl}piperidin-4-yl)-1,3-thiazole-4-carbothioate (110 mg, 44%).

log P (pH 2.7): 4.51

$^1$H NMR (CD$_3$CN, 400 MHz): $\delta_{ppm}$: 1.30-1.40 (m, 2H), 1.42-1.90 (m, 10H), 2.12-2.19 (m, 2H), 2.24 (s, 3H), 2.91 (bs, 1H), 3.30 (bs, 1H), 3.34 (m, 1H), 3.65 (m, 1H), 3.95 (bs, 1H), 4.44 (bs, 1H), 5.04 (bs, 2H), 6.36 (s, 1H), 8.05 (s, 1H)

MS (ESI): 501 ([M+H]$^+$)

S-1-Naphthyl 2-(1-{[5-methyl-3-(trifluoromethyl)-1H-pyrazol-1-yl]acetyl}piperidin-4-yl)-1,3-thiazole-4-carbothioate (I-77)

A solution of 2-(1-{[5-methyl-3-(trifluoromethyl)-1H-pyrazol-1-yl]acetyl}piperidin-4-yl)-1,3-thiazole-4-carboxylic acid (III-4, 200 mg) is reacted analogously to Example I-227 with naphthalene-1-thiol (88.0 mg). This gives, after chromatographic purification, S-1-naphthyl 2-(1-{[5-methyl-3-(trifluoromethyl)-1H-pyrazol-1-yl]acetyl}piperidin-4-yl)-1,3-thiazole-4-carbothioate (100 mg, 37%).

log P (pH 2.7): 4.22

$^1$H NMR (CD$_3$CN, 400 MHz): $\delta_{ppm}$: 1.74-1.90 (m, 2H), 2.20-2.26 (m, 2H), 2.25 (s, 3H), 2.93 (bs, 1H), 3.34 (bs, 1H), 3.42 (m, 1H), 4.04 (bs, 1H), 4.48 (bs, 1H), 5.07 (bs, 2H), 6.37 (s, 1H), 7.54-7.60 (m, 3H), 7.80 (dd, 1H), 7.98 (dd, 1H), 8.05 (d, 1H), 8.13 (s, 1H), 8.20 (dd, 1H)

MS (ESI): 545 ([M+H]$^+$)

PREPARATION OF STARTING MATERIALS OF THE FORMULA (VIII)

2-[1-(tert-Butoxycarbonyl)piperidin-4-yl]-1,3-thiazole-4-carboxylic acid (VIII-1)

At room temperature, lithium hydroxide monohydrate (8.88 g) is added in one portion to a solution of tert-butyl 4-[4-(ethoxycarbonyl)-1,3-thiazol-2-yl]piperidine-1-carboxylate (24.0 g) in tetrahydrofuran (240 ml) and water (60 ml). The mixture is stirred for 4 hours and then stirred with dilute hydrochloric acid (1M) (100 ml) and ethyl acetate (100 ml). The aqueous phase is separated off and extracted with ethyl acetate, and the combined organic phases are then dried with sodium sulfate. The solid is filtered off and the solvent is removed by distillation. This gives 2-[1-(tert-Butoxycarbonyl)piperidin-4-yl]-1,3-thiazole-4-carboxylic acid (21 g, 94%)

log P (pH 2.7): 2.04

$^1$H NMR (DMSO-d$_6$, 400 MHz): $\delta_{ppm}$: 1.41 (s, 9H), 1.59 (qd, 2H), 2.02 (dd, 2H), 2.91 (m, 2H), 3.23 (m, 1H), 3.97-4.02 (m, 2H), 8.27 (s, 1H)

MS (ESI): 256 ([M+H—C(CH$_3$)$_3$]$^+$)

PREPARATION OF STARTING MATERIALS OF THE FORMULA (IX)

tert-Butyl 4-{4-[(cyclohexyloxy)carbonyl]-1,3-thiazol-2-yl}piperidine-1-carboxylate (IX-1)

At room temperature, cyclohexanol (1.21 g), dimethylaminopyridine (113 mg) and 1-ethyl-3-(3'-dimethylaminopropyl)carbodiimide (1.87 g) are added to a solution of 2-[1-(tert-butoxycarbonyl)piperidin-4-yl]-1,3-thiazole-4-carboxylic acid (VIII-1, 2.90 g) in dichloromethane (30 ml). The mixture is stirred at room temperature overnight, and water is then added. The aqueous phase is separated off and extracted with ethyl acetate, and the combined organic phases are then dried with sodium sulfate. The solid is filtered off and the solvent is removed by distillation. The residue is purified chromatographically. This gives tert-butyl 4-{4-[(cyclohexyloxy)carbonyl]-1,3-thiazol-2-yl}piperidine-1-carboxylate (2.63 g, 72%)

log P (pH 2.7): 4.62

$^1$H NMR (DMSO-d$_6$, 400 MHz): $\delta_{ppm}$: 1.13-1.81 (m+s, 21H), 2.02 (m, 2H), 2.90 (m, 2H), 3.40 (m, 1H), 3.98-4.01 (m, 2H), 4.90 (m, 1H), 8.32 (s, 1H)

MS (ESI): 339 ([M+2H—C(CH$_3$)$_3$]$^+$)

tert-Butyl 4-{4-[(1-naphthyloxy)carbonyl]-1,3-thiazol-2-yl}piperidine-1-carboxylate (IX-2)

A solution of 2-[1-(tert-butoxycarbonyl)piperidin-4-yl]-1,3-thiazole-4-carboxylic acid (VIII-1, 12.0 g) is reacted analogously to Example IX-1 with 1-naphthol (7.20 g). This gives, after chromatographic purification, tert-butyl 4-{4-[(1-naphthyloxy)carbonyl]-1,3-thiazol-2-yl}piperidine-1-carboxylate (12.3 g, 73%)

log P (pH 2.7): 4.50

$^1$H NMR (DMSO-d$_6$, 400 MHz): $\delta_{ppm}$: 1.42 (s, 9H), 1.67 (qd, 2H), 2.10 (dd, 2H), 2.95 (m, 2H), 3.35 (m, 1H), 4.00-4.08 (m, 2H), 7.45 (dd, 1H), 7.55-7.62 (m, 3H), 7.89 (d, 2H), 8.01 (dd, 1H), 8.83 (s, 1H)

MS (ESI): 383 ([M+2H—C(CH$_3$)$_3$]$^+$)

PREPARATION OF STARTING MATERIALS OF THE FORMULA (X)

4-{4-[(Cyclohexyloxy)carbonyl]-1,3-thiazol-2-yl}piperidinium chloride (X-1)

Under argon and at 0° C., a 2-molar solution of hydrogen chloride in diethyl ether (50 ml) is added dropwise to a solution of tert-butyl 4-{4-[(cyclohexyloxy)carbonyl]-1,3-thiazol-2-yl}piperidine-1-carboxylate (IX-1, 2.63 g) in dioxane (20 ml). The reaction mixture is stirred at 0° C. and then slowly warmed to room temperature. After stirring overnight, the solvent and excess hydrogen chloride are removed. This gives 4-{4-[(cyclohexyloxy)carbonyl]-1,3-thiazol-2-yl}piperidinium chloride (2.19 g, 99%)

log P (pH 2.7): 1.25

$^1$H NMR (DMSO-d$_6$, 400 MHz): $\delta_{ppm}$: 1.15-1.55 (m, 6H), 1.71-1.75 (m, 2H), 1.85-1.90 (m, 2H), 1.98-2.04 (m, 2H), 2.20 (dd, 2H), 3.01-3.03 (m, 2H), 3.14-3.34 (m, 2H), 3.40 (m, 1H), 4.90 (m, 1H), 8.36 (s, 1H), 9.05 (bs, 1H), 9.25 (bs, 1H)

MS (ESI): 295 ([M−Cl]$^+$)

4-{4-[(1-Naphthyloxy)carbonyl]-1,3-thiazol-2-yl}piperidinium chloride (X-2)

tert-Butyl 4-{4-[(1-naphthyloxy)carbonyl]-1,3-thiazol-2-yl}piperidine-1-carboxylate (IX-2, 3.20 g) is reacted analogously to Example X-1. This gives, after drying, 4-{4-[(1-naphthyloxy)carbonyl]-1,3-thiazol-2-yl}piperidinium chloride (2.93 g, 100%)

log P (pH 2.7): 1.42

$^1$H NMR (DMSO-d$_6$, 400 MHz): $\delta_{ppm}$: 2.02-2.15 (m, 2H), 2.25-2.34 (m, 2H), 3.00-3.12 (m, 2H), 3.34-3.40 (m, 2H), 3.51 (m, 1H), 7.46 (dd, 1H), 7.53-7.62 (m, 3H), 7.89 (d, 2H), 8.00-5.05 (m, 1H), 8.87 (s, 1H), 9.05 (bs, 1H), 9.25 (bs, 1H)

MS (ESI): 339 ([M−Cl]$^+$)

PREPARATION OF THE COMPOUNDS OF THE FORMULA (I)

Cyclohexyl 2-(1-{[3,5-bis(trifluoromethyl)-1H-pyrazol-1-yl]acetyl}piperidin-4-yl)-1,3-thiazole-4-carboxylate (I-772)

[3,5-Bis(trifluoromethyl)-1H-pyrazol-1-yl]acetic acid (288 mg) and Hünig base (323 mg) are dissolved in dichloromethane (10 ml) and stirred at room temperature for 30 min. 4-{4-[(Cyclohexyloxy)carbonyl]-1,3-thiazol-2-yl}piperidinium chloride (X-1, 330 mg) is added, and the mixture is stirred for a further 5 min before bromo-tris-pyrrolidinophosphonium hexafluorophosphate (559 mg) is added. The reaction mixture is stirred at room temperature overnight. After removal of the solvent under reduced pressure, the residue is purified chromatographically. This gives cyclohexyl 2-(1-{[3,5-bis(trifluoromethyl)-1H-pyrazol-1-yl]acetyl}piperidin-4-yl)-1,3-thiazole-4-carboxylate (348 mg, 65%).

log P (pH 2.7): 4.39

$^1$H NMR (DMSO-d$_6$, 400 MHz): $\delta_{ppm}$: 1.20-1.60 (m, 8H), 1.71-1.75 (m, 2H), 1.85-1.88 (m, 2H), 2.04 (m, 2H), 2.90 (bs, 1H), 3.30 (bs, 1H), 3.38 (m, 1H), 3.95 (bs, 1H), 4.30 (bs, 1H), 4.91 (m, 1H), 5.48 (bs, 2H), 7.47 (s, 1H), 8.34 (s, 1H)

MS (ESI): 539 ([M+H]$^+$)

1-Naphthyl 2-(1-{[3,5-bis(trifluoromethyl)-1H-pyrazol-1-yl]acetyl}piperidin-4-yl)-1,3-thiazole-4-carboxylate (I-771)

4-{4-[(1-Naphthyloxy)carbonyl]-1,3-thiazol-2-yl}piperidinium chloride (X-2, 375 mg) is reacted analogously to Example I-772 with [3,5-bis(trifluoromethyl)-1H-pyrazol-1-yl]acetic acid (288 mg). This gives, after chromatographic purification, 1-naphthyl 2-(1-{[3,5-bis(trifluoromethyl)-1H-pyrazol-1-yl]acetyl}piperidin-4-yl)-1,3-thiazole-4-carboxylate (356 mg, 61%).

log P (pH 2.7): 4.35

$^1$H NMR (DMSO-d$_6$, 400 MHz): δ$_{ppm}$: 1.65 (m, 1H), 1.90 (m, 1H), 2.19 (m, 2H), 2.95 (m, 1H), 3.32 (m, 1H), 3.48 (m, 1H), 4.01 (m, 1H), 4.35 (m, 1H), 5.50 (m, 2H), 7.45 (m, 2H), 7.56-7.61 (m, 3H), 7.89 (m, 2H), 8.02 (m, 1H), 8.84 (s, 1H)

MS (ESI): 583 ([M+H]$^+$)

1-Naphthyl 2-(1-{[3,5-bis(difluoromethyl)-1H-pyrazol-1-yl]acetyl}piperidin-4-yl)-1,3-thiazole-4-carboxylate (I-813)

Oxalyl chloride (6.78 g) and a drop of N,N-dimethylformamide are added to a solution of [3,5-bis(difluoromethyl)-1H-pyrazol-1-yl]acetic acid (10.8 g) in dichloromethane (150 ml). The reaction mixture is stirred at room temperature overnight, and excess oxalyl chloride is then removed under reduced pressure. The residue is redissolved in dichloromethane (50 ml) and added to a solution of 4-{4-[(1-naphthyloxy)carbonyl]-1,3-thiazol-2-yl}piperidinium chloride (X-2, 7.25 g) and Hünig base (10.4 g) in dichloromethane (100 ml) at 0° C. The reaction mixture is stirred at room temperature overnight. After addition of conc. ammonium chloride solution, the aqueous phase is separated off and extracted with ethyl acetate. The combined organic phases are dried over sodium sulfate. The solid is filtered off and the solvent is removed by distillation. The residue is purified chromatographically. This gives 1-naphthyl 2-(1-{[3,5-bis(difluoromethyl)-1H-pyrazol-1-yl]acetyl}piperidin-4-yl)-1,3-thiazole-4-carboxylate (11.3 g, 64%).

log P (pH 2.7): 3.64

$^1$H NMR (DMSO-d$_6$, 400 MHz): δ$_{ppm}$: 1.70 (bs, 1H), 1.87 (bs, 1H), 2.18 (m, 2H), 2.91 (bs, 1H), 3.31 (bs, 1H), 3.48 (m, 1H), 4.03 (bs, 1H), 4.36 (bs, 1H), 5.36 (s, 2H), 6.85 (s, 1H), 6.97 (t, 1H), 7.15 (t, 1H), 7.45 (dd, 1H), 7.54-7.61 (m, 3H), 7.89 (m, 2H), 8.01 (m, 1H), 8.84 (s, 1H)

MS (ESI): 547 ([M+H]$^+$)

Cyclohexyl 2-(1-{2-[3,5-bis(difluoromethyl)-1H-pyrazol-1-yl]ethanethioyl}piperidin-4-yl)-1,3-thiazole-4-carboxylate (I-854)

At room temperature, 2,4-bis(4-methoxyphenyl)-1,3,2,4-dithiadiphosphetane 2,4-disulfide (88 mg) is added to a solution of cyclohexyl 2-(1-{[3,5-bis(difluoromethyl)-1H-pyrazol-1-yl]acetyl}piperidin-4-yl)-1,3-thiazole-4-carboxylate (I-811, 200 mg) in 1,2-dimethoxyethane (1 ml) and chloroform (0.4 ml). The reaction mixture is stirred at 70-80° C. overnight. After removal of the solvent under reduced pressure, the residue is purified chromatographically. This gives cyclohexyl 2-(1-{2-[3,5-bis(difluoromethyl)-1H-pyrazol-1-yl]ethanethioyl}piperidin-4-yl)-1,3-thiazole-4-carboxylate (80 mg, 39%).

log P (pH 2.7): 4.23

$^1$H NMR (DMSO-d$_6$, 400 MHz): δ$_{ppm}$: 1.30-1.58 (m, 6H), 1.75-1.92 (m, 4H), 2.10-2.30 (m, 4H), 3.32 (m, 1H), 3.50 (m, 2H), 4.39 (m, 1H), 4.93 (m, 1H), 5.39 (s, 2H), 5.42 (m, 1H), 6.79 (t, 1H), 6.83 (s, 1H), 7.01 (t, 1H), 8.16 (s, 1H)

MS (ESI): 519 ([M+H]$^+$)

EXAMPLES

Table 1 shows the compounds of the formula (I) whose use as fungicides is claimed.

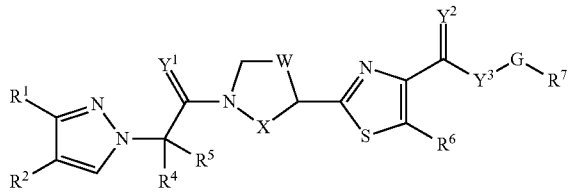

(I)

| EX NO | R$^1$ | R$^2$ | R$^3$ | R$^4$ | R$^5$ | Y$^1$ | X | W | R$^6$ | Y$^2$ | Y$^3$ | G | R$^7$ | log p |
|---|---|---|---|---|---|---|---|---|---|---|---|---|---|---|
| 1 | CF$_3$ | H | CH$_3$ | H | H | O | —CH$_2$CH$_2$— | —CH$_2$— | H | O | O | —CH$_2$— | trimethylsilyl | |
| 2 | CF$_3$ | H | CH$_3$ | H | H | O | —CH$_2$CH$_2$— | —CH$_2$— | H | O | O | bond | cyclohexyl | |
| 3 | CF$_3$ | H | CH$_3$ | H | H | O | —CH$_2$CH$_2$— | —CH$_2$— | H | O | O | bond | cyclopentyl | 3.40* |
| 4 | CF$_3$ | H | CH$_3$ | H | H | O | —CH$_2$CH$_2$— | —CH$_2$— | H | O | O | —CH$_2$— | cyclopropyl | |
| 5 | CF$_3$ | H | CH$_3$ | H | H | O | —CH$_2$CH$_2$— | —CH$_2$— | H | O | O | —CH$_2$— | 2,2-dichlorocyclopropyl | |
| 6 | CF$_3$ | H | CH$_3$ | H | H | O | —CH$_2$CH$_2$— | —CH$_2$— | H | O | O | bond | 1,2,3,4-tetrahydronaphthalen-1-yl | 4.01** |
| 7 | CF$_3$ | H | CH$_3$ | H | H | O | —CH$_2$CH$_2$— | —CH$_2$— | H | O | O | bond | decahydronaphthalen-1-yl | |
| 8 | CF$_3$ | H | CH$_3$ | H | H | O | —CH$_2$CH$_2$— | —CH$_2$— | H | O | O | bond | 2,3-dihydro-1H-inden-1-yl | 3.76* |
| 9 | CF$_3$ | H | CH$_3$ | H | H | O | —CH$_2$CH$_2$— | —CH$_2$— | H | O | O | bond | 1-naphthyl | |
| 10 | CF$_3$ | H | CH$_3$ | H | H | O | —CH$_2$CH$_2$— | —CH$_2$— | H | O | O | bond | 2-naphthyl | 3.84* |
| 11 | CF$_3$ | H | CH$_3$ | H | H | O | —CH$_2$CH$_2$— | —CH$_2$— | H | O | O | —CH$_2$CH$_2$— | morpholin-4-yl | |
| 12 | CF$_3$ | H | CH$_3$ | H | H | O | —CH$_2$CH$_2$— | —CH$_2$— | H | O | O | —CH$_2$— | 4-fluorophenyl | 3.35* |
| 13 | CF$_3$ | H | CH$_3$ | H | H | O | —CH$_2$CH$_2$— | —CH$_2$— | H | O | O | —CH$_2$CH$_2$— | piperidin-1-yl | |
| 14 | CF$_3$ | H | CH$_3$ | H | H | O | —CH$_2$CH$_2$— | —CH$_2$— | H | O | O | —CH$_2$CH$_2$— | pyrrolidin-1-yl | |
| 15 | CF$_3$ | H | CH$_3$ | H | H | O | —CH$_2$CH$_2$— | —CH$_2$— | H | O | O | —CH$_2$— | phenyl | 3.37* |
| 16 | CF$_3$ | H | CH$_3$ | H | H | O | —CH$_2$CH$_2$— | —CH$_2$— | H | O | O | —CH$_2$— | 4-methylpiperazin-1-yl | |
| 17 | CF$_3$ | H | CH$_3$ | H | H | O | —CH$_2$CH$_2$— | —CH$_2$— | H | O | O | —CH$_2$— | 4-chlorophenyl | 3.73* |
| 18 | CF$_3$ | H | CH$_3$ | H | H | O | —CH$_2$CH$_2$— | —CH$_2$— | H | O | O | —CH$_2$— | 4-methylphenyl | 4.21* |
| 19 | CF$_3$ | H | CH$_3$ | H | H | O | —CH$_2$CH$_2$— | —CH$_2$— | H | O | O | —CH$_2$— | 4-methoxyphenyl | 3.30* |

-continued

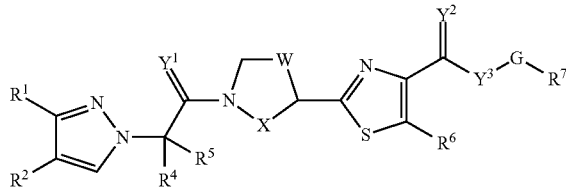

(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 20 | CF₃ | H | CH₃ | H | H | O | —CH₂CH₂— | —CH₂— | H | O | O | —CH₂— | 2,4-dichlorophenyl | 3.69* |
| 21 | CF₃ | H | CH₃ | H | H | O | —CH₂CH₂— | —CH₂— | H | O | O | —CH₂— | 3,5-dichlorophenyl | 4.24* |
| 22 | CF₃ | H | CH₃ | H | H | O | —CH₂CH₂— | —CH₂— | H | O | O | —CH₂— | 2,6-dichlorophenyl | 3.94* |
| 23 | CF₃ | H | CH₃ | H | H | O | —CH₂CH₂— | —CH₂— | H | O | O | —CH₂— | 2-chlorophenyl | 3.70* |
| 24 | CF₃ | H | CH₃ | H | H | O | —CH₂CH₂— | —CH₂— | H | O | O | —CH₂— | 3-chlorophenyl | 3.72* |
| 25 | CF₃ | H | CH₃ | H | H | O | —CH₂CH₂— | —CH₂— | H | O | O | —CH₂— | 3-(trifluoromethyl)phenyl | 3.81* |
| 26 | CF₃ | H | CH₃ | H | H | O | —CH₂CH₂— | —CH₂— | H | O | O | —CH₂— | 3-methylphenyl | |
| 27 | CF₃ | H | CH₃ | H | H | O | —CH₂CH₂— | —CH₂— | H | O | S | —CH₂— | 4-fluorophenyl | 4.00* |
| 28 | CF₃ | H | CH₃ | H | H | O | —CH₂CH₂— | —CH₂— | H | O | O | —CH₂— | 4-nitrophenyl | 3.22* |
| 29 | CF₃ | H | CH₃ | H | H | O | —CH₂CH₂— | —CH₂— | H | O | O | —CH₂— | 4-tert-butylphenyl | 4.57* |
| 30 | CF₃ | H | CH₃ | H | H | O | —CH₂CH₂— | —CH₂— | H | O | S | —CH₂— | phenyl | |
| 31 | CF₃ | H | CH₃ | H | H | O | —CH₂CH₂— | —CH₂— | H | O | O | —CH₂— | 2-methylphenyl | 3.62* |
| 32 | CF₃ | H | CH₃ | H | H | O | —CH₂CH₂— | —CH₂— | H | O | S | —CH₂— | 4-chlorophenyl | |
| 33 | CF₃ | H | CH₃ | H | H | O | —CH₂CH₂— | —CH₂— | H | O | S | —CH₂— | 4-methylphenyl | |
| 34 | CF₃ | H | CH₃ | H | H | O | —CH₂CH₂— | —CH₂— | H | O | S | —CH₂— | 4-methoxyphenyl | |
| 35 | CF₃ | H | CH₃ | H | H | O | —CH₂CH₂— | —CH₂— | H | O | S | —CH₂— | 2,4-dichlorophenyl | |
| 36 | CF₃ | H | CH₃ | H | H | O | —CH₂CH₂— | —CH₂— | H | O | S | —CH₂— | 3,5-dichlorophenyl | |
| 37 | CF₃ | H | CH₃ | H | H | O | —CH₂CH₂— | —CH₂— | H | O | S | —CH₂— | 2,6-dichlorophenyl | |
| 38 | CF₃ | H | CH₃ | H | H | O | —CH₂CH₂— | —CH₂— | H | O | S | —CH₂— | 2-chlorophenyl | |
| 39 | CF₃ | H | CH₃ | H | H | O | —CH₂CH₂— | —CH₂— | H | O | S | —CH₂— | 3-chlorophenyl | |
| 40 | CF₃ | H | CH₃ | H | H | O | —CH₂CH₂— | —CH₂— | H | O | S | —CH₂— | 3-(trifluoromethyl)phenyl | |
| 41 | CF₃ | H | CH₃ | H | H | O | —CH₂CH₂— | —CH₂— | H | O | O | —CH(CH₃)— | 4-fluorophenyl | 3.60* |
| 42 | CF₃ | H | CH₃ | H | H | O | —CH₂CH₂— | —CH₂— | H | O | O | —CH(CH₂CH₃)— | 4-fluorophenyl | 3.89* |
| 43 | CF₃ | H | CH₃ | H | H | O | —CH₂CH₂— | —CH₂— | H | O | O | —CH₂CH₂— | 4-fluorophenyl | 3.55* |
| 44 | CF₃ | H | CH₃ | H | H | O | —CH₂CH₂— | —CH₂— | H | O | O | bond | phenyl | 3.20* |
| 45 | CF₃ | H | CH₃ | H | H | O | —CH₂CH₂— | —CH₂— | H | O | O | bond | 4-fluorophenyl | 3.26* |
| 46 | CF₃ | H | CH₃ | H | H | O | —CH₂CH₂— | —CH₂— | H | O | S | —CH₂— | 2-methylphenyl | |
| 47 | CF₃ | H | CH₃ | H | H | O | —CH₂CH₂— | —CH₂— | H | O | O | —CH(CF₃)— | phenyl | |
| 48 | CF₃ | H | CH₃ | H | H | O | —CH₂CH₂— | —CH₂— | H | O | S | —CH₂— | 4-nitrophenyl | |
| 49 | CF₃ | H | CH₃ | H | H | O | —CH₂CH₂— | —CH₂— | H | O | S | —CH₂— | 4-tert-butylphenyl | |
| 50 | CF₃ | H | CH₃ | H | H | O | —CH₂CH₂— | —CH₂— | H | O | S | —CH₂— | 3-methylphenyl | |
| 51 | CF₃ | H | CH₃ | H | H | O | —CH₂CH₂— | —CH₂— | H | O | O | bond | 3-chlorophenyl | |
| 52 | CF₃ | H | CH₃ | H | H | O | —CH₂CH₂— | —CH₂— | H | O | O | bond | 4-methylphenyl | |
| 53 | CF₃ | H | CH₃ | H | H | O | —CH₂CH₂— | —CH₂— | H | O | O | bond | 3-chlorophenyl | |
| 54 | CF₃ | H | CH₃ | H | H | O | —CH₂CH₂— | —CH₂— | H | O | O | bond | 3,5-dichlorophenyl | |
| 55 | CF₃ | H | CH₃ | H | H | O | —CH₂CH₂— | —CH₂— | H | O | O | bond | 3,4-dichlorophenyl | |
| 56 | CF₃ | H | CH₃ | H | H | O | —CH₂CH₂— | —CH₂— | H | O | O | bond | 2,4-dichlorophenyl | |
| 57 | CF₃ | H | CH₃ | H | H | O | —CH₂CH₂— | —CH₂— | H | O | O | bond | 2-chlorophenyl | |
| 58 | CF₃ | H | CH₃ | H | H | O | —CH₂CH₂— | —CH₂— | H | O | O | bond | 2,6-dichlorophenyl | |
| 59 | CF₃ | H | CH₃ | H | H | O | —CH₂CH₂— | —CH₂— | H | O | O | bond | 3-(trifluoromethyl)phenyl | |
| 60 | CF₃ | H | CH₃ | H | H | O | —CH₂CH₂— | —CH₂— | H | O | O | bond | 3-methylphenyl | |
| 61 | CF₃ | H | CH₃ | H | H | O | —CH₂CH₂— | —CH₂— | H | O | O | bond | 2-methylphenyl | |
| 62 | CF₃ | H | CH₃ | H | H | O | —CH₂CH₂— | —CH₂— | H | O | O | bond | 4-tert-butylphenyl | |
| 63 | CF₃ | H | CH₃ | H | H | O | —CH₂CH₂— | —CH₂— | H | O | O | bond | 4-nitrophenyl | |
| 64 | CF₃ | H | CH₃ | H | H | O | —CH₂CH₂— | —CH₂— | H | O | S | bond | phenyl | |
| 65 | CF₃ | H | CH₃ | H | H | O | —CH₂CH₂— | —CH₂— | H | O | S | bond | 4-fluorophenyl | |
| 66 | CF₃ | H | CH₃ | H | H | O | —CH₂CH₂— | —CH₂— | H | O | S | bond | 4-chlorophenyl | |
| 67 | CF₃ | H | CH₃ | H | H | O | —CH₂CH₂— | —CH₂— | H | O | S | bond | 4-methylphenyl | |
| 68 | CF₃ | H | CH₃ | H | H | O | —CH₂CH₂— | —CH₂— | H | O | S | bond | 3-chlorophenyl | |

-continued

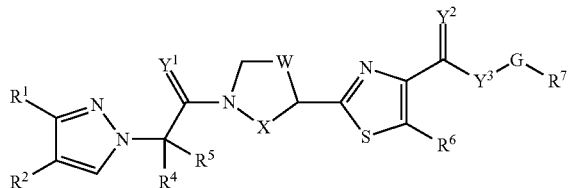
(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 69 | CF₃ | H | CH₃ | H | H | O | —CH₂CH₂— | —CH₂— | H | O | S | bond | 3,5-dichlorophenyl | |
| 70 | CF₃ | H | CH₃ | H | H | O | —CH₂CH₂— | —CH₂— | H | O | S | bond | 3,4-dichlorophenyl | |
| 71 | CF₃ | H | CH₃ | H | H | O | —CH₂CH₂— | —CH₂— | H | O | S | bond | 2,4-dichlorophenyl | |
| 72 | CF₃ | H | CH₃ | H | H | O | —CH₂CH₂— | —CH₂— | H | O | S | bond | 2-chlorophenyl | |
| 73 | CF₃ | H | CH₃ | H | H | O | —CH₂CH₂— | —CH₂— | H | O | S | bond | 2,6-dichlorophenyl | |
| 74 | CF₃ | H | CH₃ | H | H | O | —CH₂CH₂— | —CH₂— | H | O | S | bond | 3-(trifluoromethyl)phenyl | |
| 75 | CF₃ | H | CH₃ | H | H | O | —CH₂CH₂— | —CH₂— | H | O | S | bond | 3-methylphenyl | |
| 76 | CF₃ | H | CH₃ | H | H | O | —CH₂CH₂— | —CH₂— | H | O | S | bond | cyclohexyl | 4.51* |
| 77 | CF₃ | H | CH₃ | H | H | O | —CH₂CH₂— | —CH₂— | H | O | S | bond | 1-naphthyl | 4.22* |
| 78 | CF₃ | H | CH₃ | H | H | O | —CH₂CH₂— | —CH₂— | H | O | S | bond | 4-nitrophenyl | |
| 79 | CF₃ | H | CH₃ | H | H | O | —CH₂CH₂— | —CH₂— | H | O | O | —CH₂— | pyridin-4-yl | |
| 80 | CF₃ | H | CH₃ | H | H | O | —CH₂CH₂— | —CH₂— | H | O | O | —CH₂— | pyridin-2-yl | 2.21* |
| 81 | CF₃ | H | CH₃ | H | H | O | —CH₂CH₂— | —CH₂— | H | O | O | —CH₂— | 2-thienyl | 3.22* |
| 82 | CF₃ | H | CH₃ | H | H | O | —CH₂CH₂— | —CH₂— | H | O | S | bond | 2-methylphenyl | |
| 83 | CF₃ | H | CH₃ | H | H | O | —CH₂CH₂— | —CH₂— | H | O | S | bond | 4-tert-butylphenyl | |
| 84 | CF₃ | H | H | H | H | O | —CH₂CH₂— | —CH₂— | H | O | O | —CH₂— | trimethylsilyl | 3.53* |
| 85 | CF₃ | H | H | H | H | O | —CH₂CH₂— | —CH₂— | H | O | O | bond | cyclohexyl | 3.42* |
| 86 | CF₃ | H | H | H | H | O | —CH₂CH₂— | —CH₂— | H | O | O | bond | cyclopentyl | |
| 87 | CF₃ | H | H | H | H | O | —CH₂CH₂— | —CH₂— | H | O | O | —CH₂— | cyclopropyl | |
| 88 | CF₃ | H | H | H | H | O | —CH₂CH₂— | —CH₂— | H | O | O | —CH₂— | 2,2-dichlorocyclopropyl | |
| 89 | CF₃ | H | H | H | H | O | —CH₂CH₂— | —CH₂— | H | O | O | bond | 1,2,3,4-tetrahydronaphthalen-1-yl | 3.68* |
| 90 | CF₃ | H | H | H | H | O | —CH₂CH₂— | —CH₂— | H | O | O | bond | decahydronaphthalen-1-yl | |
| 91 | CF₃ | H | H | H | H | O | —CH₂CH₂— | —CH₂— | H | O | O | bond | 2,3-dihydro-1H-inden-1-yl | 3.37* |
| 92 | CF₃ | H | H | H | H | O | —CH₂CH₂— | —CH₂— | H | O | O | bond | 1-naphthyl | 3.42* |
| 93 | CF₃ | H | H | H | H | O | —CH₂CH₂— | —CH₂— | H | O | O | bond | 2-naphthyl | |
| 94 | CF₃ | H | H | H | H | O | —CH₂CH₂— | —CH₂— | H | O | O | —CH₂— | phenyl | 2.99* |
| 95 | CF₃ | H | H | H | H | O | —CH₂CH₂— | —CH₂— | H | O | O | —CH₂— | 4-fluorophenyl | 3.04* |
| 96 | CF₃ | H | H | H | H | O | —CH₂CH₂— | —CH₂— | H | O | O | —CH₂— | 4-chlorophenyl | |
| 97 | CF₃ | H | H | H | H | O | —CH₂CH₂— | —CH₂— | H | O | O | —CH₂— | 4-methylphenyl | |
| 98 | CF₃ | H | H | H | H | O | —CH₂CH₂— | —CH₂— | H | O | O | —CH₂— | 4-methoxyphenyl | |
| 99 | CF₃ | H | H | H | H | O | —CH₂CH₂— | —CH₂— | H | O | O | —CH₂— | 2,4-dichlorophenyl | |
| 100 | CF₃ | H | H | H | H | O | —CH₂CH₂— | —CH₂— | H | O | O | —CH₂— | 3,5-dichlorophenyl | |
| 101 | CF₃ | H | H | H | H | O | —CH₂CH₂— | —CH₂— | H | O | O | —CH₂— | 2,6-dichlorophenyl | |
| 102 | CF₃ | H | H | H | H | O | —CH₂CH₂— | —CH₂— | H | O | O | —CH₂— | 2-chlorophenyl | |
| 103 | CF₃ | H | H | H | H | O | —CH₂CH₂— | —CH₂— | H | O | O | —CH₂— | 3-chlorophenyl | |
| 104 | CF₃ | H | H | H | H | O | —CH₂CH₂— | —CH₂— | H | O | O | —CH₂— | 3-(trifluoromethyl)phenyl | |
| 105 | CF₃ | H | H | H | H | O | —CH₂CH₂— | —CH₂— | H | O | O | —CH₂— | 3-methylphenyl | |
| 106 | CF₃ | H | H | H | H | O | —CH₂CH₂— | —CH₂— | H | O | O | —CH₂— | 2-methylphenyl | |
| 107 | CF₃ | H | H | H | H | O | —CH₂CH₂— | —CH₂— | H | O | O | —CH₂— | 4-nitrophenyl | |
| 108 | CF₃ | H | H | H | H | O | —CH₂CH₂— | —CH₂— | H | O | O | —CH₂— | 4-tert-butylphenyl | |
| 109 | CF₃ | H | H | H | H | O | —CH₂CH₂— | —CH₂— | H | O | S | —CH₂— | phenyl | |
| 110 | CF₃ | H | H | H | H | O | —CH₂CH₂— | —CH₂— | H | O | S | —CH₂— | 4-fluorophenyl | |
| 111 | CF₃ | H | H | H | H | O | —CH₂CH₂— | —CH₂— | H | O | S | —CH₂— | 4-chlorophenyl | |
| 112 | CF₃ | H | H | H | H | O | —CH₂CH₂— | —CH₂— | H | O | S | —CH₂— | 4-methylphenyl | |
| 113 | CF₃ | H | H | H | H | O | —CH₂CH₂— | —CH₂— | H | O | S | —CH₂— | 4-methoxyphenyl | |
| 114 | CF₃ | H | H | H | H | O | —CH₂CH₂— | —CH₂— | H | O | S | —CH₂— | 2,4-dichlorophenyl | |

-continued

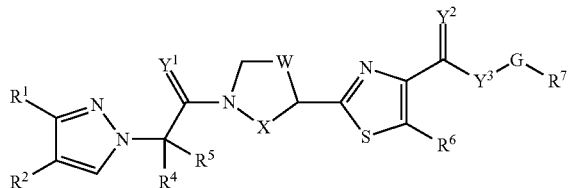

(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 115 | CF₃ | H | H | H | H | O | —CH₂CH₂— | —CH₂— | H | O | S | —CH₂— | 3,5-dichlorophenyl | |
| 116 | CF₃ | H | H | H | H | O | —CH₂CH₂— | —CH₂— | H | O | S | —CH₂— | 2,6-dichlorophenyl | |
| 117 | CF₃ | H | H | H | H | O | —CH₂CH₂— | —CH₂— | H | O | S | —CH₂— | 2-chlorophenyl | |
| 118 | CF₃ | H | H | H | H | O | —CH₂CH₂— | —CH₂— | H | O | S | —CH₂— | 3-chlorophenyl | |
| 119 | CF₃ | H | H | H | H | O | —CH₂CH₂— | —CH₂— | H | O | S | —CH₂— | 3-(trifluoromethyl)phenyl | |
| 120 | CF₃ | H | H | H | H | O | —CH₂CH₂— | —CH₂— | H | O | S | —CH₂— | 3-methylphenyl | |
| 121 | CF₃ | H | H | H | H | O | —CH₂CH₂— | —CH₂— | H | O | S | —CH₂— | 2-methylphenyl | |
| 122 | CF₃ | H | H | H | H | O | —CH₂CH₂— | —CH₂— | H | O | S | —CH₂— | 4-nitrophenyl | |
| 123 | CF₃ | H | H | H | H | O | —CH₂CH₂— | —CH₂— | H | O | S | —CH₂— | 4-tert-butylphenyl | |
| 124 | CF₃ | H | H | H | H | O | —CH₂CH₂— | —CH₂— | H | O | O | —CH(CH₃)— | 4-fluorophenyl | 3.18* |
| 125 | CF₃ | H | H | H | H | O | —CH₂CH₂— | —CH₂— | H | O | O | —CH(CH₃)— | 4-fluorophenyl | |
| 126 | CF₃ | H | H | H | H | O | —CH₂CH₂— | —CH₂— | H | O | O | —CH₂CH₂— | 4-fluorophenyl | 3.27* |
| 127 | CF₃ | H | H | H | H | O | —CH₂CH₂— | —CH₂— | H | O | O | bond | phenyl | 2.85* |
| 128 | CF₃ | H | H | H | H | O | —CH₂CH₂— | —CH₂— | H | O | O | bond | 4-fluorophenyl | 2.89* |
| 129 | CF₃ | H | H | H | H | O | —CH₂CH₂— | —CH₂— | H | O | O | bond | 4-chlorophenyl | |
| 130 | CF₃ | H | H | H | H | O | —CH₂CH₂— | —CH₂— | H | O | O | bond | 4-methylphenyl | |
| 131 | CF₃ | H | H | H | H | O | —CH₂CH₂— | —CH₂— | H | O | O | bond | 3-chlorophenyl | |
| 132 | CF₃ | H | H | H | H | O | —CH₂CH₂— | —CH₂— | H | O | O | bond | 3,5-dichlorophenyl | |
| 133 | CF₃ | H | H | H | H | O | —CH₂CH₂— | —CH₂— | H | O | O | bond | 3,4-dichlorophenyl | |
| 134 | CF₃ | H | H | H | H | O | —CH₂CH₂— | —CH₂— | H | O | O | bond | 2,4-dichlorophenyl | |
| 135 | CF₃ | H | H | H | H | O | —CH₂CH₂— | —CH₂— | H | O | O | bond | 2-chlorophenyl | |
| 136 | CF₃ | H | H | H | H | O | —CH₂CH₂— | —CH₂— | H | O | O | bond | 2,6-dichlorophenyl | |
| 137 | CF₃ | H | H | H | H | O | —CH₂CH₂— | —CH₂— | H | O | O | bond | 3-(trifluoromethyl)phenyl | |
| 138 | CF₃ | H | H | H | H | O | —CH₂CH₂— | —CH₂— | H | O | O | bond | 3-methylphenyl | |
| 139 | CF₃ | H | H | H | H | O | —CH₂CH₂— | —CH₂— | H | O | O | bond | 2-methylphenyl | |
| 140 | CF₃ | H | H | H | H | O | —CH₂CH₂— | —CH₂— | H | O | O | bond | 4-tert-butylphenyl | |
| 141 | CF₃ | H | H | H | H | O | —CH₂CH₂— | —CH₂— | H | O | O | bond | 4-nitrophenyl | |
| 142 | CF₃ | H | H | H | H | O | —CH₂CH₂— | —CH₂— | H | O | O | —CH₂— | pyridin-4-yl | 1.32* |
| 143 | CF₃ | H | H | H | H | O | —CH₂CH₂— | —CH₂— | H | O | O | —CH₂— | 2-thienyl | 2.85* |
| 144 | CF₃ | chlorine | CH₃ | H | H | O | —CH₂CH₂— | —CH₂— | H | O | O | —CH₂— | trimethylsilyl | 4.28* |
| 145 | CF₃ | chlorine | CH₃ | H | H | O | —CH₂CH₂— | —CH₂— | H | O | O | bond | cyclohexyl | 4.17* |
| 146 | CF₃ | chlorine | CH₃ | H | H | O | —CH₂CH₂— | —CH₂— | H | O | O | bond | cyclopentyl | 3.84* |
| 147 | CF₃ | chlorine | CH₃ | H | H | O | —CH₂CH₂— | —CH₂— | H | O | O | —CH₂— | cyclopropyl | |
| 148 | CF₃ | chlorine | CH₃ | H | H | O | —CH₂CH₂— | —CH₂— | H | O | O | —CH₂— | 2,2-dichloropropyl | |
| 149 | CF₃ | chlorine | CH₃ | H | H | O | —CH₂CH₂— | —CH₂— | H | O | O | bond | 1,2,3,4-tetrahydronaphthalen-1-yl | 4.40* |
| 150 | CF₃ | chlorine | CH₃ | H | H | O | —CH₂CH₂— | —CH₂— | H | O | O | bond | decahydronaphthalen-1-yl | 5.44* |
| 151 | CF₃ | chlorine | CH₃ | H | H | O | —CH₂CH₂— | —CH₂— | H | O | O | bond | 2,3-dihydro-1H-inden-1-yl | 4.17* |
| 152 | CF₃ | chlorine | CH₃ | H | H | O | —CH₂CH₂— | —CH₂— | H | O | O | bond | 1-naphthyl | 4.17* |
| 153 | CF₃ | chlorine | CH₃ | H | H | O | —CH₂CH₂— | —CH₂— | H | O | O | bond | 2-naphthyl | 4.17* |
| 154 | CF₃ | chlorine | CH₃ | H | H | O | —CH₂CH₂— | —CH₂— | H | O | O | —CH₂— | phenyl | 3.73* |
| 155 | CF₃ | chlorine | CH₃ | H | H | O | —CH₂CH₂— | —CH₂— | H | O | O | —CH₂— | 4-fluorophenyl | 3.73* |
| 156 | CF₃ | chlorine | CH₃ | H | H | O | —CH₂CH₂— | —CH₂— | H | O | O | —CH₂— | 4-chlorophenyl | |

-continued

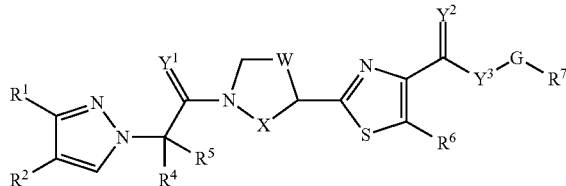

(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 157 | CF₃ | chlorine | CH₃ | H | H | O | —CH₂CH₂— | —CH₂— | H | O | O | —CH₂— | 4-methylphenyl | |
| 158 | CF₃ | chlorine | CH₃ | H | H | O | —CH₂CH₂— | —CH₂— | H | O | O | —CH₂— | 4-methoxyphenyl | |
| 159 | CF₃ | chlorine | CH₃ | H | H | O | —CH₂CH₂— | —CH₂— | H | O | O | —CH₂— | 2,3-dichlorophenyl | |
| 160 | CF₃ | chlorine | CH₃ | H | H | O | —CH₂CH₂— | —CH₂— | H | O | O | —CH₂— | 2,5-dichlorophenyl | |
| 161 | CF₃ | chlorine | CH₃ | H | H | O | —CH₂CH₂— | —CH₂— | H | O | O | —CH₂— | 2,6-dichlorophenyl | |
| 162 | CF₃ | chlorine | CH₃ | H | H | O | —CH₂CH₂— | —CH₂— | H | O | O | —CH₂— | 2-chlorophenyl | |
| 163 | CF₃ | chlorine | CH₃ | H | H | O | —CH₂CH₂— | —CH₂— | H | O | O | —CH₂— | 3-chlorophenyl | |
| 164 | CF₃ | chlorine | CH₃ | H | H | O | —CH₂CH₂— | —CH₂— | H | O | O | —CH₂— | 3-(trifluoromethyl)phenyl | |
| 165 | CF₃ | chlorine | CH₃ | H | H | O | —CH₂CH₂— | —CH₂— | H | O | O | —CH₂— | 3-methylphenyl | |
| 166 | CF₃ | chlorine | CH₃ | H | H | O | —CH₂CH₂— | —CH₂— | H | O | O | —CH₂— | 2-methylphenyl | |
| 167 | CF₃ | chlorine | CH₃ | H | H | O | —CH₂CH₂— | —CH₂— | H | O | O | —CH₂— | 4-nitrophenyl | |
| 168 | CF₃ | chlorine | CH₃ | H | H | O | —CH₂CH₂— | —CH₂— | H | O | O | —CH₂— | 4-tert-butylphenyl | |
| 169 | CF₃ | chlorine | CH₃ | H | H | O | —CH₂CH₂— | —CH₂— | H | O | S | —CH₂— | phenyl | |
| 170 | CF₃ | chlorine | CH₃ | H | H | O | —CH₂CH₂— | —CH₂— | H | O | S | —CH₂— | 4-fluorophenyl | |
| 171 | CF₃ | chlorine | CH₃ | H | H | O | —CH₂CH₂— | —CH₂— | H | O | S | —CH₂— | 4-chlorophenyl | |
| 172 | CF₃ | chlorine | CH₃ | H | H | O | —CH₂CH₂— | —CH₂— | H | O | S | —CH₂— | 4-methylphenyl | |
| 173 | CF₃ | chlorine | CH₃ | H | H | O | —CH₂CH₂— | —CH₂— | H | O | S | —CH₂— | 4-methoxyphenyl | |
| 174 | CF₃ | chlorine | CH₃ | H | H | O | —CH₂CH₂— | —CH₂— | H | O | S | —CH₂— | 2,4-dichlorophenyl | |
| 175 | CF₃ | chlorine | CH₃ | H | H | O | —CH₂CH₂— | —CH₂— | H | O | S | —CH₂— | 3,5-dichlorophenyl | |
| 176 | CF₃ | chlorine | CH₃ | H | H | O | —CH₂CH₂— | —CH₂— | H | O | S | —CH₂— | 2,6-dichlorophenyl | |
| 177 | CF₃ | chlorine | CH₃ | H | H | O | —CH₂CH₂— | —CH₂— | H | O | S | —CH₂— | 2-chlorophenyl | |
| 178 | CF₃ | chlorine | CH₃ | H | H | O | —CH₂CH₂— | —CH₂— | H | O | S | —CH₂— | 3-chlorophenyl | |
| 179 | CF₃ | chlorine | CH₃ | H | H | O | —CH₂CH₂— | —CH₂— | H | O | S | —CH₂— | 3-(trifluoromethyl)phenyl | |
| 180 | CF₃ | chlorine | CH₃ | H | H | O | —CH₂CH₂— | —CH₂— | H | O | S | —CH₂— | 3-methylphenyl | |
| 181 | CF₃ | chlorine | CH₃ | H | H | O | —CH₂CH₂— | —CH₂— | H | O | S | —CH₂— | 2-methylphenyl | |
| 182 | CF₃ | chlorine | CH₃ | H | H | O | —CH₂CH₂— | —CH₂— | H | O | S | —CH₂— | 4-nitrophenyl | |
| 183 | CF₃ | chlorine | CH₃ | H | H | O | —CH₂CH₂— | —CH₂— | H | O | S | —CH₂— | 4-tert-butylphenyl | |
| 184 | CF₃ | chlorine | CH₃ | H | H | O | —CH₂CH₂— | —CH₂— | H | O | O | —CH(CH₃)— | 4-fluorophenyl | 3.89* |
| 185 | CF₃ | chlorine | CH₃ | H | H | O | —CH₂CH₂— | —CH₂— | H | O | O | —CH(CH₂CH₃)— | 4-fluorophenyl | |
| 186 | CF₃ | chlorine | CH₃ | H | H | O | —CH₂CH₂— | —CH₂— | H | O | O | —CH₂CH₂— | 4-fluorophenyl | 3.94* |
| 187 | CF₃ | chlorine | CH₃ | H | H | O | —CH₂CH₂— | —CH₂— | H | O | O | bond | phenyl | 3.58* |
| 188 | CF₃ | chlorine | CH₃ | H | H | O | —CH₂CH₂— | —CH₂— | H | O | O | bond | 4-fluorophenyl | 3.63* |
| 189 | CF₃ | chlorine | CH₃ | H | H | O | —CH₂CH₂— | —CH₂— | H | O | O | bond | 4-chlorophenyl | |

-continued

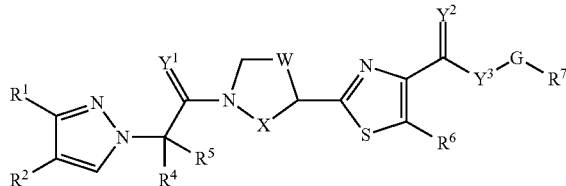

(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 190 | CF₃ | chlorine | CH₃ | H | H | O | —CH₂CH₂— | —CH₂— | H | O | O | bond | 4-methylphenyl | |
| 191 | CF₃ | chlorine | CH₃ | H | H | O | —CH₂CH₂— | —CH₂— | H | O | O | bond | 3-chlorophenyl | |
| 192 | CF₃ | chlorine | CH₃ | H | H | O | —CH₂CH₂— | —CH₂— | H | O | O | bond | 3,5-dichlorophenyl | |
| 193 | CF₃ | chlorine | CH₃ | H | H | O | —CH₂CH₂— | —CH₂— | H | O | O | bond | 3,4-dichlorophenyl | |
| 194 | CF₃ | chlorine | CH₃ | H | H | O | —CH₂CH₂— | —CH₂— | H | O | O | bond | 2,4-dichlorophenyl | |
| 195 | CF₃ | chlorine | CH₃ | H | H | O | —CH₂CH₂— | —CH₂— | H | O | O | bond | 2-chlorophenyl | |
| 196 | CF₃ | chlorine | CH₃ | H | H | O | —CH₂CH₂— | —CH₂— | H | O | O | bond | 2,6-dichlorophenyl | |
| 197 | CF₃ | chlorine | CH₃ | H | H | O | —CH₂CH₂— | —CH₂— | H | O | O | bond | 3-(trifluoromethyl)phenyl | |
| 198 | CF₃ | chlorine | CH₃ | H | H | O | —CH₂CH₂— | —CH₂— | H | O | O | bond | 3-methylphenyl | |
| 199 | CF₃ | chlorine | CH₃ | H | H | O | —CH₂CH₂— | —CH₂— | H | O | O | bond | 2-methylphenyl | |
| 200 | CF₃ | chlorine | CH₃ | H | H | O | —CH₂CH₂— | —CH₂— | H | O | O | bond | 4-tert-butylphenyl | |
| 201 | CF₃ | chlorine | CH₃ | H | H | O | —CH₂CH₂— | —CH₂— | H | O | O | bond | 4-nitrophenyl | |
| 202 | CF₃ | chlorine | CH₃ | H | H | O | —CH₂CH₂— | —CH₂— | H | O | S | bond | phenyl | |
| 203 | CF₃ | chlorine | CH₃ | H | H | O | —CH₂CH₂— | —CH₂— | H | O | S | bond | 4-fluorophenyl | |
| 204 | CF₃ | chlorine | CH₃ | H | H | O | —CH₂CH₂— | —CH₂— | H | O | S | bond | 4-chlorophenyl | |
| 205 | CF₃ | chlorine | CH₃ | H | H | O | —CH₂CH₂— | —CH₂— | H | O | S | bond | 4-methylphenyl | |
| 206 | CF₃ | chlorine | CH₃ | H | H | O | —CH₂CH₂— | —CH₂— | H | O | S | bond | 3-chlorophenyl | |
| 207 | CF₃ | chlorine | CH₃ | H | H | O | —CH₂CH₂— | —CH₂— | H | O | S | bond | 3,5-dichlorophenyl | |
| 208 | CF₃ | chlorine | CH₃ | H | H | O | —CH₂CH₂— | —CH₂— | H | O | S | bond | 3,4-dichlorophenyl | |
| 209 | CF₃ | chlorine | CH₃ | H | H | O | —CH₂CH₂— | —CH₂— | H | O | S | bond | 2,4-dichlorophenyl | |
| 210 | CF₃ | chlorine | CH₃ | H | H | O | —CH₂CH₂— | —CH₂— | H | O | S | bond | 2-chlorophenyl | |
| 211 | CF₃ | chlorine | CH₃ | H | H | O | —CH₂CH₂— | —CH₂— | H | O | S | bond | 2,6-dichlorophenyl | |
| 212 | CF₃ | chlorine | CH₃ | H | H | O | —CH₂CH₂— | —CH₂— | H | O | S | bond | 3-(trifluoromethyl)phenyl | |
| 213 | CF₃ | chlorine | CH₃ | H | H | O | —CH₂CH₂— | —CH₂— | H | O | S | bond | 3-methylphenyl | |
| 214 | CF₃ | chlorine | CH₃ | H | H | O | —CH₂CH₂— | —CH₂— | H | O | S | bond | 2-methylphenyl | |
| 215 | CF₃ | chlorine | CH₃ | H | H | O | —CH₂CH₂— | —CH₂— | H | O | S | bond | 4-tert-butylphenyl | |
| 216 | CF₃ | chlorine | CH₃ | H | H | O | —CH₂CH₂— | —CH₂— | H | O | S | bond | 4-nitrophenyl | |
| 217 | CF₃ | chlorine | CH₃ | H | H | O | —CH₂CH₂— | —CH₂— | H | O | O | —CH₂— | pyridin-4-yl | 1.82* |
| 218 | CF₃ | chlorine | CH₃ | H | H | O | —CH₂CH₂— | —CH₂— | H | O | O | —CH₂— | 2-thienyl | 3.58* |
| 219 | CF₃ | H | CH₃ | H | H | O | —CH₂— | —CH₂CH₂— | H | O | O | —CH₂— | trimethylsilyl | 3.89* |
| 220 | CF₃ | H | CH₃ | H | H | O | —CH₂— | —CH₂CH₂— | H | O | O | bond | cyclohexyl | 3.74* |
| 221 | CF₃ | H | CH₃ | H | H | O | —CH₂— | —CH₂CH₂— | H | O | O | bond | cyclopentyl | 3.47* |
| 222 | CF₃ | H | CH₃ | H | H | O | —CH₂— | —CH₂CH₂— | H | O | O | —CH₂— | cyclopropyl | |
| 223 | CF₃ | H | CH₃ | H | H | O | —CH₂— | —CH₂CH₂— | H | O | O | —CH₂— | 2,2-dichlorocyclopropyl | |

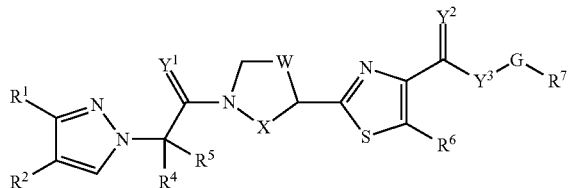

(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 224 | CF₃ | H | CH₃ | H | H | O | —CH₂— | —CH₂CH₂— | H | O | O | bond | 1,2,3,4-tetrahydro-naphthalen-1-yl | 4.01* |
| 225 | CF₃ | H | CH₃ | H | H | O | —CH₂— | —CH₂CH₂— | H | O | O | bond | decahydro-naphthalen-1-yl | 5.08* |
| 226 | CF₃ | H | CH₃ | H | H | O | —CH₂— | —CH₂CH₂— | H | O | O | bond | 2,3-dihydro-1H-inden-1-yl | 3.78* |
| 227 | CF₃ | H | CH₃ | H | H | O | —CH₂— | —CH₂CH₂— | H | O | O | bond | 1-naphthyl | 3.75* |
| 228 | CF₃ | H | CH₃ | H | H | O | —CH₂— | —CH₂CH₂— | H | O | O | bond | 2-naphthyl | 3.84* |
| 229 | CF₃ | H | CH₃ | H | H | O | —CH₂— | —CH₂CH₂— | H | O | O | —CH₂— | phenyl | 3.37* |
| 230 | CF₃ | H | CH₃ | H | H | O | —CH₂— | —CH₂CH₂— | H | O | O | —CH₂— | 4-fluorophenyl | 3.37* |
| 231 | CF₃ | H | CH₃ | H | H | O | —CH₂— | —CH₂CH₂— | H | O | O | —CH₂— | 4-chlorophenyl | |
| 232 | CF₃ | H | CH₃ | H | H | O | —CH₂— | —CH₂CH₂— | H | O | O | —CH₂— | 4-methylphenyl | |
| 233 | CF₃ | H | CH₃ | H | H | O | —CH₂— | —CH₂CH₂— | H | O | O | —CH₂— | 4-methoxy-phenyl | |
| 234 | CF₃ | H | CH₃ | H | H | O | —CH₂— | —CH₂CH₂— | H | O | O | —CH₂— | 2,4-dichloro-phenyl | |
| 235 | CF₃ | H | CH₃ | H | H | O | —CH₂— | —CH₂CH₂— | H | O | O | —CH₂— | 3,5-dichloro-phenyl | |
| 236 | CF₃ | H | CH₃ | H | H | O | —CH₂— | —CH₂CH₂— | H | O | O | —CH₂— | 2,6-dichloro-phenyl | |
| 237 | CF₃ | H | CH₃ | H | H | O | —CH₂— | —CH₂CH₂— | H | O | O | —CH₂— | 2-chlorophenyl | |
| 238 | CF₃ | H | CH₃ | H | H | O | —CH₂— | —CH₂CH₂— | H | O | O | —CH₂— | 3-chlorophenyl | |
| 239 | CF₃ | H | CH₃ | H | H | O | —CH₂— | —CH₂CH₂— | H | O | O | —CH₂— | 3-(trifluoromethyl)phenyl | |
| 240 | CF₃ | H | CH₃ | H | H | O | —CH₂— | —CH₂CH₂— | H | O | O | —CH₂— | 3-methylphenyl | |
| 241 | CF₃ | H | CH₃ | H | H | O | —CH₂— | —CH₂CH₂— | H | O | O | —CH₂— | 2-methylphenyl | |
| 242 | CF₃ | H | CH₃ | H | H | O | —CH₂— | —CH₂CH₂— | H | O | O | —CH₂— | 4-nitrophenyl | |
| 243 | CF₃ | H | CH₃ | H | H | O | —CH₂— | —CH₂CH₂— | H | O | O | —CH₂— | 4-tert-butyl-phenyl | |
| 244 | CF₃ | H | CH₃ | H | H | O | —CH₂— | —CH₂CH₂— | H | O | S | —CH₂— | phenyl | |
| 245 | CF₃ | H | CH₃ | H | H | O | —CH₂— | —CH₂CH₂— | H | O | S | —CH₂— | 4-fluorophenyl | |
| 246 | CF₃ | H | CH₃ | H | H | O | —CH₂— | —CH₂CH₂— | H | O | S | —CH₂— | 4-chlorophenyl | |
| 247 | CF₃ | H | CH₃ | H | H | O | —CH₂— | —CH₂CH₂— | H | O | S | —CH₂— | 4-methylphenyl | |
| 248 | CF₃ | H | CH₃ | H | H | O | —CH₂— | —CH₂CH₂— | H | O | S | —CH₂— | 4-methoxy-phenyl | |
| 249 | CF₃ | H | CH₃ | H | H | O | —CH₂— | —CH₂CH₂— | H | O | S | —CH₂— | 2,4-dichloro-phenyl | |
| 250 | CF₃ | H | CH₃ | H | H | O | —CH₂— | —CH₂CH₂— | H | O | S | —CH₂— | 3,5-dichloro-phenyl | |
| 251 | CF₃ | H | CH₃ | H | H | O | —CH₂— | —CH₂CH₂— | H | O | S | —CH₂— | 2,6-dichloro-phenyl | |
| 252 | CF₃ | H | CH₃ | H | H | O | —CH₂— | —CH₂CH₂— | H | O | S | —CH₂— | 2-chlorophenyl | |
| 253 | CF₃ | H | CH₃ | H | H | O | —CH₂— | —CH₂CH₂— | H | O | S | —CH₂— | 3-chlorophenyl | |
| 254 | CF₃ | H | CH₃ | H | H | O | —CH₂— | —CH₂CH₂— | H | O | S | —CH₂— | 3-(trifluoromethyl)phenyl | |
| 255 | CF₃ | H | CH₃ | H | H | O | —CH₂— | —CH₂CH₂— | H | O | S | —CH₂— | 3-methylphenyl | |
| 256 | CF₃ | H | CH₃ | H | H | O | —CH₂— | —CH₂CH₂— | H | O | S | —CH₂— | 2-methylphenyl | |
| 257 | CF₃ | H | CH₃ | H | H | O | —CH₂— | —CH₂CH₂— | H | O | S | —CH₂— | 4-nitrophenyl | |
| 258 | CF₃ | H | CH₃ | H | H | O | —CH₂— | —CH₂CH₂— | H | O | S | —CH₂— | 4-tert-butyl-phenyl | |
| 259 | CF₃ | H | CH₃ | H | H | O | —CH₂— | —CH₂CH₂— | H | O | O | —CH(CH₃)— | 4-fluorophenyl | 3.53* |
| 260 | CF₃ | H | CH₃ | H | H | O | —CH₂— | —CH₂CH₂— | H | O | O | —CH(CH₂CH₃)— | 4-fluorophenyl | |
| 261 | CF₃ | H | CH₃ | H | H | O | —CH₂— | —CH₂CH₂— | H | O | O | —CH₂CH₃— | 4-fluorophenyl | 3.63* |
| 262 | CF₃ | H | CH₃ | H | H | O | —CH₂— | —CH₂CH₂— | H | O | O | bond | phenyl | 3.18* |
| 263 | CF₃ | H | CH₃ | H | H | O | —CH₂— | —CH₂CH₂— | H | O | O | bond | 4-fluorophenyl | 3.27* |
| 264 | CF₃ | H | CH₃ | H | H | O | —CH₂— | —CH₂CH₂— | H | O | O | bond | 4-chlorophenyl | |
| 265 | CF₃ | H | CH₃ | H | H | O | —CH₂— | —CH₂CH₂— | H | O | O | bond | 4-methylphenyl | |
| 266 | CF₃ | H | CH₃ | H | H | O | —CH₂— | —CH₂CH₂— | H | O | O | bond | 3-chlorophenyl-phenyl | |
| 267 | CF₃ | H | CH₃ | H | H | O | —CH₂— | —CH₂CH₂— | H | O | O | bond | 3,5-dichloro | |
| 268 | CF₃ | H | CH₃ | H | H | O | —CH₂— | —CH₂CH₂— | H | O | O | bond | 3,4-dichloro-phenyl | |
| 269 | CF₃ | H | CH₃ | H | H | O | —CH₂— | —CH₂CH₂— | H | O | O | bond | 2,4-dichloro phenyl | |

-continued

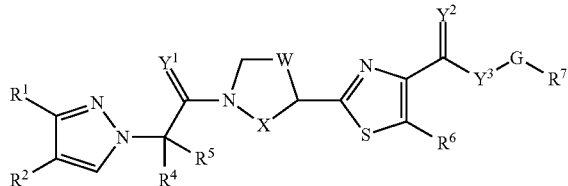

(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 270 | CF₃ | H | CH₃ | H | H | O | —CH₂— | —CH₂CH₂— | H | O | O | bond | 2-chlorophenyl | |
| 271 | CF₃ | H | CH₃ | H | H | O | —CH₂— | —CH₂CH₂— | H | O | O | bond | 2,6-dichlorophenyl | |
| 272 | CF₃ | H | CH₃ | H | H | O | —CH₂— | —CH₂CH₂— | H | O | O | bond | 3-(trifluoromethyl)phenyl | |
| 273 | CF₃ | H | CH₃ | H | H | O | —CH₂— | —CH₂CH₂— | H | O | O | bond | 3-methylphenyl | |
| 274 | CF₃ | H | CH₃ | H | H | O | —CH₂— | —CH₂CH₂— | H | O | O | bond | 2-methylphenyl | |
| 275 | CF₃ | H | CH₃ | H | H | O | —CH₂— | —CH₂CH₂— | H | O | O | bond | 4-tert-butylphenyl | |
| 276 | CF₃ | H | CH₃ | H | H | O | —CH₂— | —CH₂CH₂— | H | O | O | bond | 4-nitrophenyl | |
| 277 | CF₃ | H | CH₃ | H | H | O | —CH₂— | —CH₂CH₂— | H | O | S | bond | phenyl | |
| 278 | CF₃ | H | CH₃ | H | H | O | —CH₂— | —CH₂CH₂— | H | O | S | bond | 4-fluorophenyl | |
| 279 | CF₃ | H | CH₃ | H | H | O | —CH₂— | —CH₂CH₂— | H | O | S | bond | 4-chlorophenyl | |
| 280 | CF₃ | H | CH₃ | H | H | O | —CH₂— | —CH₂CH₂— | H | O | S | bond | 4-methylphenyl | |
| 281 | CF₃ | H | CH₃ | H | H | O | —CH₂— | —CH₂CH₂— | H | O | S | bond | 3-chlorophenyl | |
| 282 | CF₃ | H | CH₃ | H | H | O | —CH₂— | —CH₂CH₂— | H | O | S | bond | 3,5-dichlorophenyl | |
| 283 | CF₃ | H | CH₃ | H | H | O | —CH₂— | —CH₂CH₂— | H | O | S | bond | 3,4-dichlorophenyl | |
| 284 | CF₃ | H | CH₃ | H | H | O | —CH₂— | —CH₂CH₂— | H | O | S | bond | 2,4-dichlorophenyl | |
| 285 | CF₃ | H | CH₃ | H | H | O | —CH₂— | —CH₂CH₂— | H | O | S | bond | 2-chlorophenyl | |
| 286 | CF₃ | H | CH₃ | H | H | O | —CH₂— | —CH₂CH₂— | H | O | S | bond | 2,6-dichlorophenyl | |
| 287 | CF₃ | H | CH₃ | H | H | O | —CH₂— | —CH₂CH₂— | H | O | S | bond | 3-(trifluoromethyl)phenyl | |
| 288 | CF₃ | H | CH₃ | H | H | O | —CH₂— | —CH₂CH₂— | H | O | S | bond | 3-methylphenyl | |
| 289 | CF₃ | H | CH₃ | H | H | O | —CH₂— | —CH₂CH₂— | H | O | S | bond | 2-methylphenyl | |
| 290 | CF₃ | H | CH₃ | H | H | O | —CH₂— | —CH₂CH₂— | H | O | S | bond | 4-tert-butylphenyl | |
| 291 | CF₃ | H | CH₃ | H | H | O | —CH₂— | —CH₂CH₂— | H | O | S | bond | 4-nitrophenyl | |
| 292 | CF₃ | H | CH₃ | H | H | O | —CH₂— | —CH₂CH₂— | H | O | O | —CH₂— | pyridin-4-yl | 1.51* |
| 293 | CF₃ | H | CH₃ | H | H | O | —CH₂— | —CH₂CH₂— | H | O | O | —CH₂— | 2-thienyl | 3.23* |
| 294 | CH₃ | H | CH₃ | H | H | O | —CH₂CH₂— | —CH₂— | H | O | O | —CH₂— | trimethylsilyl | |
| 295 | CH₃ | H | CH₃ | H | H | O | —CH₂CH₂— | —CH₂— | H | O | O | bond | cyclohexyl | |
| 296 | CH₃ | H | CH₃ | H | H | O | —CH₂CH₂— | —CH₂— | H | O | O | bond | cyclopentyl | |
| 297 | CH₃ | H | CH₃ | H | H | O | —CH₂CH₂— | —CH₂— | H | O | O | —CH₂— | cyclopropyl | |
| 298 | CH₃ | H | CH₃ | H | H | O | —CH₂CH₂— | —CH₂— | H | O | O | —CH₂— | 2,2-dichlorocyclopropyl | |
| 299 | CH₃ | H | CH₃ | H | H | O | —CH₂CH₂— | —CH₂— | H | O | O | bond | 1,2,3,4-tetrahydronaphthalen-1-yl | |
| 300 | CH₃ | H | CH₃ | H | H | O | —CH₂CH₂— | —CH₂— | H | O | O | bond | decahydronaphthalen-1-yl | |
| 301 | CH₃ | H | CH₃ | H | H | O | —CH₂CH₂— | —CH₂— | H | O | O | bond | 2,3-dihydro-1H-inden-1-yl | |
| 302 | CH₃ | H | CH₃ | H | H | O | —CH₂CH₂— | —CH₂— | H | O | O | bond | 1-naphthyl | |
| 303 | CH₃ | H | CH₃ | H | H | O | —CH₂CH₂— | —CH₂— | H | O | O | bond | 2-naphthyl | |
| 304 | CH₃ | H | CH₃ | H | H | O | —CH₂CH₂— | —CH₂— | H | O | O | —CH₂— | phenyl | |
| 305 | CH₃ | H | CH₃ | H | H | O | —CH₂CH₂— | —CH₂— | H | O | O | —CH₂— | 4-fluorophenyl | |
| 306 | CH₃ | H | CH₃ | H | H | O | —CH₂CH₂— | —CH₂— | H | O | O | —CH₂— | 4-chlorophenyl | |
| 307 | CH₃ | H | CH₃ | H | H | O | —CH₂CH₂— | —CH₂— | H | O | O | —CH₂— | 4-methylphenyl | |
| 308 | CH₃ | H | CH₃ | H | H | O | —CH₂CH₂— | —CH₂— | H | O | O | —CH₂— | 4-methoxyphenyl | |
| 309 | CH₃ | H | CH₃ | H | H | O | —CH₂CH₂— | —CH₂— | H | O | O | —CH₂— | 2,4-dichlorophenyl | |
| 310 | CH₃ | H | CH₃ | H | H | O | —CH₂CH₂— | —CH₂— | H | O | O | —CH₂— | 3,5-dichlorophenyl | |
| 311 | CH₃ | H | CH₃ | H | H | O | —CH₂CH₂— | —CH₂— | H | O | O | —CH₂— | 2,6-dichlorophenyl | |
| 312 | CH₃ | H | CH₃ | H | H | O | —CH₂CH₂— | —CH₂— | H | O | O | —CH₂— | 2-chlorophenyl | |
| 313 | CH₃ | H | CH₃ | H | H | O | —CH₂CH₂— | —CH₂— | H | O | O | —CH₂— | 3-chlorophenyl | |
| 314 | CH₃ | H | CH₃ | H | H | O | —CH₂CH₂— | —CH₂— | H | O | O | —CH₂— | 3-(trifluoromethyl)phenyl | |
| 315 | CH₃ | H | CH₃ | H | H | O | —CH₂CH₂— | —CH₂— | H | O | O | —CH₂— | 3-methylphenyl | |

-continued (I)

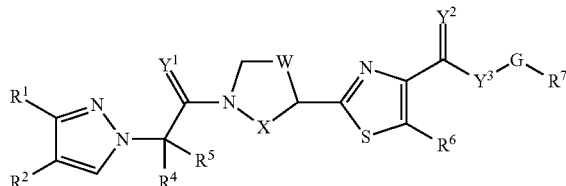

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 316 | $CH_3$ | H | $CH_3$ | H | H | O | —$CH_2CH_2$— | —$CH_2$— | H | O | O | —$CH_2$— | 2-methylphenyl | |
| 317 | $CH_3$ | H | $CH_3$ | H | H | O | —$CH_2CH_2$— | —$CH_2$— | H | O | O | —$CH_2$— | 4-nitrophenyl | |
| 318 | $CH_3$ | H | $CH_3$ | H | H | O | —$CH_2CH_2$— | —$CH_2$— | H | O | O | —$CH_2$— | 4-tert-butyl-phenyl | |
| 319 | $CH_3$ | H | $CH_3$ | H | H | O | —$CH_2CH_2$— | —$CH_2$— | H | O | S | —$CH_2$— | phenyl | |
| 320 | $CH_3$ | H | $CH_3$ | H | H | O | —$CH_2CH_2$— | —$CH_2$— | H | O | S | —$CH_2$— | 4-fluorophenyl | |
| 321 | $CH_3$ | H | $CH_3$ | H | H | O | —$CH_2CH_2$— | —$CH_2$— | H | O | S | —$CH_2$— | 4-chlorophenyl | |
| 322 | $CH_3$ | H | $CH_3$ | H | H | O | —$CH_2CH_2$— | —$CH_2$— | H | O | S | —$CH_2$— | 4-methylphenyl | |
| 323 | $CH_3$ | H | $CH_3$ | H | H | O | —$CH_2CH_2$— | —$CH_2$— | H | O | S | —$CH_2$— | 4-methoxy-phenyl | |
| 324 | $CH_3$ | H | $CH_3$ | H | H | O | —$CH_2CH_2$— | —$CH_2$— | H | O | S | —$CH_2$— | 2,4-dichloro-phenyl | |
| 325 | $CH_3$ | H | $CH_3$ | H | H | O | —$CH_2CH_2$— | —$CH_2$— | H | O | S | —$CH_2$— | 3,5-dichloro-phenyl | |
| 326 | $CH_3$ | H | $CH_3$ | H | H | O | —$CH_2CH_2$— | —$CH_2$— | H | O | S | —$CH_2$— | 2,6-dichloro-phenyl | |
| 327 | $CH_3$ | H | $CH_3$ | H | H | O | —$CH_2CH_2$— | —$CH_2$— | H | O | S | —$CH_2$— | 2-chlorophenyl | |
| 328 | $CH_3$ | H | $CH_3$ | H | H | O | —$CH_2CH_2$— | —$CH_2$— | H | O | S | —$CH_2$— | 3-chlorophenyl | |
| 329 | $CH_3$ | H | $CH_3$ | H | H | O | —$CH_2CH_2$— | —$CH_2$— | H | O | S | —$CH_2$— | 3-(trifluoro-methyl)phenyl | |
| 330 | $CH_3$ | H | $CH_3$ | H | H | O | —$CH_2CH_2$— | —$CH_2$— | H | O | S | —$CH_2$— | 3-methylphenyl | |
| 331 | $CH_3$ | H | $CH_3$ | H | H | O | —$CH_2CH_2$— | —$CH_2$— | H | O | S | —$CH_2$— | 2-methylphenyl | |
| 332 | $CH_3$ | H | $CH_3$ | H | H | O | —$CH_2CH_2$— | —$CH_2$— | H | O | S | —$CH_2$— | 4-nitrophenyl | |
| 333 | $CH_3$ | H | $CH_3$ | H | H | O | —$CH_2CH_2$— | —$CH_2$— | H | O | S | —$CH_2$— | 4-tert-butyl-phenyl | |
| 334 | $CH_3$ | H | $CH_3$ | H | H | O | —$CH_2CH_2$— | —$CH_2$— | H | O | O | —$CH(CH_3)$— | 4-fluorophenyl | |
| 335 | $CH_3$ | H | $CH_3$ | H | H | O | —$CH_2CH_2$— | —$CH_2$— | H | O | O | —$CH(CH_2CH_3)$— | 4-fluorophenyl | |
| 336 | $CH_3$ | H | $CH_3$ | H | H | O | —$CH_2CH_2$— | —$CH_2$— | H | O | O | —$CH_2CH_2$— | 4-fluorophenyl | |
| 337 | $CH_3$ | H | $CH_3$ | H | H | O | —$CH_2CH_2$— | —$CH_2$— | H | O | O | bond | phenyl | |
| 338 | $CH_3$ | H | $CH_3$ | H | H | O | —$CH_2CH_2$— | —$CH_2$— | H | O | O | bond | 4-fluorophenyl | |
| 339 | $CH_3$ | H | $CH_3$ | H | H | O | —$CH_2CH_2$— | —$CH_2$— | H | O | O | bond | 4-chlorophenyl | |
| 340 | $CH_3$ | H | $CH_3$ | H | H | O | —$CH_2CH_2$— | —$CH_2$— | H | O | O | bond | 4-methylphenyl | |
| 341 | $CH_3$ | H | $CH_3$ | H | H | O | —$CH_2CH_2$— | —$CH_2$— | H | O | O | bond | 3-chlorophenyl | |
| 342 | $CH_3$ | H | $CH_3$ | H | H | O | —$CH_2CH_2$— | —$CH_2$— | H | O | O | bond | 3,5-dichloro-phenyl | |
| 343 | $CH_3$ | H | $CH_3$ | H | H | O | —$CH_2CH_2$— | —$CH_2$— | H | O | O | bond | 3,4-dichloro-phenyl | |
| 344 | $CH_3$ | H | $CH_3$ | H | H | O | —$CH_2CH_2$— | —$CH_2$— | H | O | O | bond | 2,4-dichloro-phenyl | |
| 345 | $CH_3$ | H | $CH_3$ | H | H | O | —$CH_2CH_2$— | —$CH_2$— | H | O | O | bond | 2-chlorophenyl | |
| 346 | $CH_3$ | H | $CH_3$ | H | H | O | —$CH_2CH_2$— | —$CH_2$— | H | O | O | bond | 2,6-dichloro-phenyl | |
| 347 | $CH_3$ | H | $CH_3$ | H | H | O | —$CH_2CH_2$— | —$CH_2$— | H | O | O | bond | 3-(trifluoro-methyl)phenyl | |
| 348 | $CH_3$ | H | $CH_3$ | H | H | O | —$CH_2CH_2$— | —$CH_2$— | H | O | O | bond | 3-methylphenyl | |
| 349 | $CH_3$ | H | $CH_3$ | H | H | O | —$CH_2CH_2$— | —$CH_2$— | H | O | O | bond | 2-methylphenyl | |
| 350 | $CH_3$ | H | $CH_3$ | H | H | O | —$CH_2CH_2$— | —$CH_2$— | H | O | O | bond | 4-tert-butyl-phenyl | |
| 351 | $CH_3$ | H | $CH_3$ | H | H | O | —$CH_2CH_2$— | —$CH_2$— | H | O | O | bond | 4-nitrophenyl | |
| 352 | $CH_3$ | H | $CH_3$ | H | H | O | —$CH_2CH_2$— | —$CH_2$— | H | O | S | bond | phenyl | |
| 353 | $CH_3$ | H | $CH_3$ | H | H | O | —$CH_2CH_2$— | —$CH_2$— | H | O | S | bond | 4-fluorophenyl | |
| 354 | $CH_3$ | H | $CH_3$ | H | H | O | —$CH_2CH_2$— | —$CH_2$— | H | O | S | bond | 4-chlorophenyl | |
| 355 | $CH_3$ | H | $CH_3$ | H | H | O | —$CH_2CH_2$— | —$CH_2$— | H | O | S | bond | 4-methylphenyl | |
| 356 | $CH_3$ | H | $CH_3$ | H | H | O | —$CH_2CH_2$— | —$CH_2$— | H | O | S | bond | 3-chlorophenyl | |
| 357 | $CH_3$ | H | $CH_3$ | H | H | O | —$CH_2CH_2$— | —$CH_2$— | H | O | S | bond | 3,5-dichoro-phenyl | |
| 358 | $CH_3$ | H | $CH_3$ | H | H | O | —$CH_2CH_2$— | —$CH_2$— | H | O | S | bond | 3,4-dichloro-phenyl | |
| 359 | $CH_3$ | H | $CH_3$ | H | H | O | —$CH_2CH_2$— | —$CH_2$— | H | O | S | bond | 2,4-dichloro-phenyl | |
| 360 | $CH_3$ | H | $CH_3$ | H | H | O | —$CH_2CH_2$— | —$CH_2$— | H | O | S | bond | 2-chlorophenyl | |
| 361 | $CH_3$ | H | $CH_3$ | H | H | O | —$CH_2CH_2$— | —$CH_2$— | H | O | S | bond | 2,6-dichloro-phenyl | |
| 362 | $CH_3$ | H | $CH_3$ | H | H | O | —$CH_2CH_2$— | —$CH_2$— | H | O | S | bond | 3-(trifluoro-methyl)phenyl | |

-continued

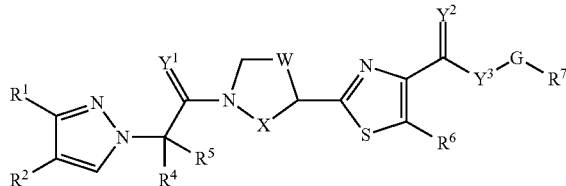
(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 363 | CH₃ | H | CH₃ | H | H | O | —CH₂CH₂— | —CH₂— | H | O | S | bond | 3-methylphenyl | |
| 364 | CH₃ | H | CH₃ | H | H | O | —CH₂CH₂— | —CH₂— | H | O | S | bond | 2-methylphenyl | |
| 365 | CH₃ | H | CH₃ | CH₃ | CH₃ | O | —CH₂CH₂— | —CH₂— | H | O | O | bond | cyclopentyl | |
| 366 | CH₃ | H | CH₃ | H | H | O | —CH₂CH₂— | —CH₂— | H | O | S | bond | 4-nitrophenyl | |
| 367 | CH₃ | H | CH₃ | H | H | O | —CH₂CH₂— | —CH₂— | H | O | O | —CH₂— | pyridin-4-yl | |
| 368 | CH₃ | H | CH₃ | CH₃ | CH₃ | O | —CH₂CH₂— | —CH₂— | H | O | O | bond | 1,2,3,4-tetrahydro-naphthalen-1-yl | 4.04* |
| 369 | CH₃ | H | CH₃ | CH₃ | CH₃ | O | —CH₂CH₂— | —CH₂— | H | O | O | —CH₂— | trimethylsilyl | 3.84* |
| 370 | CH₃ | H | CH₃ | CH₃ | CH₃ | O | —CH₂CH₂— | —CH₂— | H | O | O | bond | cyclohexyl | 3.78* |
| 371 | CH₃ | H | CH₃ | H | H | O | —CH₂CH₂— | —CH₂— | H | O | O | bond | 4-tert-butyl-phenyl | |
| 372 | CH₃ | H | CH₃ | CH₃ | CH₃ | O | —CH₂CH₂— | —CH₂— | H | O | O | —CH₂— | cyclopropyl | 3.86* |
| 373 | CH₃ | H | CH₃ | CH₃ | CH₃ | O | —CH₂CH₂— | —CH₂— | H | O | O | —CH₂— | 2,2-dichloro-cyclopropyl | |
| 374 | CH₃ | H | CH₃ | H | H | O | —CH₂CH₂— | —CH₂— | H | O | O | —CH₂— | 2-thienyl | |
| 375 | CH₃ | H | CH₃ | CH₃ | CH₃ | O | —CH₂CH₂— | —CH₂— | H | O | O | bond | decahydro-naphthalen-1-yl | |
| 376 | CH₃ | H | CH₃ | CH₃ | CH₃ | O | —CH₂CH₂— | —CH₂— | H | O | O | bond | 2,3-dihydro-1H-inden-1-yl | 3.68* |
| 377 | CH₃ | H | CH₃ | CH₃ | CH₃ | O | —CH₂CH₂— | —CH₂— | H | O | O | bond | 1-naphthalen | 3.82* |
| 378 | CH₃ | H | CH₃ | CH₃ | CH₃ | O | —CH₂CH₂— | —CH₂— | H | O | O | bond | 2-naphthyl | 3.73* |
| 379 | CH₃ | H | CH₃ | CH₃ | CH₃ | O | —CH₂CH₂— | —CH₂— | H | O | O | —CH₂— | phenyl | 3.19* |
| 380 | CH₃ | H | CH₃ | CH₃ | CH₃ | O | —CH₂CH₂— | —CH₂— | H | O | O | —CH₂— | 4-fluorophenyl | |
| 381 | CH₃ | H | CH₃ | CH₃ | CH₃ | O | —CH₂CH₂— | —CH₂— | H | O | O | —CH₂— | 4-chlorophenyl | |
| 382 | CH₃ | H | CH₃ | CH₃ | CH₃ | O | —CH₂CH₂— | —CH₂— | H | O | O | —CH₂— | 4-methylphenyl | |
| 383 | CH₃ | H | CH₃ | CH₃ | CH₃ | O | —CH₂CH₂— | —CH₂— | H | O | O | —CH₂— | 4-methoxy-phenyl | |
| 384 | CH₃ | H | CH₃ | CH₃ | CH₃ | O | —CH₂CH₂— | —CH₂— | H | O | O | —CH₂— | 2,4-dichloro-phenyl | |
| 385 | CH₃ | H | CH₃ | CH₃ | CH₃ | O | —CH₂CH₂— | —CH₂— | H | O | O | —CH₂— | 3,5-dichloro-phenyl | |
| 386 | CH₃ | H | CH₃ | CH₃ | CH₃ | O | —CH₂CH₂— | —CH₂— | H | O | O | —CH₂— | 2,6-dichloro-phenyl | |
| 387 | CH₃ | H | CH₃ | CH₃ | CH₃ | O | —CH₂CH₂— | —CH₂— | H | O | O | —CH₂— | 2-chlorophenyl | |
| 388 | CH₃ | H | CH₃ | CH₃ | CH₃ | O | —CH₂CH₂— | —CH₂— | H | O | O | —CH₂— | 3-chlorophenyl | |
| 389 | CH₃ | H | CH₃ | CH₃ | CH₃ | O | —CH₂CH₂— | —CH₂— | H | O | O | —CH₂— | 3-(trifluoro-methyl)phenyl | |
| 390 | CH₃ | H | CH₃ | CH₃ | CH₃ | O | —CH₂CH₂— | —CH₂— | H | O | O | —CH₂— | 3-methylphenyl | |
| 391 | CH₃ | H | CH₃ | CH₃ | CH₃ | O | —CH₂CH₂— | —CH₂— | H | O | O | —CH₂— | 2-methylphenyl | |
| 392 | CH₃ | H | CH₃ | CH₃ | CH₃ | O | —CH₂CH₂— | —CH₂— | H | O | O | —CH₂— | 4-nitrophenyl | |
| 393 | CH₃ | H | CH₃ | CH₃ | CH₃ | O | —CH₂CH₂— | —CH₂— | H | O | O | —CH₂— | 4-tert-butyl-phenyl | |
| 394 | CH₃ | H | CH₃ | CH₃ | CH₃ | O | —CH₂CH₂— | —CH₂— | H | O | S | —CH₂— | phenyl | |
| 395 | CH₃ | H | CH₃ | CH₃ | CH₃ | O | —CH₂CH₂— | —CH₂— | H | O | S | —CH₂— | 4-fluorophenyl | |
| 396 | CH₃ | H | CH₃ | CH₃ | CH₃ | O | —CH₂CH₂— | —CH₂— | H | O | S | —CH₂— | 4-chlorophenyl | |
| 397 | CH₃ | H | CH₃ | CH₃ | CH₃ | O | —CH₂CH₂— | —CH₂— | H | O | S | —CH₂— | 4-methylphenyl | |
| 398 | CH₃ | H | CH₃ | CH₃ | CH₃ | O | —CH₂CH₂— | —CH₂— | H | O | S | —CH₂— | 4-methoxy-phenyl | |
| 399 | CH₃ | H | CH₃ | CH₃ | CH₃ | O | —CH₂CH₂— | —CH₂— | H | O | S | —CH₂— | 2,4-dichloro-phenyl | |
| 400 | CH₃ | H | CH₃ | CH₃ | CH₃ | O | —CH₂CH₂— | —CH₂— | H | O | S | —CH₂— | 3,5-dichloro-phenyl | |
| 401 | CH₃ | H | CH₃ | CH₃ | CH₃ | O | —CH₂CH₂— | —CH₂— | H | O | S | —CH₂— | 2,6-dichloro-phenyl | |
| 402 | CH₃ | H | CH₃ | CH₃ | CH₃ | O | —CH₂CH₂— | —CH₂— | H | O | S | —CH₂— | 2-chlorophenyl | |
| 403 | CH₃ | H | CH₃ | CH₃ | CH₃ | O | —CH₂CH₂— | —CH₂— | H | O | O | —CH(CH₃)— | 4-fluorophenyl | 3.47* |
| 404 | CH₃ | H | CH₃ | CH₃ | CH₃ | O | —CH₂CH₂— | —CH₂— | H | O | O | —CH(CH₂CH₃)— | 4-fluorophenyl | |
| 405 | CH₃ | H | CH₃ | CH₃ | CH₃ | O | —CH₂CH₂— | —CH₂— | H | O | O | —CH₂CH₂— | 4-fluorophenyl | 3.42* |
| 406 | CH₃ | H | CH₃ | CH₃ | CH₃ | O | —CH₂CH₂— | —CH₂— | H | O | S | —CH₂— | 2-methylphenyl | |
| 407 | CH₃ | H | CH₃ | CH₃ | CH₃ | O | —CH₂CH₂— | —CH₂— | H | O | S | —CH₂— | 4-nitrophenyl | |
| 408 | CH₃ | H | CH₃ | CH₃ | CH₃ | O | —CH₂CH₂— | —CH₂— | H | O | S | —CH₂— | 4-tert-butyl-phenyl | |
| 409 | CH₃ | H | CH₃ | CH₃ | CH₃ | O | —CH₂CH₂— | —CH₂— | H | O | S | —CH₂— | 3-chlorophenyl | |
| 410 | CH₃ | H | CH₃ | CH₃ | CH₃ | O | —CH₂CH₂— | —CH₂— | H | O | S | —CH₂— | 3-(trifluoro-methyl)phenyl | |

-continued

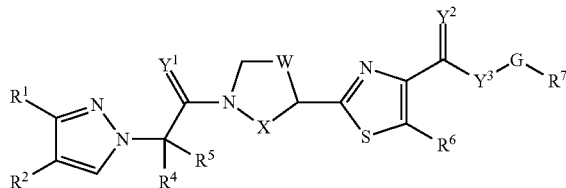
(I)

| EX NO | R1 | R2 | R3 | R4 | R5 | Y1 | X | W | R6 | Y2 | Y3 | G | R7 | log p |
|---|---|---|---|---|---|---|---|---|---|---|---|---|---|---|
| 411 | CH3 | H | CH3 | CH3 | CH3 | O | —CH2CH2— | —CH2— | H | O | S | —CH2— | 3-methylphenyl | |
| 412 | CH3 | H | CH3 | CH3 | CH3 | O | —CH2CH2— | —CH2— | H | O | O | bond | phenyl | 3.06* |
| 413 | CH3 | H | CH3 | CH3 | CH3 | O | —CH2CH2— | —CH2— | H | O | O | bond | 4-fluoropheny | 3.21* |
| 414 | CH3 | H | CH3 | CH3 | CH3 | O | —CH2CH2— | —CH2— | H | O | O | bond | 4-chlorophenyl | |
| 415 | CH3 | H | CH3 | CH3 | CH3 | O | —CH2CH2— | —CH2— | H | O | O | bond | 4-methylphenyl | |
| 416 | CH3 | H | CH3 | CH3 | CH3 | O | —CH2CH2— | —CH2— | H | O | O | bond | 3-chlorophenyl | |
| 417 | CH3 | H | CH3 | CH3 | CH3 | O | —CH2CH2— | —CH2— | H | O | O | bond | 3,5-dichloro-phenyl | |
| 418 | CH3 | H | CH3 | CH3 | CH3 | O | —CH2CH2— | —CH2— | H | O | O | bond | 3,4-dichloro-phenyl | |
| 419 | CH3 | H | CH3 | CH3 | CH3 | O | —CH2CH2— | —CH2— | H | O | O | bond | 2,4-dichloro-phenyl | |
| 420 | CH3 | H | CH3 | CH3 | CH3 | O | —CH2CH2— | —CH2— | H | O | O | bond | 2-chlorophenyl | |
| 421 | CH3 | H | CH3 | CH3 | CH3 | O | —CH2CH2— | —CH2— | H | O | O | bond | 2,6-dichloro-phenyl | |
| 422 | CH3 | H | CH3 | CH3 | CH3 | O | —CH2CH2— | —CH2— | H | O | O | bond | 3-(trifluoro-phenyl) | |
| 423 | CH3 | H | CH3 | CH3 | CH3 | O | —CH2CH2— | —CH2— | H | O | O | bond | 3-methylphenyl | |
| 424 | CH3 | H | CH3 | CH3 | CH3 | O | —CH2CH2— | —CH2— | H | O | O | bond | 2-methylphenyl | |
| 425 | CH3 | H | CH3 | CH3 | CH3 | O | —CH2CH2— | —CH2— | H | O | O | bond | 4-tert-butyl-phenyl | |
| 426 | CH3 | H | CH3 | CH3 | CH3 | O | —CH2CH2— | —CH2— | H | O | O | bond | 4-nitrophenyl | |
| 427 | CH3 | H | CH3 | CH3 | CH3 | O | —CH2CH2— | —CH2— | H | O | S | bond | phenyl | |
| 428 | CH3 | H | CH3 | CH3 | CH3 | O | —CH2CH2— | —CH2— | H | O | S | bond | 4-fluorophenyl | |
| 429 | CH3 | H | CH3 | CH3 | CH3 | O | —CH2CH2— | —CH2— | H | O | S | bond | 4-chlorophenyl | |
| 430 | CH3 | H | CH3 | CH3 | CH3 | O | —CH2CH2— | —CH2— | H | O | S | bond | 4-methylphenyl | |
| 431 | CH3 | H | CH3 | CH3 | CH3 | O | —CH2CH2— | —CH2— | H | O | S | bond | 3-chlorophenyl | |
| 432 | CH3 | H | CH3 | CH3 | CH3 | O | —CH2CH2— | —CH2— | H | O | S | bond | 3,5-dichloro-phenyl | |
| 433 | CH3 | H | CH3 | CH3 | CH3 | O | —CH2CH2— | —CH2— | H | O | S | bond | 3,4-dichloro-phenyl | |
| 434 | CH3 | H | CH3 | CH3 | CH3 | O | —CH2CH2— | —CH2— | H | O | S | bond | 2,4-dichloro-phenyl | |
| 435 | CH3 | H | CH3 | CH3 | CH3 | O | —CH2CH2— | —CH2— | H | O | S | bond | 2-chlorophenyl | |
| 436 | CH3 | H | CH3 | CH3 | CH3 | O | —CH2CH2— | —CH2— | H | O | S | bond | 2,6-dichloro-phenyl | |
| 437 | CH3 | H | CH3 | CH3 | CH3 | O | —CH2CH2— | —CH2— | H | O | S | bond | 3-(trifluoro-methyl)phenyl | |
| 438 | CH3 | H | CH3 | CH3 | CH3 | O | —CH2CH2— | —CH2— | H | O | S | bond | 3-methylphenyl | |
| 439 | CH3 | H | CH3 | CH3 | CH3 | O | —CH2CH2— | —CH2— | H | O | S | bond | 2-methylphenyl | |
| 440 | CH3 | H | CH3 | CH3 | CH3 | O | —CH2CH2— | —CH2— | H | O | S | bond | 4-tert-butyl-phenyl | |
| 441 | CH3 | H | CH3 | CH3 | CH3 | O | —CH2CH2— | —CH2— | H | O | S | bond | 4-nitrophenyl | |
| 442 | CH3 | H | CH3 | CH3 | CH3 | O | —CH2CH2— | —CH2— | H | O | O | —CH2— | pyridin-4-yl | 1.33* |
| 443 | CH3 | H | CH3 | CH3 | CH3 | O | —CH2CH2— | —CH2— | H | O | O | —CH2— | 2-thienyl | 3.06* |
| 444 | CF3 | H | CH3 | H | H | O | —CH2CH2— | —CH2— | CH3 | O | O | —CH2— | trimethylsilyl | |
| 445 | CF3 | H | CH3 | H | H | O | —CH2CH2— | —CH2— | CH3 | O | O | bond | cyclohexyl | |
| 446 | CF3 | H | CH3 | H | H | O | —CH2CH2— | —CH2— | CH3 | O | O | bond | cyclopentyl | |
| 447 | CF3 | H | CH3 | H | H | O | —CH2CH2— | —CH2— | CH3 | O | O | —CH2— | cyclopropyl | |
| 448 | CF3 | H | CH3 | H | H | O | —CH2CH2— | —CH2— | CH3 | O | O | —CH2— | 2,2-dichloro-cyclopropyl | |
| 449 | CF3 | H | CH3 | H | H | O | —CH2CH2— | —CH2— | CH3 | O | O | bond | 1,2,3,4-tetrahydro-naphthalen-1-yl | |
| 450 | CF3 | H | CH3 | H | H | O | —CH2CH2— | —CH2— | CH3 | O | O | bond | decahydro-naphthalen-1-yl | |
| 451 | CF3 | H | CH3 | H | H | O | —CH2CH2— | —CH2— | CH3 | O | O | bond | 2,3-dihydro-1H-inden-1-yl | |
| 452 | CF3 | H | CH3 | H | H | O | —CH2CH2— | —CH2— | CH3 | O | O | bond | 1-naphthyl | |
| 453 | CF3 | H | CH3 | H | H | O | —CH2CH2— | —CH2— | CH3 | O | O | bond | 2-naphthyl | |
| 454 | CF3 | H | CH3 | H | H | O | —CH2CH2— | —CH2— | CH3 | O | O | —CH2— | phenyl | |
| 455 | CF3 | H | CH3 | H | H | O | —CH2CH2— | —CH2— | CH3 | O | O | —CH2— | 4-fluorophenyl | |
| 456 | CF3 | H | CH3 | H | H | O | —CH2CH2— | —CH2— | CH3 | O | O | —CH2— | 4-chlorophenyl | |
| 457 | CF3 | H | CH3 | H | H | O | —CH2CH2— | —CH2— | CH3 | O | O | —CH2— | 4-methylphenyl | |
| 458 | CF3 | H | CH3 | H | H | O | —CH2CH2— | —CH2— | CH3 | O | O | —CH2— | 4-methoxy-phenyl | |

-continued

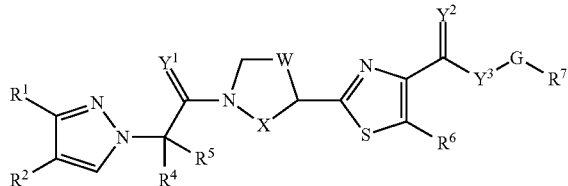

(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 459 | CF₃ | H | CH₃ | H | H | O | —CH₂CH₂— | —CH₂— | CH₃ | O | O | —CH₂— | 2,4-dichlorophenyl | |
| 460 | CF₃ | H | CH₃ | H | H | O | —CH₂CH₂— | —CH₂— | CH₃ | O | O | —CH₂— | 3,5-dichlorophenyl | |
| 461 | CF₃ | H | CH₃ | H | H | O | —CH₂CH₂— | —CH₂— | CH₃ | O | O | —CH₂— | 2,6-dichlorophenyl | |
| 462 | CF₃ | H | CH₃ | H | H | O | —CH₂CH₂— | —CH₂— | CH₃ | O | O | —CH₂— | 2-chlorophenyl | |
| 463 | CF₃ | H | CH₃ | H | H | O | —CH₂CH₂— | —CH₂— | CH₃ | O | O | —CH₂— | 3-chlorophenyl | |
| 464 | CF₃ | H | CH₃ | H | H | O | —CH₂CH₂— | —CH₂— | CH₃ | O | O | —CH₂— | 3-(trifluoromethyl)phenyl | |
| 465 | CF₃ | H | CH₃ | H | H | O | —CH₂CH₂— | —CH₂— | CH₃ | O | O | —CH₂— | 3-methylphenyl | |
| 466 | CF₃ | H | CH₃ | H | H | O | —CH₂CH₂— | —CH₂— | CH₃ | O | O | —CH₂— | 2-methylphenyl | |
| 467 | CF₃ | H | CH₃ | H | H | O | —CH₂CH₂— | —CH₂— | CH₃ | O | O | —CH₂— | 4-nitrophenyl | |
| 468 | CF₃ | H | CH₃ | H | H | O | —CH₂CH₂— | —CH₂— | CH₃ | O | O | —CH₂— | 4-tert-butylphenyl | |
| 469 | CF₃ | H | CH₃ | H | H | O | —CH₂CH₂— | —CH₂— | CH₃ | O | S | —CH₂— | phenyl | |
| 470 | CF₃ | H | CH₃ | H | H | O | —CH₂CH₂— | —CH₂— | CH₃ | O | S | —CH₂— | 4-fluorophenyl | |
| 471 | CF₃ | H | CH₃ | H | H | O | —CH₂CH₂— | —CH₂— | CH₃ | O | S | —CH₂— | 4-chlorophenyl | |
| 472 | CF₃ | H | CH₃ | H | H | O | —CH₂CH₂— | —CH₂— | CH₃ | O | S | —CH₂— | 4-methylphenyl | |
| 473 | CF₃ | H | CH₃ | H | H | O | —CH₂CH₂— | —CH₂— | CH₃ | O | S | —CH₂— | 4-methoxyphenyl | |
| 474 | CF₃ | H | CH₃ | H | H | O | —CH₂CH₂— | —CH₂— | CH₃ | O | S | —CH₂— | 2,4-dichlorophenyl | |
| 475 | CF₃ | H | CH₃ | H | H | O | —CH₂CH₂— | —CH₂— | CH₃ | O | S | —CH₂— | 3,5-dichlorophenyl | |
| 476 | CF₃ | H | CH₃ | H | H | O | —CH₂CH₂— | —CH₂— | CH₃ | O | S | —CH₂— | 2,6-dichlorophenyl | |
| 477 | CF₃ | H | CH₃ | H | H | O | —CH₂CH₂— | —CH₂— | CH₃ | O | S | —CH₂— | 2-chlorophenyl | |
| 478 | CF₃ | H | CH₃ | H | H | O | —CH₂CH₂— | —CH₂— | CH₃ | O | S | —CH₂— | 3-chlorophenyl | |
| 479 | CF₃ | H | CH₃ | H | H | O | —CH₂CH₂— | —CH₂— | CH₃ | O | S | —CH₂— | 3-(trifluoromethyl)phenyl | |
| 480 | CF₃ | H | CH₃ | H | H | O | —CH₂CH₂— | —CH₂— | CH₃ | O | S | —CH₂— | 3-methylphenyl | |
| 481 | CF₃ | H | CH₃ | H | H | O | —CH₂CH₂— | —CH₂— | CH₃ | O | S | —CH₂— | 2-methylphenyl | |
| 482 | CF₃ | H | CH₃ | H | H | O | —CH₂CH₂— | —CH₂— | CH₃ | O | S | —CH₂— | 4-nitrophenyl | |
| 483 | CF₃ | H | CH₃ | H | H | O | —CH₂CH₂— | —CH₂— | CH₃ | O | S | —CH₂— | 4-tert-butylphenyl | |
| 484 | CF₃ | H | CH₃ | H | H | O | —CH₂CH₂— | —CH₂— | CH₃ | O | O | —CH(CH₃)— | 4-fluorophenyl | |
| 485 | CF₃ | H | CH₃ | H | H | O | —CH₂CH₂— | —CH₂— | CH₃ | O | O | —CH(CH₂CH₃)— | 4-fluorophenyl | |
| 486 | CF₃ | H | CH₃ | H | H | O | —CH₂CH₂— | —CH₂— | CH₃ | O | O | —CH₂CH₂— | 4-fluorophenyl | |
| 487 | CF₃ | H | CH₃ | H | H | O | —CH₂CH₂— | —CH₂— | CH₃ | O | O | bond | phenyl | |
| 488 | CF₃ | H | CH₃ | H | H | O | —CH₂CH₂— | —CH₂— | CH₃ | O | O | bond | 4-fluorophenyl | |
| 489 | CF₃ | H | CH₃ | H | H | O | —CH₂CH₂— | —CH₂— | CH₃ | O | O | bond | 4-chlorophenyl | |
| 490 | CF₃ | H | CH₃ | H | H | O | —CH₂CH₂— | —CH₂— | CH₃ | O | O | bond | 4-methylphenyl | |
| 491 | CF₃ | H | CH₃ | H | H | O | —CH₂CH₂— | —CH₂— | CH₃ | O | O | bond | 3-chlorophenyl | |
| 492 | CF₃ | H | CH₃ | H | H | O | —CH₂CH₂— | —CH₂— | CH₃ | O | O | bond | 3,5-dichlorophenyl | |
| 493 | CF₃ | H | CH₃ | H | H | O | —CH₂CH₂— | —CH₂— | CH₃ | O | O | bond | 3,4-dichlorophenyl | |
| 494 | CF₃ | H | CH₃ | H | H | O | —CH₂CH₂— | —CH₂— | CH₃ | O | O | bond | 2,4-dichlorophenyl | |
| 495 | CF₃ | H | CH₃ | H | H | O | —CH₂CH₂— | —CH₂— | CH₃ | O | O | bond | 2-chlorophenyl | |
| 496 | CF₃ | H | CH₃ | H | H | O | —CH₂CH₂— | —CH₂— | CH₃ | O | O | bond | 2,6-dichlorophenyl | |
| 497 | CF₃ | H | CH₃ | H | H | O | —CH₂CH₂— | —CH₂— | CH₃ | O | O | bond | 3-(trifluoromethyl)phenyl | |
| 498 | CF₃ | H | CH₃ | H | H | O | —CH₂CH₂— | —CH₂— | CH₃ | O | O | bond | 3-methylphenyl | |
| 499 | CF₃ | H | CH₃ | H | H | O | —CH₂CH₂— | —CH₂— | CH₃ | O | O | bond | 2-methylphenyl | |
| 500 | CF₃ | H | CH₃ | H | H | O | —CH₂CH₂— | —CH₂— | CH₃ | O | O | bond | 4-tert-butylphenyl | |
| 501 | CF₃ | H | CH₃ | H | H | O | —CH₂CH₂— | —CH₂— | CH₃ | O | O | bond | 4-nitrophenyl | |
| 502 | CF₃ | H | CH₃ | H | H | O | —CH₂CH₂— | —CH₂— | CH₃ | O | S | bond | phenyl | |
| 503 | CF₃ | H | CH₃ | H | H | O | —CH₂CH₂— | —CH₂— | CH₃ | O | S | bond | 4-fluorophenyl | |
| 504 | CF₃ | H | CH₃ | H | H | O | —CH₂CH₂— | —CH₂— | CH₃ | O | S | bond | 4-chlorophenyl | |
| 505 | CF₃ | H | CH₃ | H | H | O | —CH₂CH₂— | —CH₂— | CH₃ | O | S | bond | 4-methylphenyl | |
| 506 | CF₃ | H | CH₃ | H | H | O | —CH₂CH₂— | —CH₂— | CH₃ | O | S | bond | 3-chlorophenyl | |

-continued

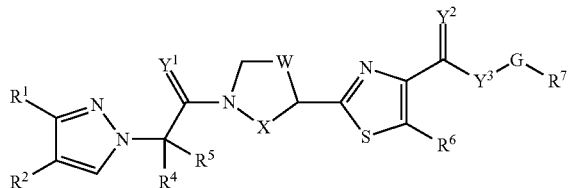
(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 507 | CF₃ | H | CH₃ | H | H | O | —CH₂CH₂— | —CH₂— | CH₃ | O | S | bond | 3,5-dichlorophenyl | |
| 508 | CF₃ | H | CH₃ | H | H | O | —CH₂CH₂— | —CH₂— | CH₃ | O | S | bond | 3,4-dichlorophenyl | |
| 509 | CF₃ | H | CH₃ | H | H | O | —CH₂CH₂— | —CH₂— | CH₃ | O | S | bond | 2,4-dichlorophenyl | |
| 510 | CF₃ | H | CH₃ | H | H | O | —CH₂CH₂— | —CH₂— | CH₃ | O | S | bond | 2-chlorophenyl | |
| 511 | CF₃ | H | CH₃ | H | H | O | —CH₂CH₂— | —CH₂— | CH₃ | O | S | bond | 2,6-dichlorophenyl | |
| 512 | CF₃ | H | CH₃ | H | H | O | —CH₂CH₂— | —CH₂— | CH₃ | O | S | bond | 3-(trifluoromethyl)phenyl | |
| 513 | CF₃ | H | CH₃ | H | H | O | —CH₂CH₂— | —CH₂— | CH₃ | O | S | bond | 3-methylphenyl | |
| 514 | CF₃ | H | CH₃ | H | H | O | —CH₂CH₂— | —CH₂— | CH₃ | O | S | bond | 2-methylphenyl | |
| 515 | CF₃ | H | CH₃ | H | H | O | —CH₂CH₂— | —CH₂— | CH₃ | O | S | bond | 4-tert-butylphenyl | |
| 516 | CF₃ | H | CH₃ | H | H | O | —CH₂CH₂— | —CH₂— | CH₃ | O | S | bond | 4-nitrophenyl | |
| 517 | CF₃ | H | CH₃ | H | H | O | —CH₂CH₂— | —CH₂— | CH₃ | O | O | —CH₂— | pyridin-4-yl | |
| 518 | CF₃ | H | CH₃ | H | H | O | —CH₂CH₂— | —CH₂— | CH₃ | O | O | —CH₂— | 2-thienyl | |
| 519 | CF₃ | H | CH₃ | H | H | O | —CH₂CH₂— | —CH₂— | CH₃ | O | S | bond | cyclohexyl | |
| 520 | CF₃ | H | CH₃ | H | H | O | —CH₂CH₂— | —CH₂— | CH₃ | O | S | bond | 1-naphthyl | |
| 521 | CF₃ | H | CH₃ | H | H | O | bond | —CH₂CH₂CH₂— | H | O | O | —CH₂— | trimethylsilyl | |
| 522 | CF₃ | H | CH₃ | H | H | O | bond | —CH₂CH₂CH₂— | H | O | O | bond | cyclohexyl | |
| 523 | CF₃ | H | CH₃ | H | H | O | bond | —CH₂CH₂CH₂— | H | O | O | bond | cyclopentyl | |
| 524 | CF₃ | H | CH₃ | H | H | O | bond | —CH₂CH₂CH₂— | H | O | O | —CH₂— | cyclopropyl | |
| 525 | CF₃ | H | CH₃ | H | H | O | bond | —CH₂CH₂CH₂— | H | O | O | —CH₂— | 2,2-dichloropropyl | |
| 526 | CF₃ | H | CH₃ | H | H | O | bond | —CH₂CH₂CH₂— | H | O | O | bond | 1,2,3,4-tetrahydronaphthalen-1-yl | |
| 527 | CF₃ | H | CH₃ | H | H | O | bond | —CH₂CH₂CH₂— | H | O | O | bond | decahydronaphthalen-1-yl | |
| 528 | CF₃ | H | CH₃ | H | H | O | bond | —CH₂CH₂CH₂— | H | O | O | bond | 2,3-dihydro-1H-inden-1-yl | |
| 529 | CF₃ | H | CH₃ | H | H | O | bond | —CH₂CH₂CH₂— | H | O | O | bond | 1-naphthyl | |
| 530 | CF₃ | H | CH₃ | H | H | O | bond | —CH₂CH₂CH₂— | H | O | O | bond | 2-naphthyl | |
| 531 | CF₃ | H | CH₃ | H | H | O | bond | —CH₂CH₂CH₂— | H | O | O | —CH₂— | phenyl | |
| 532 | CF₃ | H | CH₃ | H | H | O | bond | —CH₂CH₂CH₂— | H | O | O | —CH₂— | 4-fluorophenyl | |
| 533 | CF₃ | H | CH₃ | H | H | O | bond | —CH₂CH₂CH₂— | H | O | O | —CH₂— | 4-chlorophenyl | |
| 534 | CF₃ | H | CH₃ | H | H | O | bond | —CH₂CH₂CH₂— | H | O | O | —CH₂— | 4-methylphenyl | |
| 535 | CF₃ | H | CH₃ | H | H | O | bond | —CH₂CH₂CH₂— | H | O | O | —CH₂— | 4-methoxyphenyl | |
| 536 | CF₃ | H | CH₃ | H | H | O | bond | —CH₂CH₂CH₂— | H | O | O | —CH₂— | 2,4-dichlorophenyl | |
| 537 | CF₃ | H | CH₃ | H | H | O | bond | —CH₂CH₂CH₂— | H | O | O | —CH₂— | 3,5-dichlorophenyl | |
| 538 | CF₃ | H | CH₃ | H | H | O | bond | —CH₂CH₂CH₂— | H | O | O | —CH₂— | 2,6-dichlorophenyl | |
| 539 | CF₃ | H | CH₃ | H | H | O | bond | —CH₂CH₂CH₂— | H | O | O | —CH₂— | 2-chlorophenyl | |
| 540 | CF₃ | H | CH₃ | H | H | O | bond | —CH₂CH₂CH₂— | H | O | O | —CH₂— | 3-chlorophenyl | |
| 541 | CF₃ | H | CH₃ | H | H | O | bond | —CH₂CH₂CH₂— | H | O | O | —CH₂— | 3-(trifluoromethyl)phenyl | |
| 542 | CF₃ | H | CH₃ | H | H | O | bond | —CH₂CH₂CH₂— | H | O | O | —CH₂— | 3-methylphenyl | |
| 543 | CF₃ | H | CH₃ | H | H | O | bond | —CH₂CH₂CH₂— | H | O | O | —CH₂— | 2-methylphenyl | |
| 544 | CF₃ | H | CH₃ | H | H | O | bond | —CH₂CH₂CH₂— | H | O | O | —CH₂— | 4-nitrophenyl | |
| 545 | CF₃ | H | CH₃ | H | H | O | bond | —CH₂CH₂CH₂— | H | O | O | —CH₂— | 4-tert-butylphenyl | |
| 546 | CF₃ | H | CH₃ | H | H | O | bond | —CH₂CH₂CH₂— | H | O | S | —CH₂— | phenyl | |
| 547 | CF₃ | H | CH₃ | H | H | O | bond | —CH₂CH₂CH₂— | H | O | S | —CH₂— | 4-fluorophenyl | |
| 548 | CF₃ | H | CH₃ | H | H | O | bond | —CH₂CH₂CH₂— | H | O | S | —CH₂— | 4-chlorophenyl | |
| 549 | CF₃ | H | CH₃ | H | H | O | bond | —CH₂CH₂CH₂— | H | O | S | —CH₂— | 4-methylphenyl | |
| 550 | CF₃ | H | CH₃ | H | H | O | bond | —CH₂CH₂CH₂— | H | O | S | —CH₂— | 4-methoxyphenyl | |
| 551 | CF₃ | H | CH₃ | H | H | O | bond | —CH₂CH₂CH₂— | H | O | S | —CH₂— | 2,4-dichlorophenyl | |
| 552 | CF₃ | H | CH₃ | H | H | O | bond | —CH₂CH₂CH₂— | H | O | S | —CH₂— | 3,5-dichlorophenyl | |

-continued

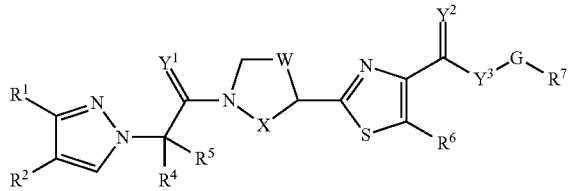

(I)

| EX NO | R1 | R2 | R3 | R4 | R5 | Y1 | X | W | R6 | Y2 | Y3 | G | R7 | log p |
|---|---|---|---|---|---|---|---|---|---|---|---|---|---|---|
| 553 | CF3 | H | CH3 | H | H | O | bond | —CH2CH2CH2— | H | O | S | —CH2— | 2,6-dichloro-phenyl | |
| 554 | CF3 | H | CH3 | H | H | O | bond | —CH2CH2CH2— | H | O | S | —CH2— | 2-chlorophenyl | |
| 555 | CF3 | H | CH3 | H | H | O | bond | —CH2CH2CH2— | H | O | S | —CH2— | 3-chlorophenyl | |
| 556 | CF3 | H | CH3 | H | H | O | bond | —CH2CH2CH2— | H | O | S | —CH2— | 3-(trifluoro-methyl)phenyl | |
| 557 | CF3 | H | CH3 | H | H | O | bond | —CH2CH2CH2— | H | O | S | —CH2— | 3-methylphenyl | |
| 558 | CF3 | H | CH3 | H | H | O | bond | —CH2CH2CH2— | H | O | S | —CH2— | 2-methylphenyl | |
| 559 | CF3 | H | CH3 | H | H | O | bond | —CH2CH2CH2— | H | O | S | —CH2— | 4-nitrophenyl | |
| 560 | CF3 | H | CH3 | H | H | O | bond | —CH2CH2CH2— | H | O | S | —CH2— | 4-tert-butyl-phenyl | |
| 561 | CF3 | H | CH3 | H | H | O | bond | —CH2CH2CH2— | H | O | O | —CH(CH3)— | 4-fluorophenyl | |
| 562 | CF3 | H | CH3 | H | H | O | bond | —CH2CH2CH2— | H | O | O | —CH(CH2CH3)— | 4-fluorophenyl | |
| 563 | CF3 | H | CH3 | H | H | O | bond | —CH2CH2CH2— | H | O | O | —CH2CH2— | 4-fluorophenyl | |
| 564 | CF3 | H | CH3 | H | H | O | bond | —CH2CH2CH2— | H | O | O | bond | phenyl | |
| 565 | CF3 | H | CH3 | H | H | O | bond | —CH2CH2CH2— | H | O | O | bond | 4-fluorophenyl | |
| 566 | CF3 | H | CH3 | H | H | O | bond | —CH2CH2CH2— | H | O | O | bond | 4-chlorophenyl | |
| 567 | CF3 | H | CH3 | H | H | O | bond | —CH2CH2CH2— | H | O | O | bond | 4-methylphenyl | |
| 568 | CF3 | H | CH3 | H | H | O | bond | —CH2CH2CH2— | H | O | O | bond | 3-chlorophenyl | |
| 569 | CF3 | H | CH3 | H | H | O | bond | —CH2CH2CH2— | H | O | O | bond | 3,5-dichloro-phenyl | |
| 570 | CF3 | H | CH3 | H | H | O | bond | —CH2CH2CH2— | H | O | O | bond | 3,4-dichloro-phenyl | |
| 571 | CF3 | H | CH3 | H | H | O | bond | —CH2CH2CH2— | H | O | O | bond | 2,4-dichloro phenyl | |
| 572 | CF3 | H | CH3 | H | H | O | bond | —CH2CH2CH2— | H | O | O | bond | 2-chlorophenyl | |
| 573 | CF3 | H | CH3 | H | H | O | bond | —CH2CH2CH2— | H | O | O | bond | 2,6-dichloro-phenyl | |
| 574 | CF3 | H | CH3 | H | H | O | bond | —CH2CH2CH2— | H | O | O | bond | 3-(trifluoro-methyl)phenyl | |
| 575 | CF3 | H | CH3 | H | H | O | bond | —CH2CH2CH2— | H | O | O | bond | 3-methylphenyl | |
| 576 | CF3 | H | CH3 | H | H | O | bond | —CH2CH2CH2— | H | O | O | bond | 2-methylphenyl | |
| 577 | CF3 | H | CH3 | H | H | O | bond | —CH2CH2CH2— | H | O | O | bond | 4-tert-butyl-phenyl | |
| 578 | CF3 | H | CH3 | H | H | O | bond | —CH2CH2CH2— | H | O | O | bond | 4-nitrophenyl | |
| 579 | CF3 | H | CH3 | H | H | O | bond | —CH2CH2CH2— | H | O | S | bond | phenyl | |
| 580 | CF3 | H | CH3 | H | H | O | bond | —CH2CH2CH2— | H | O | S | bond | 4-fluorophenyl | |
| 581 | CF3 | H | CH3 | H | H | O | bond | —CH2CH2CH2— | H | O | S | bond | 4-chlorophenyl | |
| 582 | CF3 | H | CH3 | H | H | O | bond | —CH2CH2CH2— | H | O | S | bond | 4-methylphenyl | |
| 583 | CF3 | H | CH3 | H | H | O | bond | —CH2CH2CH2— | H | O | S | bond | 3-chlorophenyl | |
| 584 | CF3 | H | CH3 | H | H | O | bond | —CH2CH2CH2— | H | O | S | bond | 3,5-dichloro-phenyl | |
| 585 | CF3 | H | CH3 | H | H | O | bond | —CH2CH2CH2— | H | O | S | bond | 3,4-dichloro-phenyl | |
| 586 | CF3 | H | CH3 | H | H | O | bond | —CH2CH2CH2— | H | O | S | bond | 2,4-dichloro-phenyl | |
| 587 | CF3 | H | CH3 | H | H | O | bond | —CH2CH2CH2— | H | O | S | bond | 2-chlorophenyl | |
| 588 | CF3 | H | CH3 | H | H | O | bond | —CH2CH2CH2— | H | O | S | bond | 2,6-dichloro-phenyl | |
| 589 | CF3 | H | CH3 | H | H | O | bond | —CH2CH2CH2— | H | O | S | bond | 3-(trifluoro-methyl)phenyl | |
| 590 | CF3 | H | CH3 | H | H | O | bond | —CH2CH2CH2— | H | O | S | bond | 3-methylphenyl | |
| 591 | CF3 | H | CH3 | H | H | O | bond | —CH2CH2CH2— | H | O | S | bond | 2-methylphenyl | |
| 592 | CF3 | H | CH3 | H | H | O | bond | —CH2CH2CH2— | H | O | S | bond | 4-tert-butyl-phenyl | |
| 593 | CF3 | H | CH3 | H | H | O | bond | —CH2CH2CH2— | H | O | S | bond | 4-nitrophenyl | |
| 594 | CF3 | H | CH3 | H | H | O | bond | —CH2CH2CH2— | H | O | O | —CH2— | pyridin-4-yl | |
| 595 | CF3 | H | CH3 | H | H | O | bond | —CH2CH2CH2— | H | O | O | —CH2— | 2-thienyl | |
| 596 | CF3 | H | CH3 | H | H | O | bond | —CH2CH2CH2— | H | O | S | bond | cyclohexyl | |
| 597 | CF3 | H | CH3 | H | H | O | bond | —CH2CH2CH2— | H | O | S | bond | 1-naphthyl | |
| 598 | CF3 | H | CH3 | H | CH3 | O | —CH2CH2— | —CH2— | H | O | O | —CH2— | trimethysilyl | |
| 599 | CF3 | H | CH3 | H | CH3 | O | —CH2CH2— | —CH2— | H | O | O | bond | cyclohexyl | |
| 600 | CF3 | H | CH3 | H | CH3 | O | —CH2CH2— | —CH2— | H | O | O | bond | cyclopentyl | |
| 601 | CF3 | H | CH3 | H | CH3 | O | —CH2CH2— | —CH2— | H | O | O | —CH2— | cyclopropyl | |
| 602 | CF3 | H | CH3 | H | CH3 | O | —CH2CH2— | —CH2— | H | O | O | —CH2— | 2,2-dichloro-cyclopropyl | |

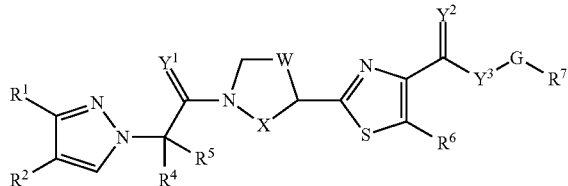

(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 603 | CF₃ | H | CH₃ | H | CH₃ | O | —CH₂CH₂— | —CH₂— | H | O | O | bond | 1,2,3,4-tetrahydro-naphthalen-1-yl | |
| 604 | CF₃ | H | CH₃ | H | CH₃ | O | —CH₂CH₂— | —CH₂— | H | O | O | bond | 1decahydro-napthalen-1-yl | |
| 605 | CF₃ | H | CH₃ | H | CH₃ | O | —CH₂CH₂— | —CH₂— | H | O | O | bond | 2,3-dihydro-1H-inden-1-yl | |
| 606 | CF₃ | H | CH₃ | H | CH₃ | O | —CH₂CH₂— | —CH₂— | H | O | O | bond | 1-naphthyl | |
| 607 | CF₃ | H | CH₃ | H | CH₃ | O | —CH₂CH₂— | —CH₂— | H | O | O | bond | 2-naphthyl | |
| 608 | CF₃ | H | CH₃ | H | CH₃ | O | —CH₂CH₂— | —CH₂— | H | O | O | —CH₂— | phenyl | |
| 609 | CF₃ | H | CH₃ | H | CH₃ | O | —CH₂CH₂— | —CH₂— | H | O | O | —CH₂— | 4-fluorophenyl | |
| 610 | CF₃ | H | CH₃ | H | CH₃ | O | —CH₂CH₂— | —CH₂— | H | O | O | —CH₂— | 4-chlorophenyl | |
| 611 | CF₃ | H | CH₃ | H | CH₃ | O | —CH₂CH₂— | —CH₂— | H | O | O | —CH₂— | 4-methylphenyl | |
| 612 | CF₃ | H | CH₃ | H | CH₃ | O | —CH₂CH₂— | —CH₂— | H | O | O | —CH₂— | 4-methoxyphenyl | |
| 613 | CF₃ | H | CH₃ | H | CH₃ | O | —CH₂CH₂— | —CH₂— | H | O | O | —CH₂— | 2,4-dichlorophenyl | |
| 614 | CF₃ | H | CH₃ | H | CH₃ | O | —CH₂CH₂— | —CH₂— | H | O | O | —CH₂— | 3,5-dichlorophenyl | |
| 615 | CF₃ | H | CH₃ | H | CH₃ | O | —CH₂CH₂— | —CH₂— | H | O | O | —CH₂— | 2,6-dichlorophenyl | |
| 616 | CF₃ | H | CH₃ | H | CH₃ | O | —CH₂CH₂— | —CH₂— | H | O | O | —CH₂— | 2-chlorophenyl | |
| 617 | CF₃ | H | CH₃ | H | CH₃ | O | —CH₂CH₂— | —CH₂— | H | O | O | —CH₂— | 3-chlorophenyl | |
| 618 | CF₃ | H | CH₃ | H | CH₃ | O | —CH₂CH₂— | —CH₂— | H | O | O | —CH₂— | 3-(trifluoromethyl)phenyl | |
| 619 | CF₃ | H | CH₃ | H | CH₃ | O | —CH₂CH₂— | —CH₂— | H | O | O | —CH₂— | 3-methylphenyl | |
| 620 | CF₃ | H | CH₃ | H | CH₃ | O | —CH₂CH₂— | —CH₂— | H | O | O | —CH₂— | 2-methylphenyl | |
| 621 | CF₃ | H | CH₃ | H | CH₃ | O | —CH₂CH₂— | —CH₂— | H | O | O | —CH₂— | 4-nitrophenyl | |
| 622 | CF₃ | H | CH₃ | H | CH₃ | O | —CH₂CH₂— | —CH₂— | H | O | O | —CH₂— | 4-tert-butylphenyl | |
| 623 | CF₃ | H | CH₃ | H | CH₃ | O | —CH₂CH₂— | —CH₂— | H | O | S | —CH₂— | phenyl | |
| 624 | CF₃ | H | CH₃ | H | CH₃ | O | —CH₂CH₂— | —CH₂— | H | O | S | —CH₂— | 4-fluorophenyl | |
| 625 | CF₃ | H | CH₃ | H | CH₃ | O | —CH₂CH₂— | —CH₂— | H | O | S | —CH₂— | 4-chlorophenyl | |
| 626 | CF₃ | H | CH₃ | H | CH₃ | O | —CH₂CH₂— | —CH₂— | H | O | S | —CH₂— | 4-methylphenyl | |
| 627 | CF₃ | H | CH₃ | H | CH₃ | O | —CH₂CH₂— | —CH₂— | H | O | S | —CH₂— | 4-methoxyphenyl | |
| 628 | CF₃ | H | CH₃ | H | CH₃ | O | —CH₂CH₂— | —CH₂— | H | O | S | —CH₂— | 2,4-dichlorophenyl | |
| 629 | CF₃ | H | CH₃ | H | CH₃ | O | —CH₂CH₂— | —CH₂— | H | O | S | —CH₂— | 3,5-dichlorophenyl | |
| 630 | CF₃ | H | CH₃ | H | CH₃ | O | —CH₂CH₂— | —CH₂— | H | O | S | —CH₂— | 2,6-dichlorophenyl | |
| 631 | CF₃ | H | CH₃ | H | CH₃ | O | —CH₂CH₂— | —CH₂— | H | O | S | —CH₂— | 2-chlorophenyl | |
| 632 | CF₃ | H | CH₃ | H | CH₃ | O | —CH₂CH₂— | —CH₂— | H | O | S | —CH₂— | 3-chlorophenyl | |
| 633 | CF₃ | H | CH₃ | H | CH₃ | O | —CH₂CH₂— | —CH₂— | H | O | S | —CH₂— | 3-(trifluoromethyl)phenyl | |
| 634 | CF₃ | H | CH₃ | H | CH₃ | O | —CH₂CH₂— | —CH₂— | H | O | S | —CH₂— | 3-methylphenyl | |
| 635 | CF₃ | H | CH₃ | H | CH₃ | O | —CH₂CH₂— | —CH₂— | H | O | S | —CH₂— | 2-methylphenyl | |
| 636 | CF₃ | H | CH₃ | H | CH₃ | O | —CH₂CH₂— | —CH₂— | H | O | S | —CH₂— | 4-nitrophenyl | |
| 637 | CF₃ | H | CH₃ | H | CH₃ | O | —CH₂CH₂— | —CH₂— | H | O | S | —CH₂— | 4-tert-butylphenyl | |
| 638 | CF₃ | H | CH₃ | H | CH₃ | O | —CH₂CH₂— | —CH₂— | H | O | O | —CH(CH₃)— | 4-fluorophenyl | |
| 639 | CF₃ | H | CH₃ | H | CH₃ | O | —CH₂CH₂— | —CH₂— | H | O | O | —CH(CH₂CH₂)— | 4-fluorophenyl | |
| 640 | CF₃ | H | CH₃ | H | CH₃ | O | —CH₂CH₂— | —CH₂— | H | O | O | —CH₂CH₂— | 4-fluorophenyl | |
| 641 | CF₃ | H | CH₃ | H | CH₃ | O | —CH₂CH₂— | —CH₂— | H | O | O | bond | phenyl | |
| 642 | CF₃ | H | CH₃ | H | CH₃ | O | —CH₂CH₂— | —CH₂— | H | O | O | bond | 4-fluorophenyl | |
| 643 | CF₃ | H | CH₃ | H | CH₃ | O | —CH₂CH₂— | —CH₂— | H | O | O | bond | 4-chlorophenyl | |
| 644 | CF₃ | H | CH₃ | H | CH₃ | O | —CH₂CH₂— | —CH₂— | H | O | O | bond | 4-methylphenyl | |
| 645 | CF₃ | H | CH₃ | H | CH₃ | O | —CH₂CH₂— | —CH₂— | H | O | O | bond | 3-chlorophenyl | |
| 646 | CF₃ | H | CH₃ | H | CH₃ | O | —CH₂CH₂— | —CH₂— | H | O | O | bond | 3,5-dichlorophenyl | |
| 647 | CF₃ | H | CH₃ | H | CH₃ | O | —CH₂CH₂— | —CH₂— | H | O | O | bond | 3,4-dichlorophenyl | |
| 648 | CF₃ | H | CH₃ | H | CH₃ | O | —CH₂CH₂— | —CH₂— | H | O | O | bond | 2,4-dichlorophenyl | |

-continued

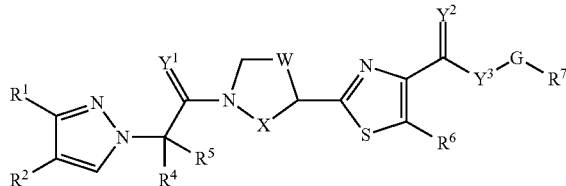
(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 649 | CF₃ | H | CH₃ | H | CH₃ | O | —CH₂CH₂— | —CH₂— | H | O | O | bond | 2-chlorophenyl | |
| 650 | CF₃ | H | CH₃ | H | CH₃ | O | —CH₂CH₂— | —CH₂— | H | O | O | bond | 2,6-dichlorophenyl | |
| 651 | CF₃ | H | CH₃ | H | CH₃ | O | —CH₂CH₂— | —CH₂— | H | O | O | bond | 3-(trifluorophenyl) | |
| 652 | CF₃ | H | CH₃ | H | CH₃ | O | —CH₂CH₂— | —CH₂— | H | O | O | bond | 3-methylphenyl | |
| 653 | CF₃ | H | CH₃ | H | CH₃ | O | —CH₂CH₂— | —CH₂— | H | O | O | bond | 2-methylphenyl | |
| 654 | CF₃ | H | CH₃ | H | CH₃ | O | —CH₂CH₂— | —CH₂— | H | O | O | bond | 4-tert-butylphenyl | |
| 655 | CF₃ | H | CH₃ | H | CH₃ | O | —CH₂CH₂— | —CH₂— | H | O | O | bond | 4-nitrophenyl | |
| 656 | CF₃ | H | CH₃ | H | CH₃ | O | —CH₂CH₂— | —CH₂— | H | O | S | bond | phenyl | |
| 657 | CF₃ | H | CH₃ | H | CH₃ | O | —CH₂CH₂— | —CH₂— | H | O | S | bond | 4-fluorophenyl | |
| 658 | CF₃ | H | CH₃ | H | CH₃ | O | —CH₂CH₂— | —CH₂— | H | O | S | bond | 4-chlorophenyl | |
| 659 | CF₃ | H | CH₃ | H | CH₃ | O | —CH₂CH₂— | —CH₂— | H | O | S | bond | 4-methylphenyl | |
| 660 | CF₃ | H | CH₃ | H | CH₃ | O | —CH₂CH₂— | —CH₂— | H | O | S | bond | 3-chlorophenyl | |
| 661 | CF₃ | H | CH₃ | H | CH₃ | O | —CH₂CH₂— | —CH₂— | H | O | S | bond | 3,5-dichlorophenyl | |
| 662 | CF₃ | H | CH₃ | H | CH₃ | O | —CH₂CH₂— | —CH₂— | H | O | S | bond | 3,4-dichlorophenyl | |
| 663 | CF₃ | H | CH₃ | H | CH₃ | O | —CH₂CH₂— | —CH₂— | H | O | S | bond | 2,4-dichlorophenyl | |
| 664 | CF₃ | H | CH₃ | H | CH₃ | O | —CH₂CH₂— | —CH₂— | H | O | S | bond | 2-chlorophenyl | |
| 665 | CF₃ | H | CH₃ | H | CH₃ | O | —CH₂CH₂— | —CH₂— | H | O | S | bond | 2,6-dichlorophenyl | |
| 666 | CF₃ | H | CH₃ | H | CH₃ | O | —CH₂CH₂— | —CH₂— | H | O | S | bond | 3-(trifluoromethyl)phenyl | |
| 667 | CF₃ | H | CH₃ | H | CH₃ | O | —CH₂CH₂— | —CH₂— | H | O | S | bond | 3-methylphenyl | |
| 668 | CF₃ | H | CH₃ | H | CH₃ | O | —CH₂CH₂— | —CH₂— | H | O | S | bond | 2-methylphenyl | |
| 669 | CF₃ | H | CH₃ | H | CH₃ | O | —CH₂CH₂— | —CH₂— | H | O | S | bond | 4-tert-butylphenyl | |
| 670 | CF₃ | H | CH₃ | H | CH₃ | O | —CH₂CH₂— | —CH₂— | H | O | S | bond | 4-nitrophenyl | |
| 671 | CF₃ | H | CH₃ | H | CH₃ | O | —CH₂CH₂— | —CH₂— | H | O | O | —CH₂— | pyridin-4-yl | |
| 672 | CF₃ | H | CH₃ | H | CH₃ | O | —CH₂CH₂— | —CH₂— | H | O | O | —CH₂— | 2-thienyl | |
| 673 | CF₃ | H | CH₃ | H | CH₃ | O | —CH₂CH₂— | —CH₂— | H | O | S | bond | cyclohexyl | |
| 674 | CF₃ | H | CH₃ | H | CH₃ | O | —CH₂CH₂— | —CH₂— | H | O | S | bond | 1-naphthyl | |
| 675 | (1Z,3Z)-buta-1,3-diene-1,4-diyl | | CH₃ | H | H | O | —CH₂CH₂— | —CH₂— | H | O | O | —CH₂— | trimethylsilyl | |
| 676 | (1Z,3Z)-buta-1,3-diene-1,4-diyl | | CH₃ | H | H | O | —CH₂CH₂— | —CH₂— | H | O | O | bond | cyclohexyl | |
| 677 | (1Z,3Z)-buta-1,3-diene-1,4-diyl | | CH₃ | H | H | O | —CH₂CH₂— | —CH₂— | H | O | O | bond | cyclopentyl | |
| 678 | (1Z,3Z)-buta-1,3-diene-1,4-diyl | | CH₃ | H | H | O | —CH₂CH₂— | —CH₂— | H | O | O | —CH₂— | cyclopropyl | |
| 679 | (1Z,3Z)-buta-1,3-diene-1,4-diyl | | CH₃ | H | H | O | —CH₂CH₂— | —CH₂— | H | O | O | —CH₂— | 2-dichloropropyl | |
| 680 | (1Z,3Z)-buta-1,3-diene-1,4-diyl | | CH₃ | H | H | O | —CH₂CH₂— | —CH₂— | H | O | O | bond | 1,2,3,4-tetrahydronaphthalen-1-yl | |
| 681 | (1Z,3Z)-buta-1,3-diene-1,4-diyl | | CH₃ | H | H | O | —CH₂CH₂— | —CH₂— | H | O | O | bond | decahydronaphthalen-1-yl | |
| 682 | (1Z,3Z)-buta-1,3-diene-1,4-diyl | | CH₃ | H | H | O | —CH₂CH₂— | —CH₂— | H | O | O | bond | 2,3-dihydro-1H-inden-1-yl | |
| 683 | (1Z,3Z)-buta-1,3-diene-1,4-diyl | | CH₃ | H | H | O | —CH₂CH₂— | —CH₂— | H | O | O | bond | 1-naphthyl | |
| 684 | (1Z,3Z)-buta-1,3-diene-1,4-diyl | | CH₃ | H | H | O | —CH₂CH₂— | —CH₂— | H | O | O | bond | 2-naphthyl | |

-continued (I)

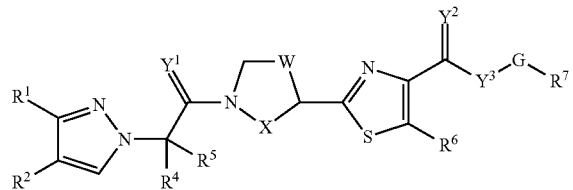

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 685 | (1Z,3Z)-buta-1,3-diene-1,4-diyl | | $CH_3$ | H | H | O | —$CH_2CH_2$— | —$CH_2$— | H | O | O | —$CH_2$— | phenyl | |
| 686 | (1Z,3Z)-buta-1,3-diene-1,4-diyl | | $CH_3$ | H | H | O | —$CH_2CH_2$— | —$CH_2$— | H | O | O | —$CH_2$— | 4-fluorophenyl | |
| 687 | (1Z,3Z)-buta-1,3-diene-1,4-diyl | | $CH_3$ | H | H | O | —$CH_2CH_2$— | —$CH_2$— | H | O | O | —$CH_2$— | 4-chlorophenyl | |
| 688 | (1Z,3Z)-buta-1,3-diene-1,4-diyl | | $CH_3$ | H | H | O | —$CH_2CH_2$— | —$CH_2$— | H | O | O | —$CH_2$— | 4-methylphenyl | |
| 689 | (1Z,3Z)-buta-1,3-diene-1,4-diyl | | $CH_3$ | H | H | O | —$CH_2CH_2$— | —$CH_2$— | H | O | O | —$CH_2$— | 4-methoxyphenyl | |
| 690 | (1Z,3Z)-buta-1,3-diene-1,4-diyl | | $CH_3$ | H | H | O | —$CH_2CH_2$— | —$CH_2$— | H | O | O | —$CH_2$— | 2,4-dichlorophenyl | |
| 691 | (1Z,3Z)-buta-1,3-diene-1,4-diyl | | $CH_3$ | H | H | O | —$CH_2CH_2$— | —$CH_2$— | H | O | O | —$CH_2$— | 3,5-dichlorophenyl | |
| 692 | (1Z,3Z)-buta-1,3-diene-1,4-diyl | | $CH_3$ | H | H | O | —$CH_2CH_2$— | —$CH_2$— | H | O | O | —$CH_2$— | 2,6-dichlorophenyl | |
| 693 | (1Z,3Z)-buta-1,3-diene-1,4-diyl | | $CH_3$ | H | H | O | —$CH_2CH_2$— | —$CH_2$— | H | O | O | —$CH_2$— | 2-chlorophenyl | |
| 694 | (1Z,3Z)-buta-1,3-diene-1,4-diyl | | $CH_3$ | H | H | O | —$CH_2CH_2$— | —$CH_2$— | H | O | O | —$CH_2$— | 3-chlorophenyl | |
| 695 | (1Z,3Z)-buta-1,3-diene-1,4-diyl | | $CH_3$ | H | H | O | —$CH_2CH_2$— | —$CH_2$— | H | O | O | —$CH_2$— | 3-(trifluoromethyl)phenyl | |
| 696 | (1Z,3Z)-buta-1,3-diene-1,4-diyl | | $CH_3$ | H | H | O | —$CH_2CH_2$— | —$CH_2$— | H | O | O | —$CH_2$— | 3-methylphenyl | |
| 697 | (1Z,3Z)-buta-1,3-diene-1,4-diyl | | $CH_3$ | H | H | O | —$CH_2CH_2$— | —$CH_2$— | H | O | O | —$CH_2$— | 2-methylphenyl | |
| 698 | (1Z,3Z)-buta-1,3-diene-1,4-diyl | | $CH_3$ | H | H | O | —$CH_2CH_2$— | —$CH_2$— | H | O | O | —$CH_2$— | 4-nitrophenyl | |
| 699 | (1Z,3Z)-buta-1,3-diene-1,4-diyl | | $CH_3$ | H | H | O | —$CH_2CH_2$— | —$CH_2$— | H | O | O | —$CH_2$— | 4-tert-butylphenyl | |
| 700 | (1Z,3Z)-buta-1,3-diene-1,4-diyl | | $CH_3$ | H | H | O | —$CH_2CH_2$— | —$CH_2$— | H | O | S | —$CH_2$— | phenyl | |
| 701 | (1Z,3Z)-buta-1,3-diene-1,4-diyl | | $CH_3$ | H | H | O | —$CH_2CH_2$— | —$CH_2$— | H | O | S | —$CH_2$— | 4-fluorophenyl | |
| 702 | (1Z,3Z)-buta-1,3-diene-1,4-diyl | | $CH_3$ | H | H | O | —$CH_2CH_2$— | —$CH_2$— | H | O | S | —$CH_2$— | 4-chlorophenyl | |
| 703 | (1Z,3Z)-buta-1,3-diene-1,4-diyl | | $CH_3$ | H | H | O | —$CH_2CH_2$— | —$CH_2$— | H | O | S | —$CH_2$— | 4-methylphenyl | |
| 704 | (1Z,3Z)-buta-1,3-diene-1,4-diyl | | $CH_3$ | H | H | O | —$CH_2CH_2$— | —$CH_2$— | H | O | S | —$CH_2$— | 4-methoxyphenyl | |
| 705 | (1Z,3Z)-buta-1,3-diene-1,4-diyl | | $CH_3$ | H | H | O | —$CH_2CH_2$— | —$CH_2$— | H | O | S | —$CH_2$— | 2,4-dichlorophenyl | |
| 706 | (1Z,3Z)-buta-1,3-diene-1,4-diyl | | $CH_3$ | H | H | O | —$CH_2CH_2$— | —$CH_2$— | H | O | S | —$CH_2$— | 3,5-dichlorophenyl | |

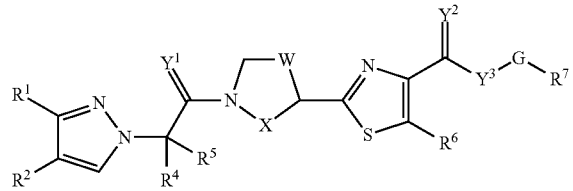

(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 707 | (1Z,3Z)-buta-1,3-diene-1,4-diyl | | CH₃ | H | H | O | —CH₂CH₂— | —CH₂— | H | O | S | —CH₂— | 2,6-dichlorophenyl | |
| 708 | (1Z,3Z)-buta-1,3-diene-1,4-diyl | | CH₃ | H | H | O | —CH₂CH₂— | —CH₂— | H | O | S | —CH₂— | 2-chlorophenyl | |
| 709 | (1Z,3Z)-buta-1,3-diene-1,4-diyl | | CH₃ | H | H | O | —CH₂CH₂— | —CH₂— | H | O | S | —CH₂— | 3-chlorophenyl | |
| 710 | (1Z,3Z)-buta-1,3-diene-1,4-diyl | | CH₃ | H | H | O | —CH₂CH₂— | —CH₂— | H | O | S | —CH₂— | 3-(trifluoromethyl)phenyl | |
| 711 | (1Z,3Z)-buta-1,3-diene-1,4-diyl | | CH₃ | H | H | O | —CH₂CH₂— | —CH₂— | H | O | S | —CH₂— | 3-methylphenyl | |
| 712 | (1Z,3Z)-buta-1,3-diene-1,4-diyl | | CH₃ | H | H | O | —CH₂CH₂— | —CH₂— | H | O | S | —CH₂— | 2-methylphenyl | |
| 713 | (1Z,3Z)-buta-1,3-diene-1,4-diyl | | CH₃ | H | H | O | —CH₂CH₂— | —CH₂— | H | O | S | —CH₂— | 4-nitrophenyl | |
| 714 | (1Z,3Z)-buta-1,3-diene-1,4-diyl | | CH₃ | H | H | O | —CH₂CH₂— | —CH₂— | H | O | S | —CH₂— | 4-tert-butylphenyl | |
| 715 | (1Z,3Z)-buta-1,3-diene-1,4-diyl | | CH₃ | H | H | O | —CH₂CH₂— | —CH₂— | H | O | O | —CH(CH₃)— | 4-fluorophenyl | |
| 716 | (1Z,3Z)-buta-1,3-diene-1,4-diyl | | CH₃ | H | H | O | —CH₂CH₂— | —CH₂— | H | O | O | —CH(CH₂CH₃)— | 4-fluorophenyl | |
| 717 | (1Z,3Z)-buta-1,3-diene-1,4-diyl | | CH₃ | H | H | O | —CH₂CH₂— | —CH₂— | H | O | O | —CH₂CH₂— | 4-fluorophenyl | |
| 718 | (1Z,3Z)-buta-1,3-diene-1,4-diyl | | CH₃ | H | H | O | —CH₂CH₂— | —CH₂— | H | O | O | bond | phenyl | |
| 719 | (1Z,3Z)-buta-1,3-diene-1,4-diyl | | CH₃ | H | H | O | —CH₂CH₂— | —CH₂— | H | O | O | bond | 4-fluorophenyl | |
| 720 | (1Z,3Z)-buta-1,3-diene-1,4-diyl | | CH₃ | H | H | O | —CH₂CH₂— | —CH₂— | H | O | O | bond | 4-chlorophenyl | |
| 721 | (1Z,3Z)-buta-1,3-diene-1,4-diyl | | CH₃ | H | H | O | —CH₂CH₂— | —CH₂— | H | O | O | bond | 4-methylphenyl | |
| 722 | (1Z,3Z)-buta-1,3-diene-1,4-diyl | | CH₃ | H | H | O | —CH₂CH₂— | —CH₂— | H | O | O | bond | 3-chlorophenyl | |
| 723 | (1Z,3Z)-buta-1,3-diene-1,4-diyl | | CH₃ | H | H | O | —CH₂CH₂— | —CH₂— | H | O | O | bond | 3,5-dichlorophenyl | |
| 724 | (1Z,3Z)-buta-1,3-diene-1,4-diyl | | CH₃ | H | H | O | —CH₂CH₂— | —CH₂— | H | O | O | bond | 3,4-dichlorophenyl | |
| 725 | (1Z,3Z)-buta-1,3-diene-1,4-diyl | | CH₃ | H | H | O | —CH₂CH₂— | —CH₂— | H | O | O | bond | 2,4-dichlorophenyl | |
| 726 | (1Z,3Z)-buta-1,3-diene-1,4-diyl | | CH₃ | H | H | O | —CH₂CH₂— | —CH₂— | H | O | O | bond | 2-chlorophenyl | |
| 727 | (1Z,3Z)-buta-1,3-diene-1,4-diyl | | CH₃ | H | H | O | —CH₂CH₂— | —CH₂— | H | O | O | bond | 2,6-dichlorophenyl | |
| 728 | (1Z,3Z)-buta-1,3-diene-1,4-diyl | | CH₃ | H | H | O | —CH₂CH₂— | —CH₂— | H | O | O | bond | 3-(trifluoromethyl)phenyl | |

-continued

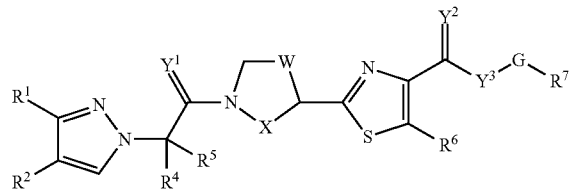
(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 729 | (1Z,3Z)-buta-1,3-diene-1,4-diyl | | CH₃ | H | H | O | —CH₂CH₂— | —CH₂— | H | O | O | bond | 3-methylphenyl | |
| 730 | (1Z,3Z)-buta-1,3-diene-1,4-diyl | | CH₃ | H | H | O | —CH₂CH₂— | —CH₂— | H | O | O | bond | 2-methylphenyl | |
| 731 | (1Z,3Z)-buta-1,3-diene-1,4-diyl | | CH₃ | H | H | O | —CH₂CH₂— | —CH₂— | H | O | O | bond | 4-tert-butyl-phenyl | |
| 732 | (1Z,3Z)-buta-1,3-diene-1,4-diyl | | CH₃ | H | H | O | —CH₂CH₂— | —CH₂— | H | O | O | bond | 4-nitrophenyl | |
| 733 | (1Z,3Z)-buta-1,3-diene-1,4-diyl | | CH₃ | H | H | O | —CH₂CH₂— | —CH₂— | H | O | S | bond | phenyl | |
| 734 | (1Z,3Z)-buta-1,3-diene-1,4-diyl | | CH₃ | H | H | O | —CH₂CH₂— | —CH₂— | H | O | S | bond | 4-fluorophenyl | |
| 735 | (1Z,3Z)-buta-1,3-diene-1,4-diyl | | CH₃ | H | H | O | —CH₂CH₂— | —CH₂— | H | O | S | bond | 4-chlorophenyl | |
| 736 | (1Z,3Z)-buta-1,3-diene-1,4-diyl | | CH₃ | H | H | O | —CH₂CH₂— | —CH₂— | H | O | S | bond | 4-methylphenyl | |
| 737 | (1Z,3Z)-buta-1,3-diene-1,4-diyl | | CH₃ | H | H | O | —CH₂CH₂— | —CH₂— | H | O | S | bond | 3-chlorophenyl | |
| 738 | (1Z,3Z)-buta-1,3-diene-1,4-diyl | | CH₃ | H | H | O | —CH₂CH₂— | —CH₂— | H | O | S | bond | 3,5-dichloro-phenyl | |
| 739 | (1Z,3Z)-buta-1,3-diene-1,4-diyl | | CH₃ | H | H | O | —CH₂CH₂— | —CH₂— | H | O | S | bond | 3,4-dichloro-phenyl | |
| 740 | (1Z,3Z)-buta-1,3-diene-1,4-diyl | | CH₃ | H | H | O | —CH₂CH₂— | —CH₂— | H | O | S | bond | 2,4-dichloro-phenyl | |
| 741 | (1Z,3Z)-buta-1,3-diene-1,4-diyl | | CH₃ | H | H | O | —CH₂CH₂— | —CH₂— | H | O | S | bond | 2-chlorophenyl | |
| 742 | (1Z,3Z)-buta-1,3-diene-1,4-diyl | | CH₃ | H | H | O | —CH₂CH₂— | —CH₂— | H | O | S | bond | 2,6-dichloro-phenyl | |
| 743 | (1Z,3Z)-buta-1,3-diene-1,4-diyl | | CH₃ | H | H | O | —CH₂CH₂— | —CH₂— | H | O | S | bond | 3-(trifluoro-methyl)phenyl | |
| 744 | (1Z,3Z)-buta-1,3-diene-1,4-diyl | | CH₃ | H | H | O | —CH₂CH₂— | —CH₂— | H | O | S | bond | 3-methylphenyl | |
| 745 | (1Z,3Z)-buta-1,3-diene-1,4-diyl | | CH₃ | H | H | O | —CH₂CH₂— | —CH₂— | H | O | S | bond | 2-methylphenyl | |
| 746 | (1Z,3Z)-buta-1,3-diene-1,4-diyl | | CH₃ | H | H | O | —CH₂CH₂— | —CH₂— | H | O | S | bond | 4-tert-butyl-phenyl | |
| 747 | (1Z,3Z)-buta-1,3-diene-1,4-diyl | | CH₃ | H | H | O | —CH₂CH₂— | —CH₂— | H | O | S | bond | 4-nitrophenyl | |
| 748 | (1Z,3Z)-buta-1,3-diene-1,4-diyl | | CH₃ | H | H | O | —CH₂CH₂— | —CH₂— | H | O | O | —CH₂— | pyridin-4-yl | |
| 749 | (1Z,3Z)-buta-1,3-diene-1,4-diyl | | CH₃ | H | H | O | —CH₂CH₂— | —CH₂— | H | O | O | —CH₂— | 2-thienyl | |
| 750 | (1Z,3Z)-buta-1,3-diene-1,4-diyl | | CH₃ | H | H | O | —CH₂CH₂— | —CH₂— | H | O | S | bond | cyclohexyl | |

-continued

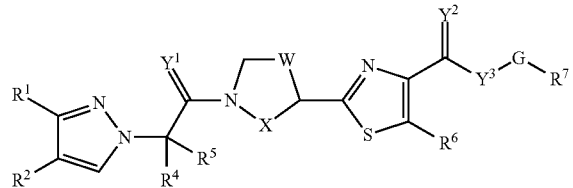

(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 751 | (1Z,3Z)-buta-1,3-diene-1,4-diyl | | CH₃ | H | H | O | —CH₂CH₂— | —CH₂— | H | O | S | bond | 1-naphthyl | |
| 752 | CF₃ | H | CH₃ | —CH₂CH₂— | | O | —CH₂CH₂— | —CH₂— | H | O | O | bond | cyclohexyl | |
| 753 | CF₃ | H | CH₃ | —CH₂CH₂— | | O | —CH₂CH₂— | —CH₂— | H | O | O | bond | 1,2,3,4-tetrahydro-naphthalen-1-yl | |
| 754 | CF₃ | H | CH₃ | —CH₂CH₂— | | O | —CH₂CH₂— | —CH₂— | H | O | O | bond | decahydro-naphthalen-1-yl | |
| 755 | CF₃ | H | CH₃ | —CH₂CH₂— | | O | —CH₂CH₂— | —CH₂— | H | O | O | bond | 2,3-dihydro-1H-inden-1-yl | |
| 756 | CF₃ | H | CH₃ | —CH₂CH₂— | | O | —CH₂CH₂— | —CH₂— | H | O | O | bond | 1-naphthyl | |
| 757 | CF₃ | H | CH₃ | —CH₂CH₂— | | O | —CH₂CH₂— | —CH₂— | H | O | O | bond | 2-naphthyl | |
| 758 | CF₃ | H | CH₃ | —CH₂CH₂— | | O | —CH₂CH₂— | —CH₂— | H | O | O | —CH₂— | phenyl | |
| 759 | CF₃ | H | CH₃ | H | cyclopropyl | O | —CH₂CH₂— | —CH₂— | H | O | O | bond | cyclohexyl | |
| 760 | CF₃ | H | CH₃ | H | cyclopropyl | O | —CH₂CH₂— | —CH₂— | H | O | O | bond | 1,2,3,4-tetrahydro-naphthalen-1-yl | |
| 761 | CF₃ | H | CH₃ | H | cyclopropyl | O | —CH₂CH₂— | —CH₂— | H | O | O | bond | decahydro-naphthalen-1-yl | |
| 762 | CF₃ | H | CH₃ | H | cyclopropyl | O | —CH₂CH₂— | —CH₂— | H | O | O | bond | 2,3-dihydro-1H-inden-1-yl | |
| 763 | CF₃ | H | CH₃ | H | cyclopropyl | O | —CH₂CH₂— | —CH₂— | H | O | O | bond | 1-naphthyl | |
| 764 | CF₃ | H | CH₃ | H | cyclopropyl | O | —CH₂CH₂— | —CH₂— | H | O | O | bond | 2-naphthyl | |
| 765 | CF₃ | H | CH₃ | H | cyclopropyl | O | —CH₂CH₂— | —CH₂— | H | O | O | —CH₂— | phenyl | |
| 766 | CF₃ | H | CH₃ | H | H | O | —CH₂CH₂— | —CH₂— | H | O | O | —CH₂CH₂— | tert-butyl | |
| 767 | CF₃ | H | H | H | H | O | —CH₂CH₂— | —CH₂— | H | O | O | bond | —CH₂CH₂— | 3.82* |
| 768 | CF₃ | chlorine | CH₃ | H | H | O | —CH₂CH₂— | —CH₂— | H | O | O | —CH₂CH₂— | tert-butyl | |
| 769 | CF₃ | chlorine | CH₃ | H | CH₃ | O | —CH₂CH₂— | —CH₂— | H | O | O | bond | cyclohexyl | 4.58* |
| 770 | CF₃ | chlorine | CH₃ | H | CH₃ | O | —CH₂CH₂— | —CH₂— | H | O | O | bond | 1-naphthyl | 4.50* |
| 771 | CF₃ | H | CF₃ | H | H | O | —CH₂CH₂— | —CH₂— | H | O | O | bond | 1-naphthyl | 4.35* |
| 772 | CF₃ | H | CF₃ | H | H | O | —CH₂CH₂— | —CH₂— | H | O | O | bond | cyclohexyl | 4.39* |
| 773 | CF₃ | H | H | H | CH₃ | O | —CH₂CH₂— | —CH₂— | H | O | O | bond | 1-naphthyl | 3.87* |
| 774 | CF₃ | H | H | H | CH₃ | O | —CH₂CH₂— | —CH₂— | H | O | O | bond | cyclohexyl | 3.88* |
| 775 | CF₃ | H | CH₃ | H | H | O | —CH₂CH₂— | —CH₂— | H | O | O | —CH₂— | 3,4-dichloro-phenyl | 4.09* |
| 776 | CF₃ | H | CH₃ | H | H | O | —CH₂CH₂— | —CH₂— | H | O | O | —CH₂— | 4-(trifluoromethyl)phenyl | 3.86* |
| 777 | CF₃ | H | phenyl | H | H | O | —CH₂CH₂— | —CH₂— | H | O | O | bond | 1-naphthyl | 4.50* |
| 778 | CF₃ | H | ethyl | H | H | O | —CH₂CH₂— | —CH₂— | H | O | O | bond | 1-naphthyl | |
| 779 | CF₃ | H | CH₃ | H | H | O | —CH₂CH₂— | —CH₂— | H | O | O | —CH₂— | (E)-2-phenylethenyl | 3.74* |
| 780 | CF₃ | H | CH₃ | H | H | O | —CH₂CH₂— | —CH₂— | H | O | O | —CH₂— | pyridin-3-yl | 1.74* |
| 781 | CF₃ | H | CH₃ | H | H | O | —CH₂CH₂— | —CH₂— | H | O | O | bond | quinolin-7-yl | 2.42* |
| 782 | CF₃ | H | CH₃ | H | H | O | —CH₂CH₂— | —CH₂— | H | O | O | bond | quinolin-8-yl | 2.88* |
| 783 | CF₃ | H | CH₃ | H | H | O | —CH₂CH₂— | —CH₂— | H | O | O | —CH₂— | 1-naphthyl | 3.90* |
| 784 | CF₃ | H | CH₃ | H | H | O | —CH₂CH₂— | —CH₂— | H | O | O | —CH₂— | 2-naphthyl | 3.92* |
| 785 | CF₃ | H | CH₃ | H | H | O | —CH₂CH₂— | —CH₂— | H | O | O | —CH(CH₃)— | 1-naphthyl | 4.16* |
| 786 | CF₃ | H | CH₃ | H | H | O | —CH₂CH₂— | —CH₂— | H | O | O | —CH(CH₃)— | 2-naphthyl | 4.18* |
| 787 | CF₃ | H | CH₃ | H | H | O | —CH₂CH₂— | —CH₂— | H | O | O | —CH₂— | phenylethynyl | 3.70* |
| 788 | CF₃ | H | CH₃ | H | H | O | —CH₂CH₂— | —CH₂— | H | O | O | bond | cycloheptyl | 4.09* |
| 789 | CF₃ | H | CH₃ | H | H | O | —CH₂CH₂— | —CH₂— | H | O | O | bond | 1,2,3,4-tetrahydro-naphthalen-2-yl | |
| 790 | CF₃ | H | CH₃ | H | H | O | —CH₂CH₂— | —CH₂— | H | O | O | bond | 5,6,7,8-tetrahydro-naphthalen-1-yl | 4.21* |
| 791 | CF₃ | H | CH₃ | H | H | O | —CH₂CH₂— | —CH₂— | H | O | O | bond | 2,3-dihydro-1H-inden-2-yl | 3.67* |

-continued

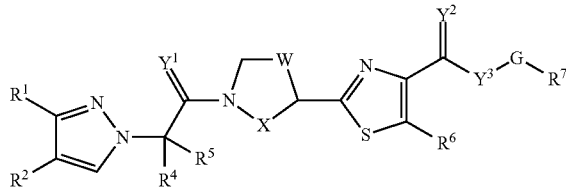

(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 792 | CF₃ | H | CH₃ | H | H | O | —CH₂CH₂— | —CH₂— | H | O | O | bond | 5,6,7,8-tetrahydro-naphthalen-1-yl | 4.30* |
| 793 | CF₃ | H | CH₃ | H | H | O | —CH₂CH₂— | —CH₂— | H | O | O | bond | quinolin-6-yl | 2.37* |
| 794 | CF₃ | H | CH₃ | H | H | O | —CH₂CH₂— | —CH₂— | H | O | O | bond | isoquinolin-5-yl | 2.18* |
| 795 | CF₃ | H | CH₃ | H | H | O | —CH₂CH₂— | —CH₂— | H | O | O | bond | (1R)-1,2,3,4-tetrahydro-naphthalen-1-yl | 4.06* |
| 796 | CH₃ | H | di-fluoro-methyl | H | H | O | —CH₂CH₂— | —CH₂— | H | O | O | bond | cyclohexyl | 3.28* |
| 797 | CH₃ | H | CH₃ | CH₃ | CH₃ | O | —CH₂CH₂— | —CH₂— | H | O | O | bond | 5-methyl-2-(propan-2-yl)cyclohexyl | 5.51* |
| 798 | CH₃ | H | CH₃ | CH₃ | CH₃ | O | —CH₂CH₂— | —CH₂— | H | O | O | bond | 1-ethynyl-cyclopentyl | 3.28* |
| 799 | CH₃ | H | CH₃ | CH₃ | CH₃ | O | —CH₂CH₂— | —CH₂— | H | O | O | —CH(CH₂CH₃)— | (1Z)-prop-1-en-1-yl | 3.78* |
| 800 | CH₃ | H | CH₃ | CH₃ | CH₃ | O | —CH₂CH₂— | —CH₂— | H | O | O | bond | (1S,2R)-1,7,7-trimethyl-bicyclo[2.2.1]hept-2-yl | 5.08* |
| 801 | CH₃ | H | CH₃ | CH₃ | CH₃ | O | —CH₂CH₂— | —CH₂— | H | O | O | bond | hex-1-en-3-yl | 3.78* |
| 802 | CH₃ | H | CH₃ | CH₃ | CH₃ | O | —CH₂CH₂— | —CH₂— | H | O | O | bond | 3-methyl-5-(propan-2-yl)cyclohexyl | 5.58* |
| 803 | CH₃ | H | CH₃ | CH₃ | CH₃ | O | —CH₂CH₂— | —CH₂— | H | O | O | —CH₂CH₂— | dimethylamino | 1.03* |
| 804 | CH₃ | H | CH₃ | CH₃ | CH₃ | O | —CH₂CH₂— | —CH₂— | H | O | O | bond | 1-ethynyl-cyclohexyl | 3.73* |
| 805 | CH₃ | H | CH₃ | CH₃ | CH₃ | O | —CH₂CH₂— | —CH₂— | H | O | O | —CH(CH₃)— | CF₃ | |
| 806 | CH₃ | H | CH₃ | CH₃ | CH₃ | O | —CH₂CH₂— | —CH₂— | H | O | O | —CH₂— | heptan-3-yl | 5.08* |
| 807 | CF₃ | H | CH₃ | H | H | O | —CH₂CH₂— | —CH₂— | H | O | O | bond | quinolin-5-yl | 2.59* |
| 808 | CF₃ | H | CH₃ | H | H | O | —CH₂CH₂— | —CH₂— | H | O | O | bond | diphenylmethyl | 4.17* |
| 809 | CF₃ | H | CH₃ | H | H | O | —CH₂CH₂— | —CH₂— | H | O | O | bond | 1,3-benzoxazol-4-yl | 2.81* |
| 810 | ethyl | H | ethyl | H | H | O | —CH₂CH₂— | —CH₂— | H | O | O | bond | cyclohexyl | |
| 811 | di-fluoro-methyl | H | di-fluoro-methyl | H | H | O | —CH₂CH₂— | —CH₂— | H | O | O | bond | cyclohexyl | 3.64* |
| 812 | ethyl | H | ethyl | H | H | O | —CH₂CH₂— | —CH₂— | H | O | O | bond | 1-naphthyl | |
| 813 | di-fluoro-methyl | H | di-fluoro-methyl | H | H | O | —CH₂CH₂— | —CH₂— | H | O | O | bond | 1-naphthyl | 3.64* |
| 814 | CF₃ | H | CH₃ | H | H | O | —CH₂CH₂— | —CH₂— | H | O | O | bond | 2-methoxy-phenyl | 3.17* |
| 815 | CF₃ | H | CH₃ | H | H | O | —CH₂CH₂— | —CH₂— | H | O | O | bond | cyclopropyl-(phenyl)methyl | 3.87* |
| 816 | CF₃ | H | CH₃ | H | H | O | —CH₂CH₂— | —CH₂— | H | O | O | bond | 2,6-dimethoxy-phenyl | 3.12* |
| 817 | CF₃ | H | CH₃ | H | H | O | —CH₂CH₂— | —CH₂— | H | O | O | —CH₂— | 2-methoxy-phenyl | 3.44* |
| 818 | CF₃ | H | CH₃ | H | H | O | —CH₂CH₂— | —CH₂— | H | O | O | —CH₂— | 2,4,6-trichloro-phenyl | 4.53* |
| 819 | CF₃ | H | CH₃ | H | H | O | —CH₂CH₂— | —CH₂— | H | O | O | —CH₂— | 4-(trifluoro-methoxy)phenyl | 3.99* |
| 820 | CF₃ | H | CH₃ | H | H | O | —CH₂CH₂— | —CH₂— | H | O | O | —CH₂— | 2-bromophenyl | 3.80* |
| 821 | CF₃ | H | CH₃ | H | H | O | —CH₂CH₂— | —CH₂— | H | O | O | bond | biphenyl-2-yl | 3.96* |
| 822 | CF₃ | H | CH₃ | H | H | O | —CH₂CH₂— | —CH₂— | H | O | O | bond | biphenyl-2-yl | 4.16* |
| 823 | CF₃ | H | CH₃ | H | H | O | —CH₂CH₂— | —CH₂— | H | O | O | bond | biphenyl-2-yl | 4.17* |
| 824 | CF₃ | H | CH₃ | H | H | O | —CH₂CH₂— | —CH₂— | H | O | O | bond | 3-phenoxy-phenyl | 4.18* |
| 825 | CF₃ | H | CH₃ | H | H | O | —CH₂CH₂— | —CH₂— | H | O | O | bond | 4-phenoxy-phenyl | 4.14* |
| 826 | CF₃ | H | CH₃ | H | H | O | —CH₂CH₂— | —CH₂— | H | O | O | bond | 1-ethynyl-cyclohexyl | 3.76* |

-continued

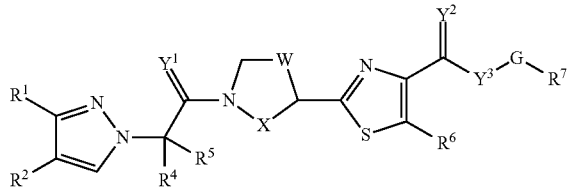

(I)

| EX NO | R¹ | R² | R³ | R⁴ | R⁵ | Y¹ | X | W | R⁶ | Y² | Y³ | G | R⁷ | log p |
|---|---|---|---|---|---|---|---|---|---|---|---|---|---|---|
| 827 | $CF_3$ | H | $CH_3$ | H | H | O | —$CH_2CH_2$— | —$CH_2$— | H | O | O | bond | 1-cyano-cyclohexyl | 3.33* |
| 828 | $CF_3$ | H | $CH_3$ | H | H | O | —$CH_2CH_2$— | —$CH_2$— | H | O | O | bond | 4-tert-butyl-cyclohexyl | 5.19* |
| 829 | $CF_3$ | H | $CH_3$ | H | H | O | —$CH_2CH_2$— | —$CH_2$— | H | O | O | bond | 5-methyl-2-(propan-2-yl)-cyclohexyl | 5.22* |
| 830 | $CF_3$ | H | $CH_3$ | H | H | O | —$CH_2CH_2$— | —$CH_2$— | H | O | O | bond | 1,4-dioxaspiro[4.5]dec-8-yl | 2.90* |
| 831 | $CF_3$ | H | $CH_3$ | H | H | O | —$CH_2CH_2$— | —$CH_2$— | H | O | O | bond | 2,6-dimethyl-cyclohexyl | 4.40* |
| 832 | $CF_3$ | H | $CH_3$ | H | H | O | —$CH_2CH_2$— | —$CH_2$— | H | O | O | bond | 2-methyl-cyclohexyl | 4.12* |
| 833 | $CF_3$ | H | $CH_3$ | H | H | O | —$CH_2CH_2$— | —$CH_2$— | H | O | O | bond | octyl | 5.02* |
| 834 | $CF_3$ | H | $CH_3$ | H | H | O | —$CH_2CH_2$— | —$CH_2$— | H | O | O | —$CH_2$— | 2,4-dimethoxy-phenyl | 3.33* |
| 835 | $CF_3$ | H | $CH_3$ | H | H | O | —$CH_2CH_2$— | —$CH_2$— | H | O | O | —$CH_2$— | 2,4,6-trifluoro phenyl | 3.53* |
| 836 | $CF_3$ | H | $CH_3$ | H | H | O | —$CH_2CH_2$— | —$CH_2$— | H | O | O | —$CH_2$— | 2-(trifluoro-methyl)phenyl | 3.84* |
| 837 | $CF_3$ | H | $CH_3$ | H | H | O | —$CH_2CH_2$— | —$CH_2$— | H | O | O | —$CH_2$— | 2-(trifluoro-methoxy)phenyl | 3.95* |
| 838 | $CF_3$ | H | $CH_3$ | H | H | O | —$CH_2CH_2$— | —$CH_2$— | H | O | O | —$CH_2$— | $CH_3$ | |
| 839 | H | $CF_3$ | $CH_3$ | H | H | O | —$CH_2CH_2$— | —$CH_2$— | H | O | O | —$CH_2$— | $CH_3$ | |
| 840 | $CF_3$ | H | H | H | H | O | —$CH_2CH_2$— | —$CH_2$— | H | O | O | —$CH_2$— | $CH_3$ | |
| 841 | $CF_3$ | chlorine | $CH_3$ | H | H | O | —$CH_2CH_2$— | —$CH_2$— | H | O | O | —$CH_2$— | $CH_3$ | |
| 842 | $CH_3$ | H | $CH_3$ | $CH_3$ | $CH_3$ | O | —$CH_2CH_2$— | —$CH_2$— | H | O | O | —$CH_2$— | $CH_3$ | |
| 843 | $CF_3$ | H | $CH_3$ | H | H | O | —$CH_2$— | —$CH_2CH_2$— | H | O | O | —$CH_2$— | $CH_3$ | |
| 844 | $CF_3$ | H | difluoromethyl | H | H | O | —$CH_2CH_2$— | —$CH_2$— | H | O | O | bond | 1-naphthyl | |
| 845 | $CF_3$ | H | $CH_3$ | H | H | O | —$CH_2CH_2$— | —$CH_2$— | H | O | O | —$CH_2$— | 2-[1-methoxy-2-(methyl amino)-2-oxo-ethyl]phenyl | |
| 846 | $CF_3$ | H | $CH_3$ | H | H | O | —$CH_2CH_2$— | —$CH_2$— | H | O | O | —$CH_2$— | 2-[(methyl-amino)-(oxo)acetyl]phenyl | |
| 847 | tBu | H | $CF_3$ | H | H | O | —$CH_2CH_2$— | —$CH_2$— | H | O | O | —$CH_2$— | cyclohexyl | 4.75* |
| 848 | $CF_3$ | H | tBu | H | H | O | —$CH_2CH_2$— | —$CH_2$— | H | O | O | —$CH_2$— | cyclohexyl | 4.51* |
| 849 | tBu | H | $CF_2CF_3$ | H | H | O | —$CH_2CH_2$— | —$CH_2$— | H | O | O | —$CH_2$— | cyclohexyl | 5.08* |
| 850 | $CF_2CF_3$ | H | tBu | H | H | O | —$CH_2CH_2$— | —$CH_2$— | H | O | O | —$CH_2$— | cyclohexyl | 4.94* |
| 851 | iPr | H | $CF_3$ | H | H | O | —$CH_2CH_2$— | —$CH_2$— | H | O | O | —$CH_2$— | cyclohexyl | 4.35* |
| 852 | ethyl | H | $CF_3$ | H | H | O | —$CH_2CH_2$— | —$CH_2$— | H | O | O | —$CH_2$— | cyclohexyl | 3.99* |
| 853 | $CF_3$ | H | $CH_3$ | H | H | O | —$CH_2CH_2$— | —$CH_2$— | H | O | O | bond | (1S)-1,2,3,4-tetrahydro-naphthalen-1-yl | 4.06* |
| 854 | difluoromethyl | H | difluoromethyl | H | H | S | —$CH_2CH_2$— | —$CH_2$— | H | O | O | bond | cyclohexyl | 4.23* |

The logP values were measured according to EEC directive 79/831 Annex V.A8 by HPLC (High Performance Liquid Chromatography) or reversed-phase columns (C 18), using the methods below:

**The determination in the acidic range is carried out at pH 2.3 using the mobile phases 0.1% aqueous phosphoric acid and acetonitrile linear gradient from 10% acetonitrile to 95% acetonitrile.

*The LC-MS determination in the acidic range is carried out at pH 2.7 using the mobile phases 0.1% aqueous formic acid and acetonitrile (contains 0.1% formic acid) linear gradient from 10% acetonitrile to 95% acetonitrile

***The LC-MS determination in the neutral range is carried out at pH 7.8 using the mobile phases 0.001 molar ammonium bicarbonate solution and acetonitrile linear gradient from 10% acetonitrile to 95% acetonitrile.

The calibration is carried out using unbranched alkan-2-ones (having 3 to 16 carbon atoms) with known log P values (determination of the log P values by the retention times using linear interpolation between two successive alkanones). The lambda-maX values were determined in the maxima of the chromatographic signals using the UV spectra from 200 nm to 400 nm.

USE EXAMPLES

Example A

*Phytophthora* Test (Tomato)/Protective

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Phytophthora infestans*. The plants are then placed in an incubation cabin at about 20° C. and 100% relative atmospheric humidity.

Evaluation is carried out 3 days after the inoculation. 0% means an efficacy which corresponds to that of the control, whereas an efficacy of 100% means that no infection is observed.

In this test, the compounds according to the invention of the formulae below show, at an active compound concentration of 100 ppm, an efficacy of 70% or more.

Ex. Nos. 44, 45, 8, 10, 766, 772, 771, 774, 773, 18, 20, 19, 775, 17, 23, 24, 776, 29, 21, 26, 28, 15, 31, 25, 778, 81, 3, 779, 781, 782, 783, 784, 785, 788, 790, 789, 791, 792, 795, 794, 796, 811, 813

Example B

*Plasmopara* Test (Grapevine)/Protective

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at about 20° C. and 100% relative atmospheric humidity for 1 day. The plants are then placed in a greenhouse at about 21° C. and about 90% atmospheric humidity for 4 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, the compounds according to the invention of the formulae below show, at an active compound concentration of 100 ppm, an efficacy of 70% or more.

Ex. Nos. 44, 45, 8, 10, 766, 772, 771, 774, 773, 18, 20, 19, 775, 17, 23, 24, 776, 21, 26, 28, 15, 31, 25, 778, 81, 3, 779, 781, 782, 783, 784, 785, 788, 790, 789, 791, 792, 795, 794, 796, 811, 813

Example C

*Phytophthora* Test (Tomato)/Protective

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Phytophthora infestans*. The plants are then placed in an incubation cabin at about 20° C. and 100% relative atmospheric humidity.

Evaluation is carried out 3 days after the inoculation. 0% means an efficacy which corresponds to that of the control, whereas an efficacy of 100% means that no infection is observed.

TABLE

*Phytophthora* test (tomato)/protective

| Active compound Known from WO2007014290 | Active compound application rate in ppm | Efficacy in % |
|---|---|---|
| [structure] | 10 | 65 |

According to the invention:

TABLE-continued

Phytophthora test (tomato)/protective

| Active compound<br>Known from WO2007014290 | Active compound application rate in ppm | Efficacy in % |
|---|---|---|
| Ex. 23 | 10 | 94 |

Example D

*Plasmopara* Test (Grapevine)/Protective

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at about 20° C. and 100% relative atmospheric humidity for 1 day. The plants are then placed in a greenhouse at about 21° C. and about 90% atmospheric humidity for 4 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

TABLE

*Plasmopara* test (grapevine)/protective

| Active compound<br>Known from WO2007014290 | Active compound application rate in ppm | Efficacy in % |
|---|---|---|
|  | 1 | 72 |

According to the invention:

| | 1 | 91 |
|---|---|---|
| Ex. 6 | | |

Example E

*Plasmopara* Test (Grapevine)/Curative

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous spore suspension of *Plasmopara viticola*. The plants remain in an incubation cabin at about 20° C. and 100% relative atmospheric humidity for 24 hours, and after a further 24 hours at about 21° C. and about 90% relative atmospheric humidity, the plants are sprayed with the active compound preparation at the stated application rate.

5 days after the inoculation, the plants are moistened and placed in an incubation cabin for 1 day.

Evaluation is carried out 6 days after the inoculation. 0% means an efficacy which corresponds to that of the control, whereas an efficacy of 100% means that no infection is observed.

TABLE

*Plasmopara* test (grapevine)/curative

| Active compound<br>Known from WO2007014290 | Active compound<br>application<br>rate in ppm | Efficacy<br>in % |
|---|---|---|
| 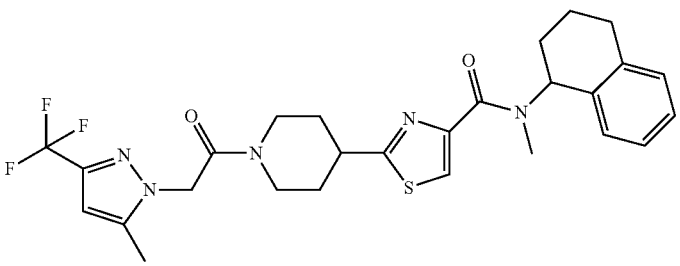 [SMILES: Cc1cc(C(F)(F)F)nn1CC(=O)N1CCC(c2nc(C(=O)N(C)C3CCCc4ccccc43)cs2)CC1] | 100 | 37 |
| According to the invention:<br>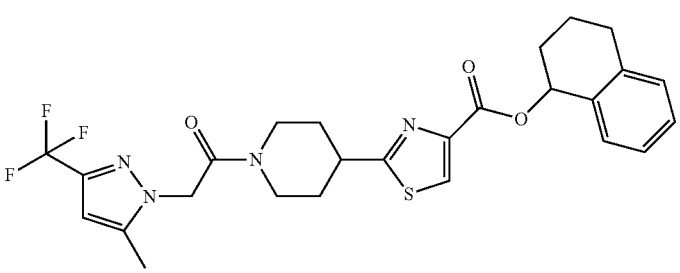 [SMILES: Cc1cc(C(F)(F)F)nn1CC(=O)N1CCC(c2nc(C(=O)OC3CCCc4ccccc43)cs2)CC1]<br>Ex. 6 | 100 | 84 |

The invention claimed is:
1. A compound of the formula (I)

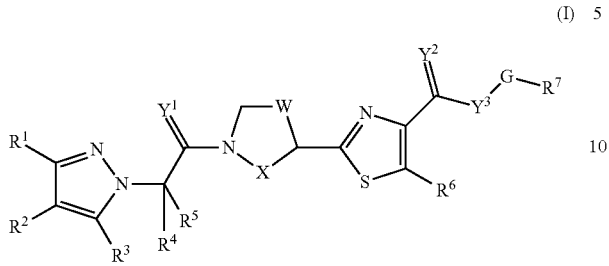

in which the symbols have the following meanings:
R¹ and R³ independently of one another are H, $C_1$-$C_4$-alkyl, $C_2$-$C_4$-alkenyl, $C_2$-$C_4$-alkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-haloalkoxy, halogen, hydroxyl, cyano or phenyl,
R² is H, phenyl, $C_1$-$C_4$-alkyl, $C_2$-$C_4$-alkenyl, $C_2$-$C_4$-alkynyl, $C_3$-$C_6$-cycloalkyl, $C_3$-$C_6$-halocycloalkyl, $C_1$-$C_4$-alkoxy, $C_1$-$C_4$-haloalkyl, $C_1$-$C_4$-haloalkoxy, formyl, $CR^8$=$NOR^9$, halogen, hydroxyl, cyano or $NR^{10}R^{11}$,
or
R¹ and R² or R² and R³ together with the carbon atoms to which they are attached form a 5- to 7-membered unsubstituted or substituted, partially saturated or unsaturated cycle which may contain up to two further heteroatoms selected from the group consisting of N, O and S, where two oxygen atoms are not adjacent,
possible substituents independently of one another being selected from the group consisting of $C_1$-$C_4$-alkyl, hydroxyl, oxo and halogen,
R⁴ and R⁵ independently of one another are H, $C_1$-$C_4$-alkyl, $C_3$-$C_6$-cycloalkyl or
or
R⁴ and R⁵ together with the carbon atom to which they are attached form a 3- to 6-membered saturated cycle which may contain up to two heteroatoms selected from the group consisting of N and O, where two oxygen atoms are not adjacent,
Y¹, and Y² are oxygen,
Y³ is sulfur or oxygen,
X is a direct bond or an unsubstituted or substituted $C_1$- to $C_3$-carbon chain, where the carbon atoms carry, independently of one another, H, methyl or oxo as substituents,
W is an unsubstituted or substituted $C_1$- to $C_3$-carbon chain, where the carbon atoms carry, independently of one another, H, methyl or oxo as substituents,
R⁶ is H, $C_1$-$C_4$-alkyl, $C_1$-$C_4$-haloalkyl, $CONR^{10}R^{11}$, ($C_1$-$C_4$-alkoxy)carbonyl, COOH, $NR^{10}R^{11}$, halogen or cyano,
G is $(C(R^{12})_2)_m$,
where m=0 to 6,
R⁷ is unsubstituted or substituted $C_5$-$C_{10}$-alkyl, $C_2$-$C_{16}$-alkenyl, $C_2$-$C_{16}$-alkynyl, $C_3$-$C_{15}$-cycloalkyl, $C_5$-$C_{15}$-cycloalkenyl, $C_3$-$C_{15}$-heterocyclyl, aryl, hetaryl or Si($C_1$-$C_4$-alkyl)₃,
possible substituents independently of one another are selected from:
halogen, cyano, nitro, nitroso, $C_1$-$C_4$-alkyl, $C_1$-$C_4$-haloalkyl, aryl-$C_1$-$C_3$-alkyl, aryl-$C_1$-$C_3$-haloalkyl, hydroxyl, oxo, $C_1$-$C_4$-alkoxy, $O(C_1$-$C_6$-alkyl)$_m$$OC_1$-$C_6$-alkyl, O—$C_3$-$C_6$-cycloalkyl, O-phenyl, $C_1$-$C_4$-haloalkoxy, SH, $C_1$-$C_4$-thioalkyl, $C_1$-$C_4$-thiohaloalkyl, S-phenyl, $SO_2$—$C_1$-$C_6$-alkyl, $SO_2$—$C_1$-$C_6$-haloalkyl, SO—$C_1$-$C_6$-alkyl, SO—$C_1$-$C_6$-haloalkyl, $CO_2H$, ($C_1$-$C_4$-alkyl)carbonyl, ($C_1$-$C_4$-haloalkyl)carbonyl, formyl, $CR^8$=$NOR^9$, $CONR^{10}R^{11}$, ($C_1$-$C_4$-alkoxy)carbonyl, COOH, $NR^{10}R^{11}$, cyclopropylamino, $CH_2COCH_3$, $(CH_2)_mO$—$C_1$-$C_6$-alkyl, $CH_2OH$, $CH_2SMe$, $(CH_2)_2SMe$, $C_3$-$C_6$-cycloalkyl, 1-methoxycyclopropyl, 1-chlorocyclopropyl, cyclohexylmethyl, $C_2$-$C_6$-alkenyl, $C_2$-$C_6$-alkynyl, Si($C_1$-$C_4$-alkyl)₃, phenyl or benzyl,
or
two adjacent substituents form an optionally methyl- or halogen-substituted dioxolane or dioxane ring,
R⁸, R⁹, R¹⁰, and R¹¹ independently of one another are H, $C_1$-$C_3$-alkyl or cyclopropyl,
or
R¹⁰ and R¹¹ together with the nitrogen atom to which they are attached form a 3- to 6-membered saturated cycle which may contain up to one further heteroatom selected from the group consisting of N and O,
R¹² is identical or different independently of one another H, chlorine, fluorine, $C_1$-$C_3$-alkyl, $C_1$-$C_3$-alkoxy, $C_3$-$C_6$-cycloalkyl or trifluoromethyl,
or
two or four R¹², in each case on two adjacent carbon atoms, are direct bonds,
or an agrochemically active salt thereof.
2. The compound of the formula (I) as claimed in claim 1, in which one or more of the symbols have one of the following meanings:
R¹ is methyl, ethyl, 1-methylethyl, 1,1-dimethylethyl, difluoromethyl, trifluoromethyl or pentafluoroethyl,
R² is H or chlorine,
R³ is H, methyl, 1,1-dimethylethyl, difluoromethyl, trifluoromethyl, pentafluoroethyl or phenyl,
R⁴ is H or methyl,
R⁵ is H or methyl,
Y¹ is oxygen,
Y² is oxygen,
Y³ is sulfur or oxygen,
X is $CH_2$ or $CH_2CH_2$,
W is $CH_2$ or $CH_2CH_2$,
R⁶ is H,
G is a direct bond, $CH_2$, $CH_2CH_2$, $CH(CH_3)$ or $CH_2(CH_2CH_3)$,
R⁷ is heptan-3-yl, octyl, (1Z)-prop-1-en-1-yl, (E)-2-phenylethenyl, hex-1-en-3-yl, diphenylmethyl, 1,2,3,4-tetrahydronaphthalen-1-yl, (1R)-1,2,3,4-tetrahydronaphthalen-1-yl, (1S)-1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decahydronaphthalen-1-yl, 1,4-dioxaspiro[4.5]dec-8-yl, 2,3-dihydro-1H-inden-1-yl, 2,3-dihydro-1H-inden-2-yl, cyclopropyl, cyclopentyl, 1-ethynylcyclopentyl, cyclohexyl, 2-methylcyclohexyl, 2,6-dimethylcyclohexyl, 4-tert-butylcyclohexyl, 5-methyl-2-(propan-2-yl)cyclohexyl, 3-methyl-5-(propan-2-yl)cyclohexyl, 1-cyanocyclohexyl, 1-ethynylcyclohexyl, cycloheptyl, cyclopropyl(phenyl)methyl, (1S,2R)-1,7,7-trimethylbicyclo[2.2.1]hept-2-yl, phenyl, 2-chlorophenyl, 3-chlorophenyl, 4-chlorophenyl, 2,4-dichlorophenyl, 2,6-dichlorophenyl, 3,4-dichlorophenyl, 3,5-dichlorophenyl, 2,4,6-trichlorophenyl, 2,4,6-trifluorophenyl, 2-methoxyphenyl, 4-methoxyphenyl, 2,4-dimethoxyphenyl, 2,6-dimethoxyphenyl, 2-methylphenyl, 3-methylphenyl, 4-methylphenyl, 4-nitrophenyl, 2-(trifluoromethyl)phenyl, 3-(trifluoromethyl)phenyl, 4-(trifluoromethyl)phenyl, 2-(trifluoromethoxy) phenyl, 4-(trifluoromethoxy)phenyl, 4-tert-butylphenyl, biphenyl-2-yl, biphenyl-3-yl, biphenyl-4-yl, 3-phenoxyphenyl, 4-phenoxyphenyl, 1-naphthyl, 2-naphthyl, phenylethynyl, 2-thienyl, pyridin-2-yl, pyridin-3-yl, pyridin-4-yl, quinolin-5-yl, quinolin-6-yl, quinolin-7-yl, quinolin-8-yl, isoquinolin-5-yl, 1,3-benzoxazol-4-yl, trifluoromethyl, dimethylamino or trimethylsilyl, or an agrochemically active salt thereof.

3. A method for controlling phytopathogenic harmful fungi, comprising applying a compound of the formula (I) as claimed in claim 1 to the to phytopathogenic harmful fungi, their habitat, or combinations thereof.

4. A composition for controlling phytopathogenic harmful fungi, comprising at least one compound of the formula (I) as claimed in claim 1, and an extender, or a surfactant, or combinations thereof.

5. A process for preparing a compound of the formula (I) according to claim 1, which comprises at least one of steps c. to e. below:

c. converting a compound of the formula (IV) or (VII) into a compound of the formula (III) or (VIII), in each case by hydrolysis in the presence of a base and, optionally, in the presence of a solvent, according to the reaction scheme below:

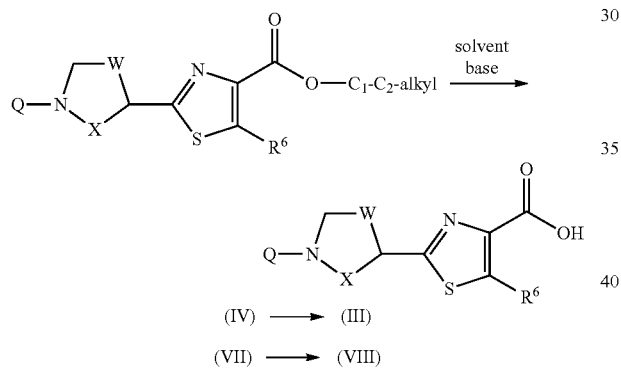

(IV) ⟶ (III)
(VII) ⟶ (VIII)

where

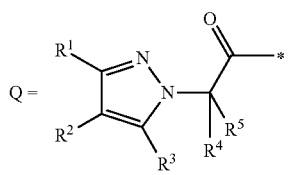

for compounds of the formulae (IV) and (III),

Q=acetyl, $C_1$-$C_4$-alkoxycarbonyl, benzyl or benzyloxycarbonyl, for compounds of the formulae (VII) and (VIII), and W, X, $R^1$, $R^2$, $R^3$, $R^4$, $R^5$ and $R^6$ are as defined in claim 1;

d. reacting a compound of the formula (III) or (VIII) with a compound of the formula (II) to give a compound of the formula (I) or (IX), in each case, optionally, in the presence of a coupling agent, a base and a solvent, according to the reaction scheme below:

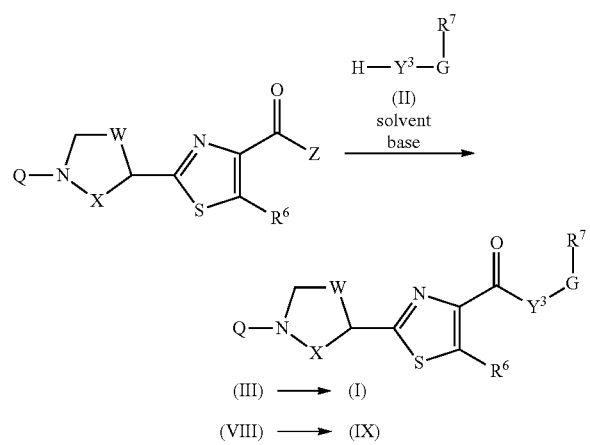

(III) ⟶ (I)
(VIII) ⟶ (IX)

where

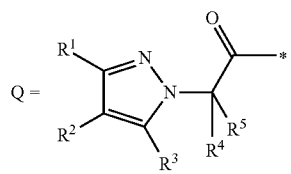

for compounds of the formulae (III) and (I),

Q=acetyl, $C_1$-$C_4$-alkoxycarbonyl, benzyl or benzyloxycarbonyl, for compounds of the formulae (VIII) and (IX), Z=OH or chlorine, and W, X, $Y^3$, G, $R^1$, $R^2$, $R^3$, $R^4$, $R^5$, $R^6$ and $R^7$ are as defined in claim 1;

e. converting a compound of the formula (I) into a compound of the formula (I) in the presence of a sulfurizing agent and, optionally, in the presence of a solvent, according to the reaction scheme below:

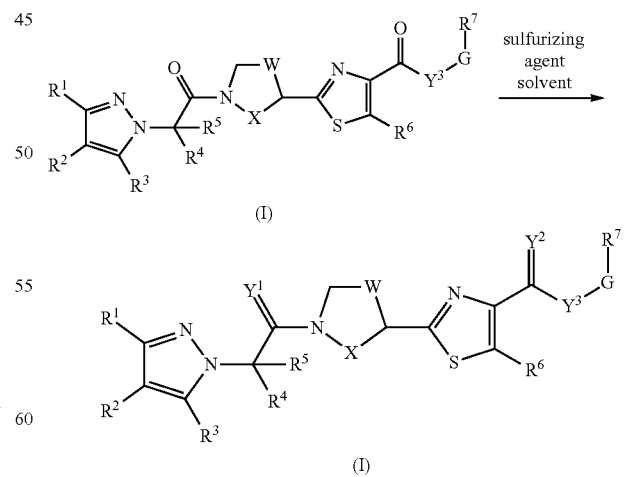

where
$Y^1$=sulfur or oxygen,
$Y^2$=sulfur or oxygen, wherein at least one of $Y^1$ and $Y^2$ is sulfur, and W, X, $Y^3$, G, $R^1$, $R^2$, $R^3$, $R^4$, $R^5$, $R^6$ and $R^7$ are as defined in claim 1.

6. A method for controlling phytopathogenic harmful fungi on seed, comprising applying a compound of the formula (I) as claimed in claim 1 on seed.

7. A method for controlling phytopathogenic harmful fungi on transgenic plants, comprising applying a compound of the formula (I) as claimed in claim 1 on transgenic plants, their habitat, or combinations thereof.

* * * * *